(12) United States Patent
Pfenninger et al.

(10) Patent No.: US 6,566,047 B1
(45) Date of Patent: May 20, 2003

(54) METHOD FOR IDENTIFYING NEURITE-GROWTH PROMOTING AGENTS

(75) Inventors: Karl Pfenninger, Englewood, CO (US); Becky De La Houssaye, Denver, CO (US); Keith Mikule, Arvada, CO (US); Steve Helmke, Englewood, CO (US); Harry Drabkin, Denver, CO (US)

(73) Assignee: The Regents of the University of Colorado, Boulder, CO (US)

( * ) Notice: Subject to any disclaimer, the term of this patent is extended or adjusted under 35 U.S.C. 154(b) by 0 days.

(21) Appl. No.: 09/463,259

(22) PCT Filed: May 21, 1999

(86) PCT No.: PCT/US99/11320

§ 371 (c)(1),
(2), (4) Date: Apr. 18, 2000

(87) PCT Pub. No.: WO99/61585

PCT Pub. Date: Dec. 2, 1999

Related U.S. Application Data

(60) Provisional application No. 60/085,477, filed on May 22, 1998.

(51) Int. Cl.[7] .............................. C12Q 1/00; C12Q 5/00; C07K 14/00; C07K 2/00
(52) U.S. Cl. ......................... 435/4; 435/325; 435/375; 530/300; 530/350
(58) Field of Search ........................... 435/4, 325, 375; 530/300, 350

(56) References Cited

U.S. PATENT DOCUMENTS 4,988,621 A    1/1991 Ruoslahti et al. ........ 435/240.2

OTHER PUBLICATIONS

Behar et al. Semaphorin III is needed for normal patterning and growth of nerves, bones and heart. NAture 383(6600): 525–528, 1996.*
Brambilla et al. Semaphorin SEMA3F localization in malignant humna lung and cell lines. Am J Pathol 156(3): 939–950, 2000.*
de la Houssaye et al. Thrombin–triggered pseudopod detachment in nerve growth cones and motile cancer celss. Mol Biol Cell 8(Suppl): 265A, 1997.*
de la Houssaye et al. Thrombin–induced growth cone collapse: involvement of phospholipase A2 ad eicosanoid generation. J Neurosci 19(24): 10843–10855, 1999.*
Fan et al. The organization of F–actin and microtubules in growth cones exposed to a brain–derived collapsing factor. J Cellular Biol 121: 867–878, 1993.*
Feng et al. Development of a potent thrombin receptor ligand. J Medicinal Chemistry 38: 4125–4130, 1995.*
Fritsche et al. Differential cytoskeletal changes during growth cone collapse in response to hSema III and thrombin. Mol Cell Neurosci 14: 398–418, 1999.*
Grand et al. Cellular consequences of thrombin–receptor activation. Biochem J 313: 353–368, 1996.*
Kolodkin, AL. Semaphorin function in neuronal growth cone guidance. J Neurochem 69: PS162, 1997.*
Lohse et al. Axonal origin and purity of growth cones isolated from fetal rat brain. Dev Brain Res 96: 38–96, 1996.*
Ross et al. Thrombin causes pseudoped detachment via a pathway involving cytosolic phospolipase A2 and 12/15–lipoxygenase products. Cell Growth Diff 11: 19–30, 2000.*
Shepherd et al. Collapsin–1/semaphorin D is a repellent for chick ganglion of remak axons. Dev Biol 212: 42–53, 1999.*
Shoji et al. Zebrafish semaphorin Z1a collapses specific growth cones and alters their pathway in vivo. Development 125: 1275–1283, 1998.*
Cho et al. Novel caffeic acid derivatives: extremely potent inhibitors of 12–lipoxygenase. J Medicinal Chem 34: 1503–1505, 1991.*
Honn et al., *Cancer and Metastasis Reviews*, 13:365–396 (1994).
Kolodkin, *Cell Biology*, 6:15–22 (1996).
Mikule et al., "Collapsin Signalling Involves Phospholipase $A_2$ Activation" Society for Neuroscience (1997) Abstract.
Wojtukiewicz et al., *Int. J. Cancer*, 54:793–806 (1993).

* cited by examiner

*Primary Examiner*—Gary Kunz
*Assistant Examiner*—Bridget E. Bunner
(74) *Attorney, Agent, or Firm*—Sheridan Ross P.C.

(57) ABSTRACT

The present invention provides methods of identifying and using compounds that modulate cell motility. Such compounds can be used to inhibit cancer cell metastasis or promote neurite growth and regenaration. The methods generally relate to the repellent-receptor signalling pathway that controls cellular attachment and detachment to a substratum.

17 Claims, 33 Drawing Sheets

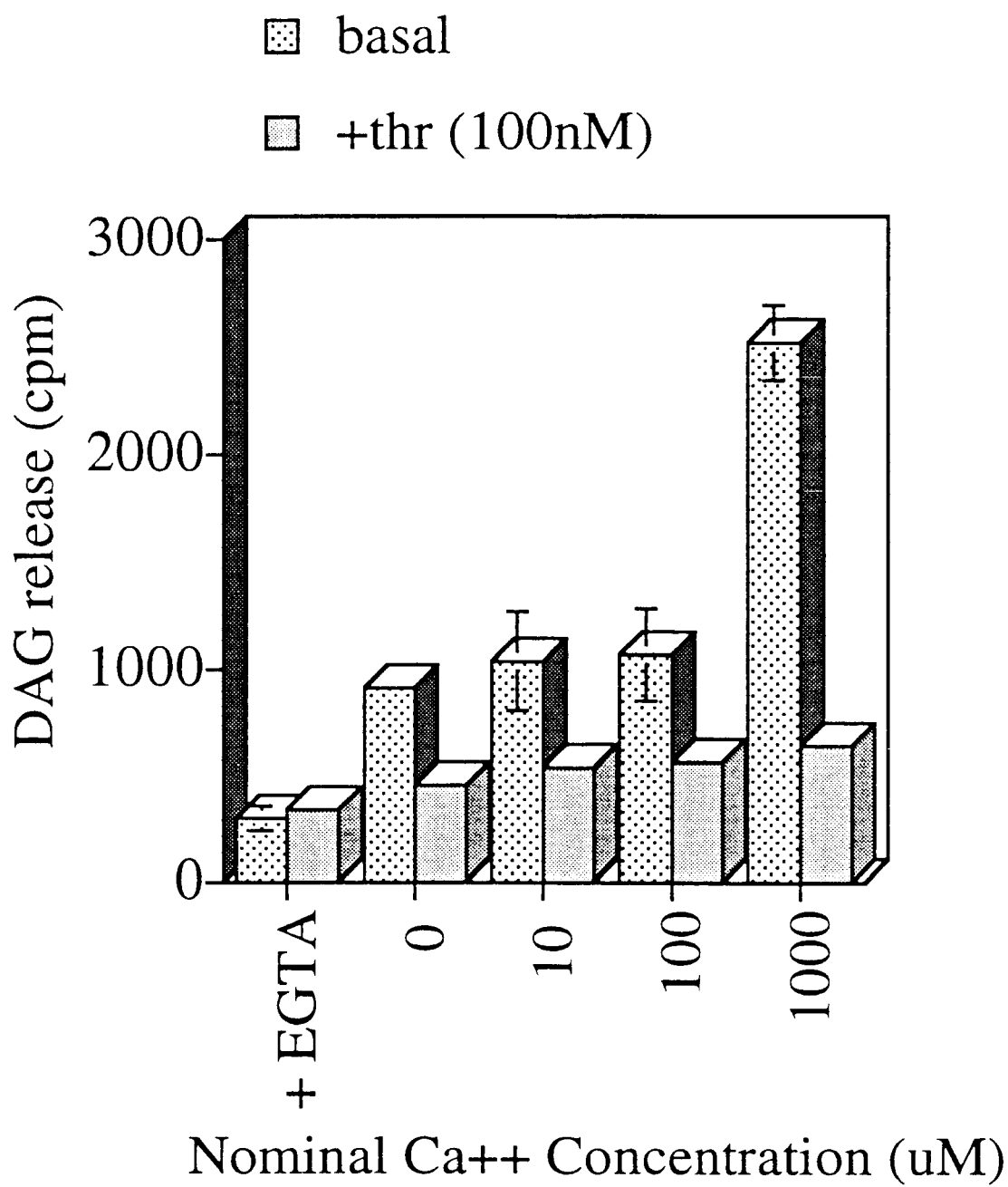

METHOD FOR IDENTIFYING NEURITE-GROWTH PROMOTING AGENTS

CROSS-REFERENCE TO RELATED APPLICATIONS

This application is a national stage application under 35 U.S.C. §371 of PCT Application No. PCT/US99/11320, filed May 21, 1999, which claims the benefit of priority under 35 U.S.C. §119(e) to U.S. Provisional Application Serial No. 60/085,477, filed May 22, 1998.

GOVERNMENT RIGHTS

This invention was supported in part with funding provided by NIH Grant No. NS24672, awarded by the National Institutes of Health, and by BNS Grant No. 9109775, awarded by the National Science Foundation. The government may have certain rights to this invention.

FIELD OF THE INVENTION

The present invention relates to methods for identifying and using compounds that inhibit cancer cell metastasis or promote neurite growth and regeneration.

BACKGROUND OF THE INVENTION

Amoeboid locomotion requires a quasi-metastable state of the adhesion sites, i.e., of the interactions between (i) the cell's contractile apparatus, (ii) adhesion molecules and other plasma membrane components, and (iii) the growth substratum. FIG. 1 plots in principle the relationship between the strength of cell adhesion to the substratum and cell motility. At the extreme ends of the curve, locomotion is reduced to zero. At these ends, the cell is either too tightly adherent, or it is so loosely attached that force generation against the substratum is impossible. Optimum motility requires an intermediate, dynamic state that facilitates the making and breaking of adhesions as the cell moves. In other words, a factor that increases motility would not be expected to increase or decrease attachment but to facilitate assembly and disassembly of adhesion sites. Knowledge of the attachment mechanism has increased significantly in recent years, but knowledge about detachment has been rudimentary until recently. Both processes must be elucidated to understand the motility of metastatic cancer cells, and the influence of motility factors.

For example, chemorepellents provide important guidance cues for growth cones during nervous system development. These repellents cause developing neurites to change their course of outgrowth away from the repellent source and, thus, play a critical role in pathfinding for growing or regenerating nerves. However, the mechanisms of action of the repellents are not well understood.

The establishment of metastases is a complex, multi-step phenomenon that begins with dissociation of cancer cells from the primary tumor and invasion of surrounding tissues. Although understanding of the metastatic process is incomplete, at least four elements (in addition to continued cell proliferation) have been identified in recent years: (i) changes in cell adhesion molecules, (ii) secretion/surface expression of proteases, (iii) increased cell motility, and (iv) vascularization of primary and secondary tumors. In addition, factors that promote metastatic progression include genetic instability and defects in cell-cell signaling. For example, loss of the NDP kinase-like protein encoded by nm23, a putative metastasis-suppressor gene, seems to result in altered signaling responsiveness, e.g., in motility assays described in MacDonald et al., *J. Biol. Chem.* 268:25780–25789 (1993) and Kantor et al., *Cancer Res.* 53:1971–1973 (1993). Motility has been correlated with metastatic potential as reported in Guirguis et al., *Nature*, 329:261–263 (1987); Partin et al., *Cancer Res*, 48:6050–6053 (1988); Partin et al., *Proc Natl Acad Sci. USA*, 86:1254–1258 (1989); Mohler, supra.; and Stearns & Steams, *Cancer Metastasis Rev.* 12:39–52 (1993).

A growing number of factors contributing to metastastic progression are being identified. The recently identified KAI 1 gene encodes a putative cell adhesion molecule whose expression reduces prostate carcinoma cell motility and metastasis. However, a universal prognostic marker of prostate carcinoma has not been identified to date. Therefore, a thorough understanding of the mechanisms that trigger invasive cancer cell behavior is particularly important for prostate carcinoma.

Vertebrate amoeboid cell systems, such as polymorphonuclear leukocytes, platelets and the nerve growth cone (the pseudopodal, enlarged leading edge of the growing nerve fiber) have been studied in some detail. Pseudopods of locomoting cells are filled with actin microfilaments, and there is considerable knowledge of the components involved in the regulation of polymerization and of force generation in the actin-based cytoskeleton. At so-called focal adhesion sites, the cytoskeleton interacts with the plasma membrane and, via adhesion molecules, with the extracellular matrix or adhesion molecules on neighboring cells. To make locomotion possible, attachment of adhesion molecules to the growth substratum has to be regulated coordinately with the binding of these adhesion molecules, via linker proteins, to the actin cytoskeleton. Numerous proteins are involved in the intracellular interactions. They include, among others, talin, vinculin, Src family non-receptor tyrosine kinases, focal adhesion kinase, certain types of protein kinase C, and the protein kinase substrate, myristoylated alanine-rich C-kinase substrate (MARCKS) (Burridge et al., *Ann Rev Cell Biol.* 4:487–525 (1988); Jaken et al., *J. Cell Biol.*, 109:697–704 (1989); Luna and Hitt, *Science* 258:955–964 (1992); Blackshear, *J. Biol. Chem.*, 268:1501–1504 (1993); Schaller and Parsons, *Trends Cell Biol.* 3:258–262 (1993)).

There are several classes of adhesion molecules. At least in the case of integrins and cadherins, there is evidence that they function not only as adhesion molecules, but also as receptors that signal ligand binding across the membrane. Conversely, external ligand affinity can be modulated by integrin or cadherin phosphorylation on the inside of the cell. Outside-in signaling triggers focal adhesion assembly by a process known to require tyrosine kinase activity. In summary, adhesion sites are distinctive cell organelles comprised of protein assemblies that regulate cell attachment and play an important role in amoeboid motility.

A variety of amoeboid systems, including macrophages, platelets and nerve growth cones, exhibit high activity of cytosolic phospholipase $A_2$ ($cPLA_2$) and generate high levels of cytosolic arachidonic acid (AA). In platelets, $cPLA_2$ is activated via the thrombin receptor. Also, ras-transfected cancer cells with increased motility exhibit increased $cPLA_2$ activity. This suggests a role for $cPLA_2$ and its product, AA, in the regulation of cell motility. The eicosanoid, 12(S)-hydroxyeicosatetraenoic acid (12(S)-HETE) has long been known to affect leukocyte motility and has been implicated in cancer cell attachment. 12-lipoxygenase (12-LOX), is the enzyme that converts AA into 12-hydroperoxyeicosatetraenoic acid, which is reduced spontaneously to 12(S)-HETE. A correlation between metastatic potential and expression levels of 12-LOX has been reported in Honn et al., *Cancer Metastasis Rev.* 13:365–396 (1994). These observations also implicate AA and HETEs in the regulation of cell attachment and/or motility.

There is considerable interest in eicosanoids as they relate to the prostate because unsaturated fatty acids inhibit steroid 5α reductase and lowered AA levels have been correlated with increased malignancy of prostate carcinoma cells. In addition, 12-LOX is elevated in advanced-stage human prostate carcinoma.

Results obtained by other laboratories and discussed above were generated in isolation and never synthesized in the manner described herein. Furthermore, the signaling pathway mediating cellular shape and motility responses to thrombin had not been elucidated. In fact, prior to the present invention, functional assays were performed in vivo or in culture with intact cells and monitored a combination of cellular behaviors such as cell adhesion, detachment and motile behavior.

Accordingly, a need exists for assays that can quickly and selectively identify agents that modulate cell adhesion and detachment. The present invention satisfies this need and provides related advantages as well.

SUMMARY OF THE INVENTION

The present invention generally relates to methods of identifying agents that modulate the motility of cells. In one aspect, the methods are accomplished by (a) attaching pseudopods, preferably cancer cells or neurite growth cones, on a substratum, (b) exposing the attached pseudopods to a putative agent, and (c) determining the effect of the putative agent on the pseudopods, wherein a significant change in pseudopod attachment indicates the putative agent is an effective repellent agent. The pseudopods are preferably attached to the substratum by first diluting the pseudopods 1:1 into 2×modified Krebs buffer containing 22 mM HEPES buffer, pH 7.2 and a reagent to increase osmolarity, preferably 22 mM sucrose, and then by spinning the solid support containing the substratum for a sufficient speed and time to facilitate attachment, preferably about 2000×g to about 10,000×g, for up to 60 minutes, and more preferably about 5000×g for 15 minutes at room temperature.

Various methods for determining the effect of the putative agent on the pseudopods include, for example, monitoring pseudopod detachment, pseudopod elongation, pseudopod retraction, cell extension, or adhesion sites. In one embodiment, the amount of pseudopods detached from the substratum is measured. In these methods, a significant amount of detached pseudopods indicates the usefulness of the putative agent as a repellent. Particularly useful repellents will detach at least 35%, preferably at least 50%, and most preferably at least 90% of the pseudopods from the substratum.

In another aspect of the invention, the methods are accomplished by exposing whole cells or components of cells, such as the pseudopods identified above, to a putative repellent agent. The ability of the putative agent to activate a parameter of the repellent signaling pathway is then determined. The parameters assayed for activation in these methods include cytosolic phospholipase $A_2$ ($cPLA_2$), 12-lipxygenase (12-LOX) or protein kinase C (PKC). Activated $cPLA_2$ is measured by the amount of arachidonic acid (AA) produced after exposure to the putative agent, whereas activated 12-LOX is measured by the amount of either 12-hydroperoxyeicosatetraenoic acid or preferably 12(S)-hydroxyeicosatetraenoic acid (12(S)-HETE). Protein kinase C activation can be measured by the amount of phosphorylated growth cone proteins, such as phosphorylated MARCKS, MacMARCKS, GAP43, or exogenous snythetic substrate (poly)peptides, such as the phosphorylation site domain peptide (PSD).

The invention further relates to methods of identifying neurite-promoting agents that inhibit the ability of an endogenous repellent from affecting cell motility. The methods are accomplished by attaching cellular pseudopods to a substratum, exposing the attached pseudopods to a putative agent in the presence of a known repellent, and thereafter determining the amount of attached or detached pseudopods. A useful neurite-promoting agent will have been identified if at least 75%, preferably at least 85%, and most preferably at least 95% of the pseudopods remain attached to the substratum. Alternatively, the methods can be accomplished by determining whether the putative agent inhibits the activation of a parameter in the repellent signaling pathway, such as $cPLA_2$, 12-LOX or protein kinase C.

The invention also relates to therapeutic methods of using the agents identified in the above assays. The methods include inhibiting cell motility, for example the metastasis of cancer cells, by administering an effective amount of a repellent agent identified in the assays of the present invention. Methods of promoting neurite growth or regeneration are also provided in which a neurite-promoting agent is administered to a patient in need of increased neurite formation.

The invention also provides methods of identifying a repellent receptor in which a thrombin-responsive cancer cell that does not respond to a specific repellent is transfected with a nucleic acid library from a cell that responds to the repellent. The transfected cancer cells are then exposed to the repellent of interest. If a parameter within the repellent signaling pathway is activated in a transfected cell, the novel repellent receptor is thereafter identified. The identification of novel repellent receptors can lead to the production of repellent agonists or antagonists depending on the desired effect.

A further aspect of the invention relates to methods of using the repellent signaling pathway to develop diagnostic tests for the metastatic potential of cancer cells. The methods involve determining the presence of repellents or repellent receptors or determining whether the cancer cells contain a functional signaling pathway. Test samples from surgically removed tumors, tumor biopsies or cell smears can be used in these methods to determine the metastatic potential of the tumor cells. The deficiency of any of these markers provides evidence the tumor cells may have increased metastatic potential.

BRIEF DESCRIPTION OF THE DRAWINGS

FIG. 3B. Thrombin does not activate phospholipase C in GCPs, measured as $^{14}C$-diacylglycol (DAG) release from $^{14}C$-AA-PI at different calcium levels.

FIG. 12D shows the results of pretreatment with the protein kinase C inhibitor, calphostin C, on the effect of 12(S)-HETE. For explanation of the plot, see FIG. 11.

FIG. 14A shows the control and concentrations of 12(S)-HETE ranging from $10^{-12}$M to $10^{-10}$M. FIG. 14B shows concentrations of 12(S)-HETE ranging from $10^{-9}$M to $10^{-6}$M. The distribution patterns were fitted by gamma regression, and the vertical line indicates the mode. The same data are also shown as a whisker-box plot in FIG. 12A.

LC/MS$^2$ was used to demonstrate GCP synthesis of specific HETE isomer(s). FIGS. 25B and 25D show corresponding deuterated standards, which yield fragments of greater mass. Based on scale and peak width, 12-HETE is the predominant species, but a significant level of 15-HETE is evident. 5-HETE was not detected.

DETAILED DESCRIPTION OF THE INVENTION

Figure 1:
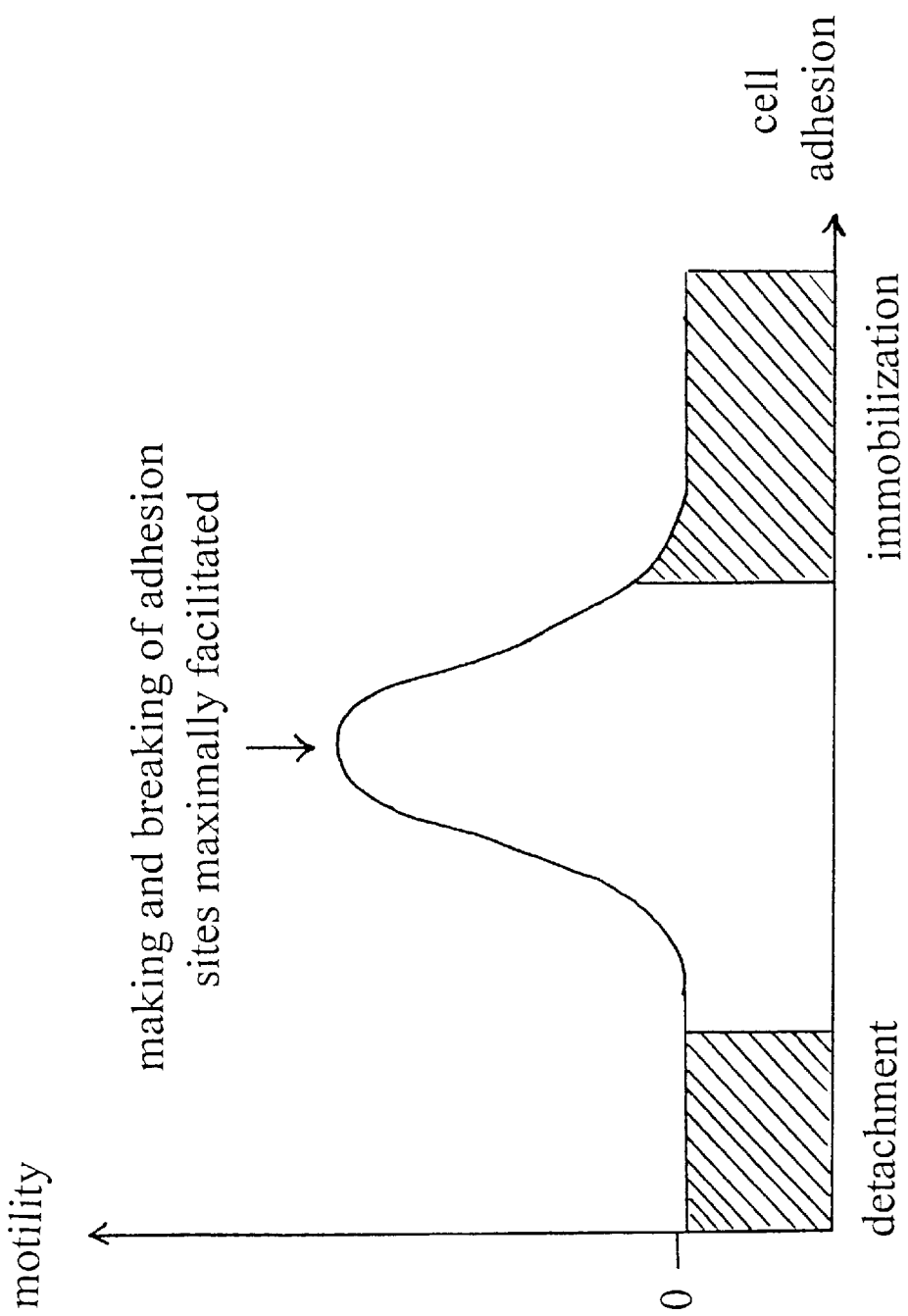
FIG. 1 shows the relationship between cell adhesion and motility.
Figure 2:
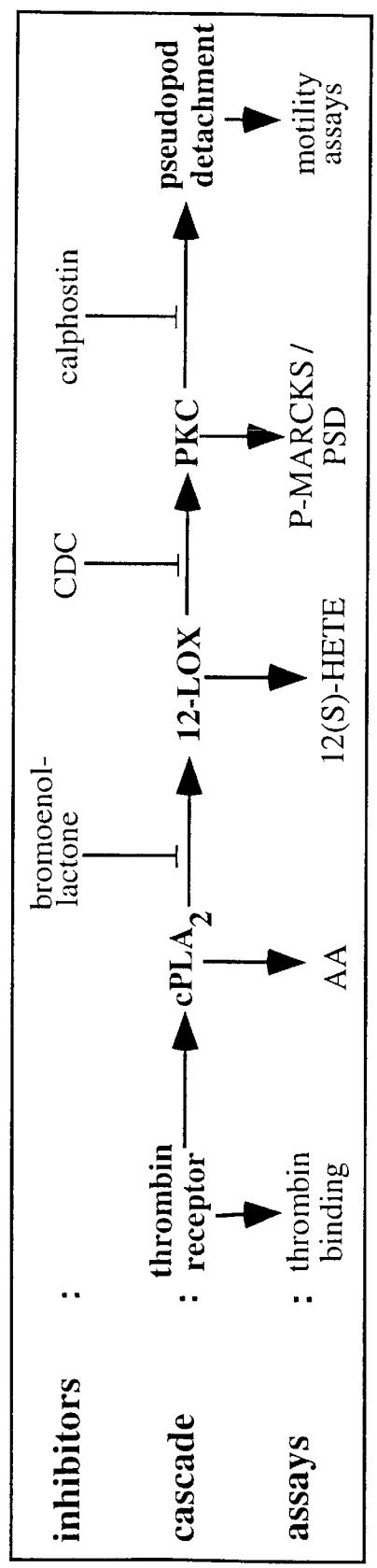
FIG. 2 depicts the signaling pathway regulating cell adhesion.

The present invention is based on the elucidation of a receptor-activated signaling pathway that leads to cell detachment and eventual inhibition of cell motility. As shown in FIG. 2. the pathway starts with the stimulation of cytosolic phospholipase A$_2$ (cPLA$_2$) when a repellent molecule activates a repellent receptor. The stimulation of cPLA$_2$ produces high levels of endogenous arachidonic acid (AA). AA is then converted by 12-lipoxygenase (12-LOX) into 12(S)- and some 15(S)-hydroxyeicosatetraenoic acid (12(S)-HETE and 15(S)-HETE, respectively) which, in turn, activates protein kinase C at adhesion sites. The substrates for protein kinase C include MARCKS, MacMARCKS and GAP43. The phosphorylation of MARCKS, MacMARCKS or GAP43 leads to loosening of the adhesion site, resulting in either pseudopod spreading or, in the extreme case, pseudopod detachment. Concomitantly, the affinity of adhesion molecules for their extracellular ligand also may be reduced. Therefore, pseudopod repellents decrease cell adhesion that can lead to either increased motility with weak stimulation or cell detachment and repulsion with strong stimulation.

Non-metastatic cells respond to repellents via the signaling pathway which prevent them from moving out of a tissue. For example, neurite growth may be inhibited by these repellents. In contrast, metastatic cancer cells ignore the repellents because they lack the functional receptor and/or have defects in the signaling pathway. The present invention relates to the identification of agents that can regulate this pathway.

A. Repellent Assays

One aspect of the invention relates to methods for identifying an agent that promotes significant cell detachment and inhibits the motility of a cell. The assays are generally accomplished by:

(a) attaching cellular pseudopods to a desired substratum;

(b) exposing the attached cellular pseudopods to a putative repellent agent; and (c) determining the effect of the putative agent on the pseudopods, wherein a significant change in pseudopod attachment indicates the putative agent is an effective repellent agent.

As used herein, the term "cellular pseudopods" includes any cell or cell component that can attach to a substratum and contains a functional repellent signaling pathway, including, for example, neuronal cells, cancer cells and hybrids of repellent-responsive cancer cells described below. In addition, cellular pseudopods can also be constructed through recombinant or transfection technology in which genes encoding a component involved in the pathway, for example, a desired repellent receptor, can be inserted into host cells according to methods known in the art.

Growth cones (tips of growing neurites) are particularly useful in these assays. They can be isolated from fetal or newborn brains as described, for example, in Pfenninger et al., *Cell* 35:573–584 (1983), incorporated herein by reference. The growth cones can also be derived from other cellular sources, for example, cultures of growing neuronal cells.

Cancer cells, especially highly motile cancer cells, are also useful in these assays. The cells can be obtained from a primary source such as surgically removed tumors, tumor biopsies or cell smears. Alternatively, cultured cancer cells can be grown and harvested for this purpose. In this regard, highly motile prostate carcinoma or melanoma cells are particularly useful in these assays.

Hybrid cells can also be produced in these assays. These cells can be constructed from a first cell (cell type X) that has a receptor for a putative repellent and a second cell (cell type A) that responds fully to a known repellent (for example, thrombin), indicating that the signaling pathway is functional in cell type A. The XA hybrid cells can then produced according to methods known in the art and contain the putative repellent receptor contributed by cell type X and the functional signaling pathway contributed by cell type A. The hybrids can then be used in the assays of the present invention to determine whether the putative repellent activates the signaling pathway as shown by cell detachment.

In the first step of the assay, the cellular pseudopods are attached to any desired substratum according to any method known in the art or as described in the examples below. Preferably, the cellular pseudopods are plated on substrata that are composed of extracellular matrix molecules or cellular adhesion molecules that are attached to a solid support, such as plastic culture dishes and the like. The solid support is optionally pre-coated with nitrocellulose or other similar coating prior to the addition of extracellular matrix molecules or cellular adhesion molecules. Extracellular matrix molecules useful in these methods include, for example, laminin, fibronectin, collagen or any combination of these proteins. Cellular adhesion molecules can include, for example, L1, N-CAM, cadherin, glycolipids, oligosaccharides, or synthetic polypeptides of these molecules, as well as any combination of these cellular adhesion molecules.

The culture dishes or other solid support can be centrifuged for a sufficient time and at a sufficient speed to facilitate adhesion site formation. The solid support can be centrifuged at a speed from about 2,000×g to about 10,000×g for up to 60 minutes, preferably at about 5,000×g for about 15 minutes at room temperature.

The pseudopods are then rinsed in an appropriate buffer in order to separate the adherent pseudopods from the non-adherent pseudopods.

In the next step of the assays, the attached pseudopods are then exposed to potential repellent molecules or preparations. Such preparations may be extracts of adult or developing tissues and subfractions thereof, or purified or synthetic (poly)peptides or other factors, for example, cytokines. growth factors or neurotransmitters.

In these and other methods described below, effective repellents can be identified qualitatively by examining their effect on the repellent-signaling pathway, for example, by monitoring pseudopod detachment, pseudopod elongation and/or retraction, cell extension, adhesion sites, or other significant change in pseudopod attachment. Methods that can be used to monitor such activity are provided in the examples below and include, for example, the Boyden chamber assay, the pseudopod length assay, various microscopic techniques and, as identified above, various protein assays.

In one embodiment, methods for identifying repellents by monitoring pseudopod detachment are generally accomplished by:
  (a) attaching cellular pseudopods to a desired substratum;
  (b) exposing the attached cellular pseudopods to a putative repellent agent; and
  (c) determining the amount of cellular pseudopods detached from the substratum.

In these methods, the detached pseudopods are recovered from the supernatant by any method known in the art or as described in the examples below. Preferably, the detached pseudopods are centrifuged to isolate them from the supernatant. The detached pseudopods can then be quantified by any protein assay known to those skilled in the art, including, for example, immunological assays. In these methods, a putative agent is an effective repellent if at least 35%, more preferably at least 50%, and most preferably at least 90% of the test cells are detached from the substratum, resulting in reduced cell motility.

Effective repellents can also be identified by monitoring the up-or down-regulation of genes. Methods for measuring gene expression include direct measurement of products of transcription and translation, i.e., mRNA or protein, by means well known in the art, including for example, by the use of microarrays, PCR, Rnase protection, enzyme and immunoassays. The effects of various compounds on the individual genes encoding components of the pathway also can be monitored by attaching a regulatory region of such a gene to a reporter gene, for example, CAT or luciferase, and monitoring expression of the gene upon exposure of the gene construct to a compound of interest.

In addition, genes encoding protein repellent agents can be used to determine alterations in endogenous gene homologs. These alterations could result in decreased and/or altered gene activity and efficacy. Smaller sequences of the gene can also be used as probes in such diagnostic methods. Genes and proteins encoded thereby, and modified versions thereof, can be used to generate antibodies or other probes that are useful as diagnostic agents and potential therapeutic agents.

In a further embodiment of the invention, methods for identifying repellent agents are provided in which parameters within the signaling pathway are monitored. The methods are generally accomplished by:
  (a) obtaining a whole cell or component thereof having a functional repellent signaling pathway;
  (b) exposing the whole cell or component thereof to a putative repellent agent; and
  (c) monitoring a parameter on the repellent signaling pathway, wherein the putative repellent agent inhibits cell motility if the parameter is activated.

As an example of these methods, growth cones (isolated and functionally intact), metastatic cancer cells or the hybrid cells described above are exposed, either in suspension or attached to a substratum, to different repellent factors or their secondary messengers, and a parameter in the signaling pathway is monitored for activation. A parameter is monitored according to methods known to those skilled in the art or as described in the examples below and include, for example, measuring the number and affinity of repellent binding sites, using radiolabeled (preferably $^{14}$C or $^{3}$H) repellent or receptor antibodies, and/or by monitoring the enzyme activities involved in the signaling cascade. These parameters include: (1) different forms of cytosolic phospholipase $A_2$ [calcium-dependent or—independent; measured as arachidonic acid release from different phospholipid substrates, for example, phosphatidylcholine (PC), phosphatidylethanolamine (PE) or phosphatidylinositol (PI)]; (2) different forms of 12-lipoxygenase, measured as production of 12(S)-HETE from arachidonic acid or different phospholipids; and (3) various forms of protein kinase C, measured by phosphorylation of growth cone proteins, such as MARCKS, MacMARCKS, GAP43, or exogenous substrates, such as PSD peptide.

The agents identified by the assays can be used as anti-invasive and anti-metastatic agents for the treatment of cancer cells that are metastatic or susceptible to metastasis. The anti-metastatic agent can be formulated in any pharmaceutically acceptable formulation in any pharmaceutically acceptable form. Such forms and formulations include liquids, powders, creams, emulsions, pills, troches, suppositories, suspensions, solutions, and the like. Thrombin and semaphorin are used in preferred embodiments in accordance with the method of the instant invention. Therapeutically effective amounts of anti-metastatic molecules can be any amounts or doses that are sufficient to bring about the anti-metastatic effect and depend, for example, on patient size and condition and type and location of the cancer. The dosages can be given as a single dose, or as divided doses, for example, divided over the course of several weeks. The anti-metastatic molecules of the instant invention can be administered by any suitable means, including orally or by injection. In the preferred embodiment of the invention, the agent is administered by injection. Such injection can be locally administered to any affected area. For example, thrombin, thrombin receptor-activating peptide ("TRAP"), semaphorin or other repellent can be injected urethroscopically into the prostate.

Modified forms of the agent having increased activity can also be delivered therapeutically. Such modified forms include, but are not limited to, more limited functional domains, site-specific modifications that increase efficacy or activity in functional assays, and modified agents in which functional domains, for example, from humans or other species are combined with effector domains such that species-specific signals can be used to elicit protein activity.

B. Assays for Neurite-Promoting Agents

As previously noted, the invention also relates to the identification of neurite-promoting agents. Evidence indicates that nerve regeneration in the CNS, for example, after spinal cord injury, is inhibited by endogenous repellents. Therefore, agents that block a repellent from binding to its receptor or inhibit a parameter further downstream in the signaling pathway can promote nerve regeneration after injury.

The methods of this aspect of the invention are generally accomplished by:

(a) attaching cellular pseudopods having a functional signaling pathway to a substratum.

(b) exposing the attached cellular pseudopods to a putative neurite-promoting agent; and (c) determining the effect of the putative agent on the cellular pseudopods, wherein a putative agent is a neurite-promoting agent if a repellent is blocked from binding its receptor or the signaling pathway is inactivated.

The method is generally performed as described in the above methods for identifying repellents. Neurite growth cones are particularly useful in these assays and can be derived from neural tumor cells or primary neurons. Neurite-promoting agetns to be tested may be extracts from adult or developing tissues and subfractions thereof, or purified or synthetic (poly)peptides or other factors, for example, cytokincs, neurotransmitters or growth factors. They also may be reagents interfering with the signalling pathway, such as LOX, $PLA_2$ or PKC inhibitors The effectiveness of the putative agent can be determined by a number of methods. In one method, a qualitative or quantitative measure of effectiveness can be determined by the amount of detached pseudopods, or conversely the amount of pseudopods that remain attached to the substrate. In this regard, an effective neurite-promoting agent will have been identified if at least 75%, preferably at least about 85% and most preferably at least about 95% of the pseudopods remain attached to the substratum.

Alternatively, the inhibition of the repellent-stimulated signaling pathway can be determined by assaying for $cPLA_2$, 12-lipoxygenase or protein kinase C activity as described above. If desired, effective inhibitors can then be further tested in neurons or neural tumor cells, such as PC 12, growing in culture to assess whether they can inhibit the effect of specific repellents. This assessment can be done by measuring neurite length and/or direction of neurite growth relative to the repellent source.

The neurite-promoting agents of the present invention can be used to treat disorders caused by the lack of nerve growth or regeneration, for example, spinal cord injury. Those skilled in the art can readily determine a therapeutically effective dose and mode of administration depending on various factors, including, for example, the location and extent of need for neurite generation and patient size. Preferably, the neurite-promoting agent is administered by injection.

C. Identification of a Repellent Receptor

The present invention additionally provides methods for identifying novel repellent receptors that include the following steps:

(a) selecting a known repellent-responsive cancer cell that does not respond to a second repellent;

(b) transfecting the cancer cell with a nucleic acid from a cell that responds to the second repellent;

(c) cloning and culturing the transfected cancer cell with the second repellent;

(d) measuring the amount of an activated parameter in the transfected cancer cell; and (e) identifying the repellent receptor encoded by the nucleic acid.

For example, thrombin-responsive cancer cells that do not respond to a specific repellent, such as semaphorin IV, are transfected with a cDNA library from a cell type responding to this repellent (e.g., semaphorin) and cloned. Cloned transfectants are exposed to the specific repellent and assayed for $cPLA_2$ activation. The cDNA insert in responding cells is used to identify the novel repellent receptor. This is an expression cloning approach. Cancer cells that contain the signaling cascade described above and properly express the transfected receptor to the repellent are expected to increase $cPLA_2$ activity when incubated with the repellent. Therefore, the $cPLA_2$ assay can be used to screen tie cells transfected with the appropriate cDNA library. Once cloned, the transfected insert in responding cells can be isolated by any means known in the art, including, for example, by fluorescence activated cell sorter (FACS), and analyzed to identify the receptor.

The identification of such receptors is desirable because they can be activated to block cancer cell metastasis or inhibited in the CNS to promote nerve regeneration. The receptors can be used in screening methods well known in the art to find compounds that bind thereto to produce the desired effects. Cells expressing the receptor to a repellent or immobilized isolated receptor can be screened for binding of peptides or other chemicals that may interfere with repellent binding (i.e., antagonists). In assays involving cells or cell membranes, such reagents can be tested for activation or inhibition (in the presence or absence of repellent) of the repellent receptor, using the $cPLA_2$ assay or other downstream parameters.

D. Metastatic Potential of Cancer Cells

The invention also provides methods of using the repellent signaling pathway to determine the metastatic potential of cancer cells. The method is based on a deficiency of repellent molecules or receptors and/or when one or more of the signaling steps (i.e., parameters) in the pathway is deficient.

Accordingly, the methods involve:

(a) obtaining, a specimen of the cancer cells; and (b) determining a deficiency of;

(i) repellent in the specimen;

(ii) repellent receptors in the cancer cells; or (Iii) a functional repellent signaling pathway in the cancer cells.

A deficiency in any of (i)–(iii) indicates the cancer cells have increased metastatic potential. Such deficiencies can be determined by: (1) the expression of different repellents, for example semaphorins or thrombin, in the neighborhood of the tumor; (2) the expression of the repellent receptor in the tumor; (3) the expression of gene products of the signaling pathway, such as specific forms of $cPLA_2$ specific forms of 12-lipoxygenase, specific forms of protein kinase C; (4) the enzymatic activity of these gene products; and (5) the expression of MARCKS, MacMARCKS, or GAP43. Such deficiencies are markers of metastatic potential.

Suitable assays for the methods include, for example, Northern blot of gel transfers or spotted extracts, polymerase chain reaction (PCR) of DNA or RNA (with prior reverse transcription), Rnase protection assay and/or in-situ hybridization to determine the presence of particular mutations in, or the expression levels of, specific genes involved in the signaling pathway, its receptor or the repellent that activates it. Additional assays include immunological methods to determine the levels and distributions of the gene products in the cancer cells. Such tests could be, for example, immunoblots of gel transfers or of spotted protein samples, immunoelectrophoresis, or immunocytochemistry of sectioned tissues or cell smears. Finally, enzyme activities (such as 12-LOX or protein kinase C) can be measured in cell homogenates with or without stimulation with putative repellents. Such assays would make use of exogenous, radiolabelled substrates. The test specimens can be surgically removed tumors, tumor biopsies or cell smears. Tissues and cells can be processed for histologic/cytologic examination and/or homogenization, DNA, RNA or protein extraction. The homogenates or extracts can be analyzed by the biochemical methods listed above.

A panel of tests measuring mis-expression of the various proteins involved in the signaling pathway (e.g., repellent, repellent receptor, $cPLA_2$, 12-LOX, PKC isoforms, MARCKS, MacMARCKS, GAP43) is particularly useful. The application of such a panel, via a combination of assays, would provide the strongest evidence of whether a particular cancer has lost its responsiveness to repellents and, therefore, may have increased metastatic potential. Such a panel can include, for example, activation of $cPLA_2$ with known repellents, PCR to test for the presence of specific mutations in the 12-LOX gene, immunochemistry to determine whether a particular protein kinase C isoform is absent from tumor cells (while present in normal cells).

The following Examples are intended to illustrate, but not limit, the present invention.

EXAMPLE 1

Experimental Systems

In several of the examples belong Dunning rat prostate carcinoma cells that have been subcloned into two types of cell lines were used in the studies. The first type include cell lines of high metastatic potential and high motility (MAT-Lu, MAT-LyLu and AT-3), whereas the second type include cell lines of low metastatic potential and low motility (AT-1 and AT-2). Both are described in Isaacs et al., *Prostate* 9:261–281 (1986). The cell lines were used to study whether metastatic cancer cells share some of the molecular characteristics of nerve growth cones. The phenotypes of both types of cell lines are strikingly different. AT-1 and AT-2 cells exhibit typical clonal (i.e., clustered) growth in culture, Whereas the MAT-Lu, MAT-LyLu and AT-3 cells are highly motile and spread rapidly all over the tissue culture dishes. The two cell classes were compared to growing neurons (i.e., growth cones), taking advantage of the rat origin of both systems.

In addition, seven human prostate carcinoma cell lines were used (see Table 2). One or two cell lines of medium to high motility (e.g., PC-3M-MM2 and DU145) are first selected. The PC-3M-MM2 cells disperse rapidly in the dish and, like the MAT-Lu cells, never form colonies. Cells are grown according to standard procedures. Large numbers of aliquots of all cancer cell lines arc collected and frozen in order to avoid the use of higher passage numbers in later experiments. As the experimentation progresses, the motility and morphology of the cells is re-checked to avoid distortion of results by changes in phenotype. For experimental use, cells are kept well below confluence. In order to test for potential effects of the growth matrix, cells are grown for selected experiments not only on serum-conditioned tissue culture plastic but also on laminin, collagen, fibronectin or Matrigel (Life Technologies/GIBCO-BRL, Gaitheresberg, Md.; Becton Dickinson/Collaborative Biomedical Products, Bedford Mass.). Experiments with polypeptides factors are performed with cells that have been grown for a few hours in low-serum (1%) or serum-free medium supplemented with pure bovine serum albumin. The motility, of all cells is assessed quantitatively using the (long-term) Boyden chamber assay as described in Boyden, *J. Exp. Med.* 115:453–466 (1962), incorporated herein by reference. The assays are performed with serum preconditioned, laminin-, or fibronectin-coated membranes, whose pores (8–10 $\mu$m) remain open (vs. those coated with Matrigel). The relative number of cells moving within 3–6 hours across the membrane from the upper well is counted in the presence or absence of IGF-1 in the lower chamber.

To study short-term chemotactic responses of the prostatic carcinoma (CaP) cells to the different agents, the Zigmond chamber, designed originally to study leukocyte chemotaxis and available commercially from NeuroProbe, Inc.(Cabin John, Maryland) is used. These chambers enable the exposure of cells grown on a coverslip (coated with different matrices) to a defined chemical gradient and to study within 15–30 minutes cell orientation in this gradient as described in Zigmond. *J. Cell Biol.* 75:606–616 (1977), incorporated herein by reference. Cell morphology is recorded digitally at different, defined points of the gradient (dependent on concentration range, distance from the higher concentration well, and time after establishment of the gradient; gradients last for about 90 min). The cells' longest axis and orientation is determined, and the angles of these axes relative to the gradient's axis are measured and plotted.

EXAMPLE 2

Repellent Effects on Adhesion Sites and Cell Motility

In this example, the effects of repellent or downstream effectors (AA or 12(S)-HETE) were examined on pseudopod motility, in the presence or absence of the appropriate inhibitors. The Zigmond and Boyden assays are used to look at both short- and long-term responses of the cells to the various agents. The pseudopod length assay also is used to determine short-term effects of the various reagents on the cells. Interference reflection microscopy (IRM) is used to image directly and measure the changes in adhesion sites formed by live cells, under different experimental conditions. Therefore, we can examine quantitatively whether and at which concentrations the repellents—or down-stream effectors of the cascade—change adhesion sites of CaP cells.

Pszeudopod behavior. Pseudopod activity is studied in two different assays: (i) Long-term (2–5 hrs) effects of repellent on motility, assessed in the Boyden chamber (repellent in the lower well, with or without IGF-1 added to the lower chamber). As stated earlier, the Boyden chamber membranes are pre-treated either with laminin, collagen, fibronectin or the like and then with serum. (ii) For short-term analysis, CaP cell orientation is studied and quantified in the Zigmond chamber. For the Zigmond assay, CaP cells are grown at low density on laminin or fibronectin-coated coverslips and then placed upside-down on gradients of different factors. After 15 to 30 min, orientation in the gradient is determined (Zigmond, 1977). By adding different but uniform levels of repellent to a gradient of IGF-1, its influence on pseudopod orientation can be measured and expressed as a dose response. In addition, repellents themselves may orient the cells in a gradient of the appropriate concentration range, and the system can be used to determine this possibility. These assays are carried out with different concentrations of repellent and, as controls, boiled repellent. For thrombin, a positive control is TRAP 6, the peptide SFLLRN (Feng et al., 1995). The Zigmond assay also is performed with different concentrations or gradients of the intermediates, AA and 12(S)-HETE. Other fatty acids and HETEs (1 2(R)-, 5(S)- and 15(S)-) serve as controls. In addition, the effects of cPLA2, 12-LOX and PKC inhibitors on cell motility or orientation are assessed in the presence or absence of repellent stimulation (cf. FIG. 2). To assess pseudopod behavior further, the Zigmond assay can be complemented with the pseudopod length assay described earlier.

Adhesion site microscopy. Adhesion sites can be imaged in live cells by interference reflection microscopy (IRM) as described in Izzard and Lochner, *J Cell Sci* 21:128–159 (1976); Izzard and Lochner, *J Cell Biol* 42:81–116 (1980); Bereiter-Hahn et al., *J Cell Biol* 82:767–779 (1979). Changes in adhesion sites in response to repellents and to intermediates of the cascade are analyzed. Cells are grown on coverslips coated with laminin, collagen, fibronectin or the like and placed upside-down on a Zigmond or custom-made perfusion chamber. These are examined with an upright Zeiss microscope with IRM optics. In different experimental conditions, high-resolution images are captured with a Nikon/Kodak 1000×1000 CCD camera (linked to an Apple PowerMac 9500/132 MHz computer) and stored for later processing. Because the focal adhesions stand out with high contrast, dark against a very light background, the images are processed by contrast enhancement and background subtraction to obtain on/off images of adhesions. The computer measures the focal adhesion areas and their changes as a function of time. Thus, live cells can be analyzed in real time to see the changes induced in focal adhesions by repellents or 12(S)-HETE. These data are useful in conjunction with the biochemical results obtained in Example 6.

This example provides a tight correlation between repellent activation of the different steps of the cascade and changes in pseudopod behavior, especially, pseudopod detachment. The use of up to four different assays of pseudopod activity, together with dose-responses of the different intermediates of the cascade, provides insights into the precise mode of action of the repellent.

EXAMPLE 3

Lipid Messengers in Nerve Growth Cones

Viable nerve growth cones can be isolated in bulk from fetal rat brain (Pfenninger et al., 1983). Such isolated nerve growth cones exhibit a high metabolism of phosphatidylinositol (PI) and phosphoinositides as reported in Pfenninger et al., *The Nerve Growth Cone* pp. 111–123 (Raven Press, N.Y. 1991). The primary pathway of PI metabolism is via $PLA_2$ (Negre-Aminou and Pfenninger, *J. Neurochem.* 60:1126–1136 (1993); and Negre-Aminou et al., *J. Neurochem.* 67:2599–2608 (1996)). Growth cones contain two high molecular weight forms of $cPLA_2$ that are selective for PI and PE, respectively, and calcium-independent. However, the enzymes appear to be recruited to the plasma membrane in the presence of calcium. At least the PI-selective enzyme ($cPLA_2$-PI) is likely to be novel (Negre-Aminou et al., 1996). $cPLA_2$-85 (PE- and PC-selective) is expressed only at very low levels in growth cones as determined by enzyme assay and Western blot (Negre-Aminou et al., 1996).

Figure 3A:
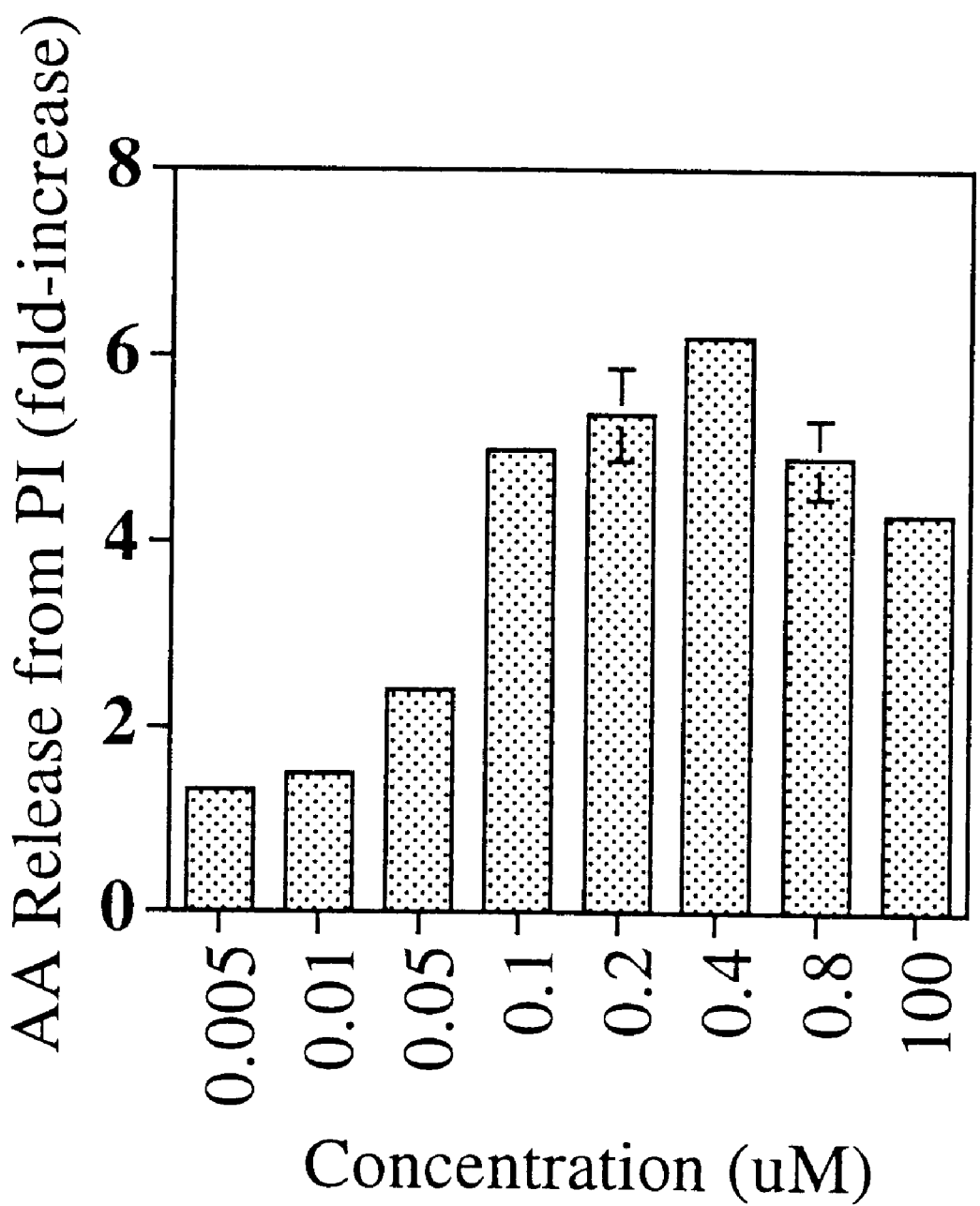
FIG. 3A. Thrombin activation of growth cone $cPLA_2$. Isolated growth cones (GCPs) were preincubated with thrombin for 10 minutes on ice. AA release was measured with $^{14}C$-AA-PI as substrate in a 10-min assay. The 14-amino acid, thrombin-receptor-activating peptide (TRAP) also stimulated $cPLA_2$-PI 4.3-fold.
Figure 4:
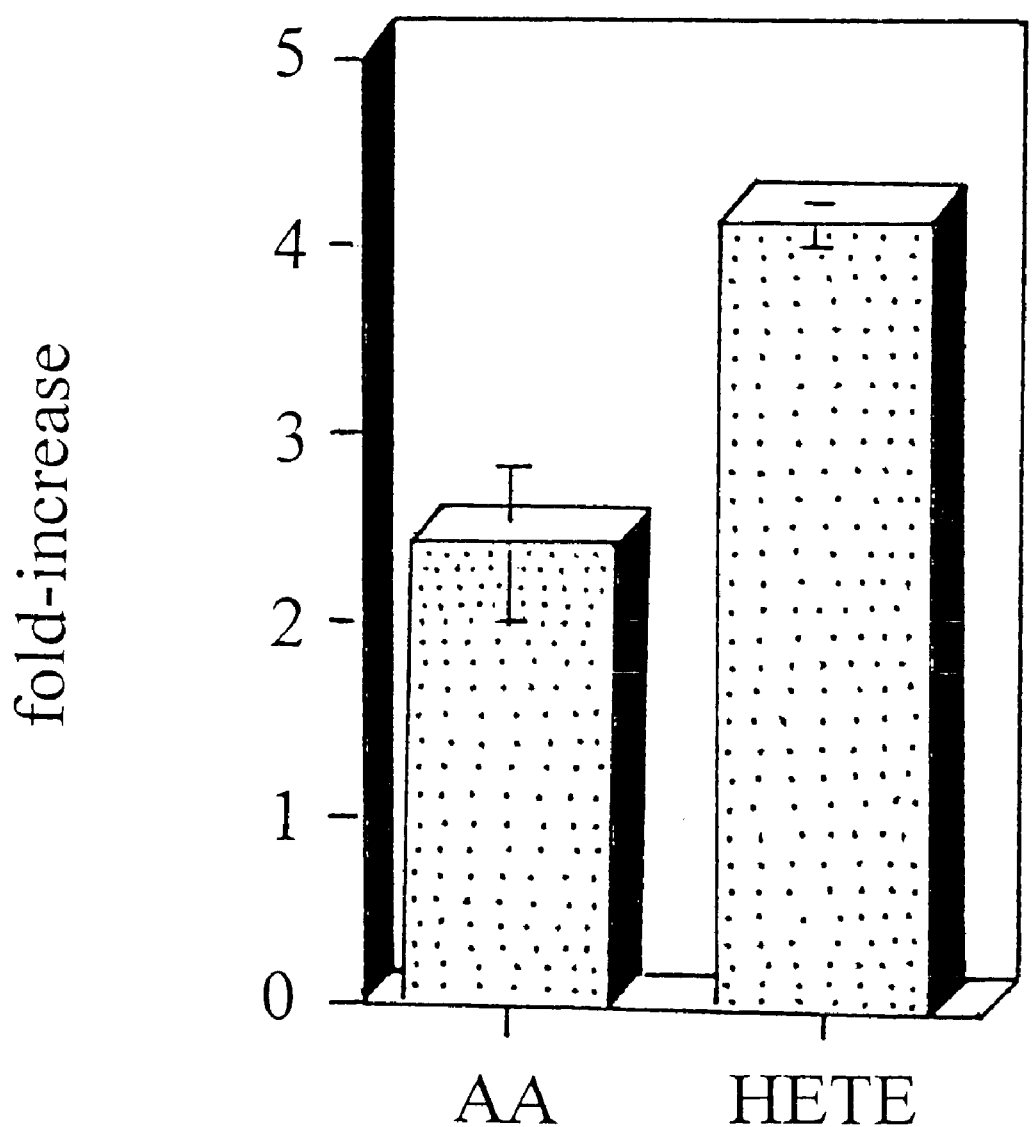
FIG. 4. Thrombin activation of growth cones stimulates generation from $^{14}C$-AA-PC of AA as well as of a compound co-migrating in thin-layer chromatography with 12(S)-HETE. Data are from the same experiment, with separate processing of samples for AA and HETE analysis.
Figure 5:
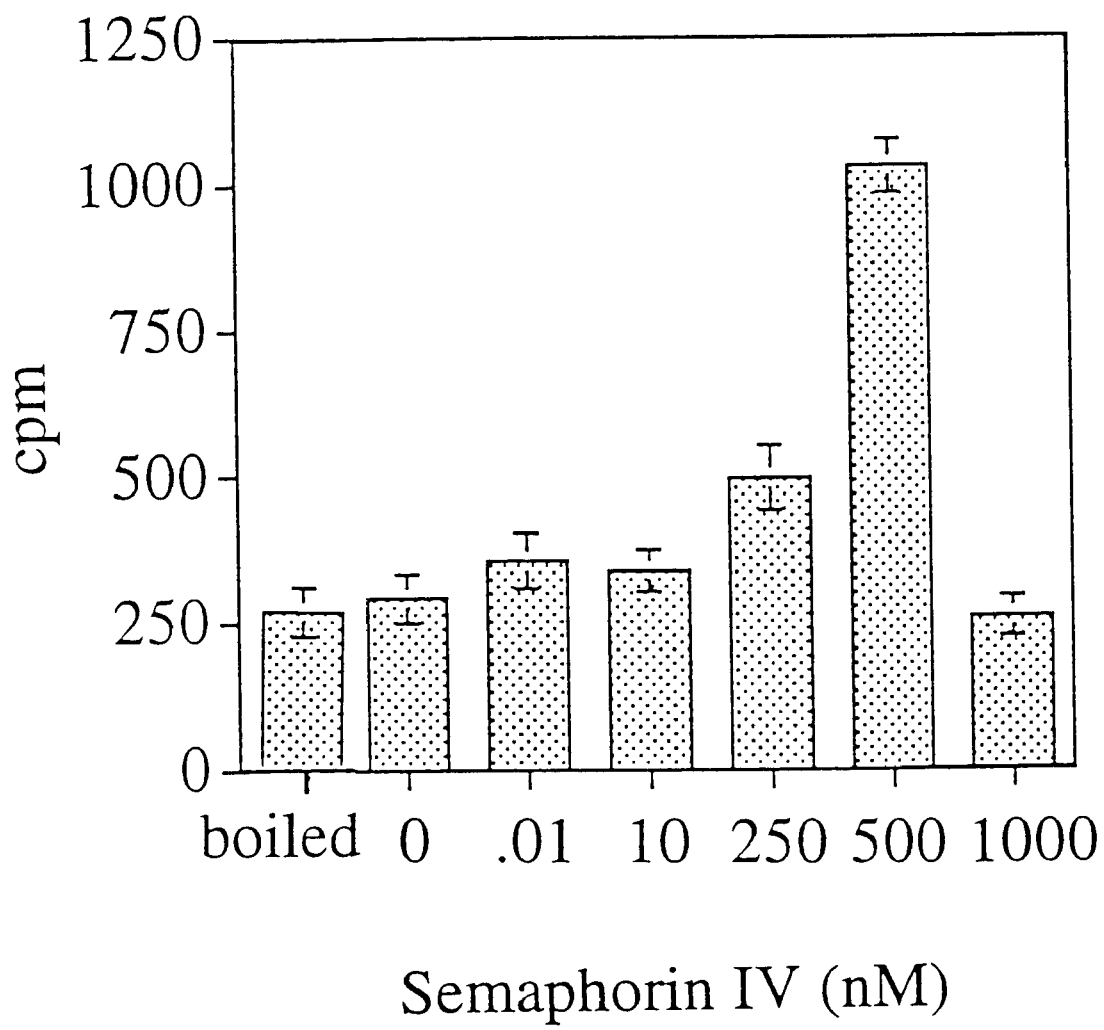
FIG. 5. Semaphorin IV activation of growth cone cPLA$_2$. Assay was as for FIG. 7, but growth cones were incubated with recombinant semaphorin IV. Concentrations are nominal, the concentration of active semaphorin is not known.
Figure 6:
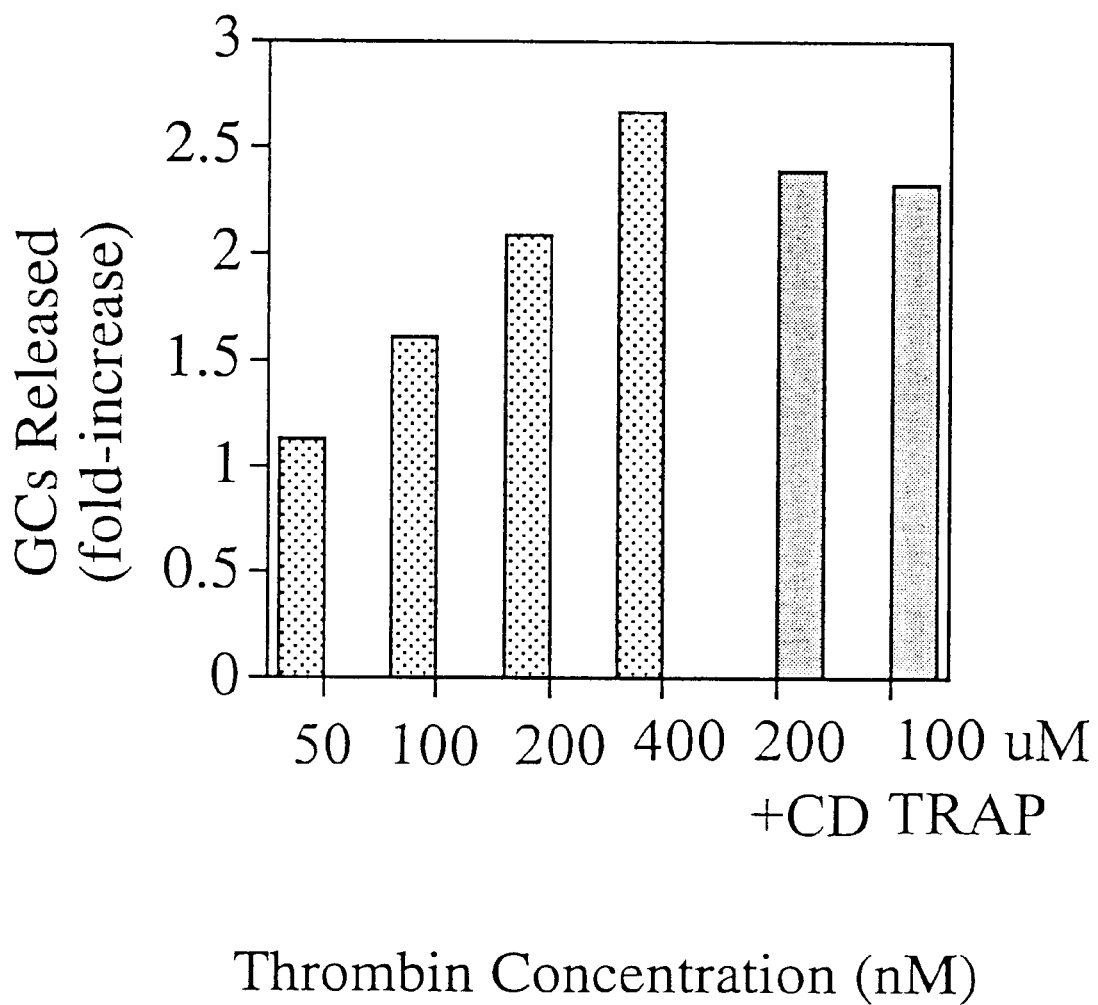
FIG. 6. Thrombin-induced GCP detachment. Isolated GCPs were plated on laminin, incubated for 10 minutes at 37° C., and unbound material was washed off. After 20 min incubation with thrombin or TRAP (6-amino acid peptide) at 37° C., GCPs in the supernatant were collected and quantified by protein assay.

Thrombin (100 nM), a potent growth cone repellent as discussed above, stimulates $cPLA_2$-PI and $cPLA_2$-PE as well as a PC-hydrolyzing $cPLA_2$ about 5-, 7- and 7-fold respectively (FIG. 3), as measured by release of $^{14}$C-AA. Thrombin's effect on growth cone attachment was tested in a cell-free assay involving isolated, viable growth cones plated on laminin. Upon exposure to the same concentrations of thrombin used for the $cPLA_2$ assays, about 46% of growth cones detached, compared to 17% for controls, but only in the presence of calcium (FIG. 6). The $cPLA_2$ activation and growth cone detachment responses could be mimicked (although much less effectively) with proteolytically inactive, thrombin-receptor-activating peptides (TRAPs) described in Feng et al., *J. Med. Chem.* 38:4125–4130 (1995) and Grand et al., *Biochem. J.* 313:353–368 (1996). These results indicate the involvement of a thrombin receptor. Other data indicate dose-dependent activation of growth cone $cPLA_2$ by another repellent, recombinant SemaIV (FIG. 5). The repellent netrin (recombinant) also stimulates the enzyme, at least weakly.

While much of the AA liberated by $cPLA_2$ is reincorporated into phospholipids in growth cones (Negre-Aminou ct al., 1993), some of it is metabolized by endogenous 12-LOX to 12(S)-HETE. During incubation of growth cones with $^{14}$C-AA (60 min, 37° C.), approximately 5% of the label is converted into 12(S)-HETE, and this is blocked by the LOX inhibitor nordihydroguaiaretic acid (NDGA). More significantly, growth cones increase generation of a compound co-migrating in TLC with 12(S)-HETE and sharing its molecular mass from $^{14}$C-AA-labelled phospholipid 4–8 fold relative to controls when stimulated with thrombin. Consistent with these results, Western blots of growth cone polypeptides probed for leukocyte-type 12-LOX with antibody exhibited a single immunoreactive band. These data indicate that growth cones contain a 12-LOX related or identical to leukocyte 12-LOX, and that stimulation with a repellent such as thrombin actually increases 12(S)-HETE levels in the growth cone.

Figure 7:
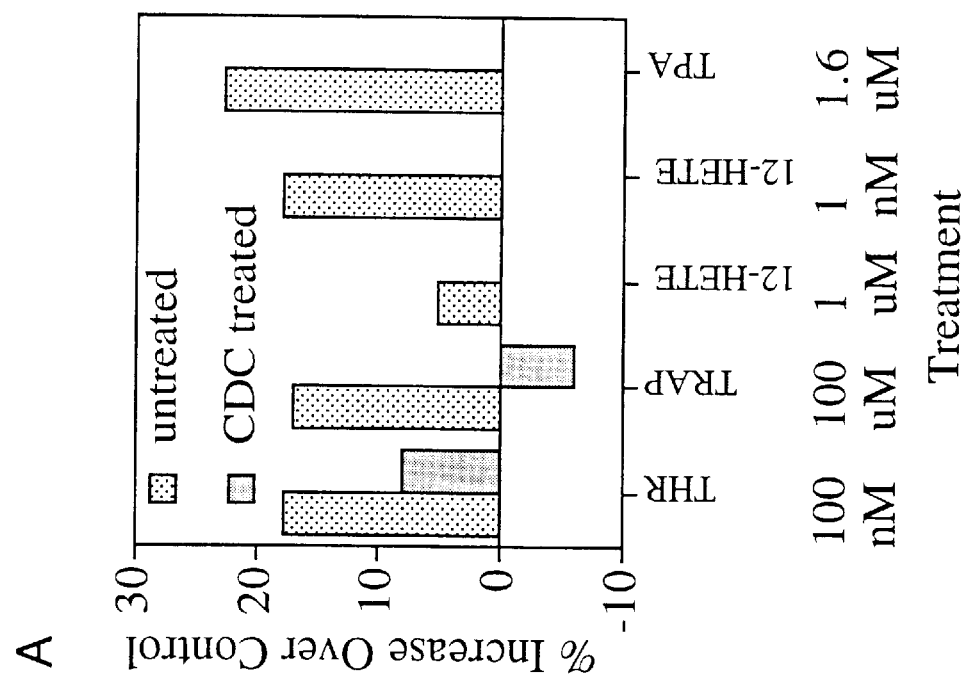
FIG. 7A. Thrombin stimulates MARCKS phosphorylation in a 12-LOX-dependent manner.
FIG. 7B. 12(S)-HETE stimulates MARCKS phosphorylation by PKC in isolated GCPs. Permeabilized GCPs were incubated with $^{32}$P-ATP and different concentrations of 12(S)-HETE or its biologically inactive stereoisomer, 12(R)-HETE, at 30° C. for 30 seconds only. Polypeptides were resolved by SDS-PAGE. MARCKS phosphorylation was quantified by phosphorimaging.

The major putative target of 12(S)-HETE in growth cones is protein kinase C (PKC), which is highly enriched in nerve growth cones. Isoforms of 12(S)-HETE present in growth cone adhesion sites are PKC βI, γ, ε, ι, λ and traces of θ. PKC phosphorylates two major substrates in nerve growth cones, the neuronal protein, GAP43, and MARCKS or the related MacMARCKS (Katz ct al., *J. Neurosci.* 5:1402–1411 (1985); Meiri ct al., *Proc. Natl Acad sci USA* 83:3537–3541 (1986); Skene, *Ann Rev Neurosci* 12:127–156 (1989); and Stumpo et al., *PNAS,USA* 86:4012–4016 (1989)). It was observed that thrombin stimulates MARCKS and GAP43 phosphorylation in isolated growth cones and that this is dependent upon PKC as well as 12-LOX activity (inhibition of these enzymes with calphostin or CDC, respectively, blocks phosphorylation (FIG. 7A). 12(S)-HETE stimulation of PKC in nerve growth cones was also examined. In short time phosphorylation assays (30 sec @ 30° C.), at $10^{-6}$M or less free $Ca^{2+}$, 12(S)-HETE (but not its stereoisomer, 12(R)-HETE) stimulates MARCKS and GAP43 phosphorylation in a dose-dependent, biphasic manner peaking at about $10^{-10}$M (FIG. 7B). Naor et al. *Mol. Endocrinology* 2:1043–1048 (1988) observed a similar, biphasic response of PKC γ to AA, with the peak at 12 μM. The rapid and low-dose response we observe is not compatible with the involvement of a 12(S)-HETE receptor (with a $K_d$ of $10^{-9}$M and requiring 90–120 min for saturation) and of a complex, intervening signaling pathway as suggested by Liu et al., *PNAS, USA* 92:9323–9327 (1995).

The growth cone studies herein indicate that: (a) the repellent thrombin causes $cPLA_2$ activation and growth cone detachment, and (b) that the repellent SemaIV seems to operate through the same pathway as suggested by its strong activation of $cPLA_2$. (c) Thrombin also raises growth cone 12(S)-HETE levels and (d) phosphorylation of MARCKS (and/or MacMARCKS) and GAP43. Furthermore, (e) 12-LOX and PKC activity are necessary and (f) 12(S)-HETE sufficient for the repellent effect.

Figure 10:
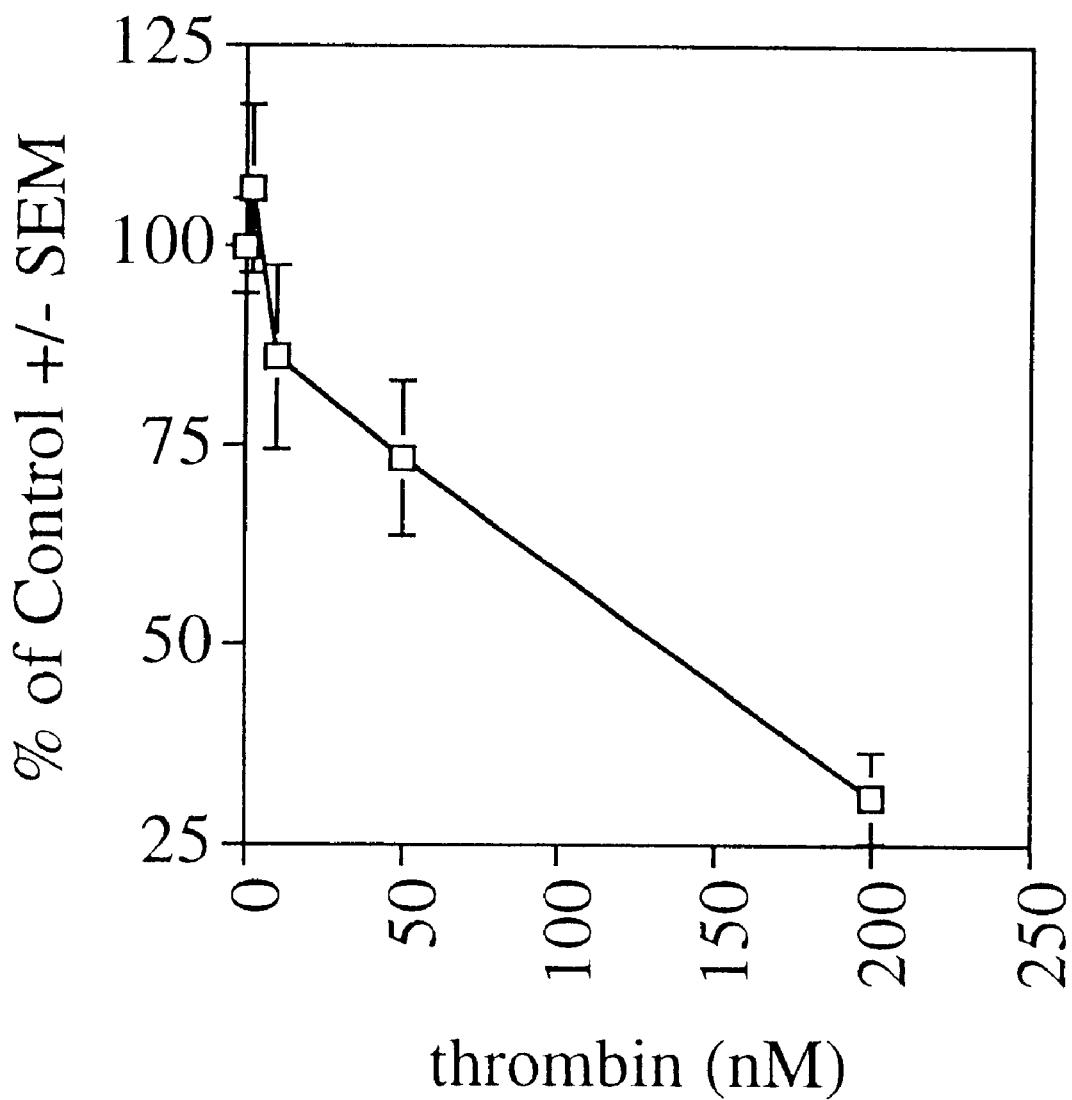
FIG. 10. Dose response of thrombin inhibition of cell motility. Boyden chamber assays were run for 4 hrs in serum-free medium, with different concentrations of rat thrombin in the lower well. Thrombin at 200 nM almost completely suppresses cell migration across the membrane.

Dunning MAT-Lu cells exhibit a highly motile phenotype as mentioned above. In Boyden chamber assays (migration across a laminin-coated membrane with 8-μm pores over a 4 hr period), MAT-Lu cells readily cross the barrier, and this is enhanced about 1.8-fold by IGF-1 in the lower chamber. Control motility and positive chemotaxis to IGF-1 are inhibited by thrombin added to the lower chamber (Table 1 and FIG. 10). When thrombin is added to the cells in a regular culture dish, pseudopods are seen to retract within 5–10 min. Thus, thrombin (at the concentrations used) acts on these cells' pseudopods as a negative-clemotactic or repellent factor. The cells are plated in culture dishes in the presence of serum. Several hours later medium is replaced by serum-free medium. Putative repellent factors, such as thrombin, are added and the cultures incubated for 5–10 min. The cultures are then examined in the inverted microscope and compared to control cultures. Cells are photographed and the photographs digitized, or they are digitized directly, and the stored images are analyzed by measuring pseudopod lengths between their tips and the nucleus (see FIG. 14). This pseudopod retraction assay can be used to screen for repellents and negative-chemotactic actors that may be anti-metastatic factors.

TABLE 1

Effects of IGF-1 and Thrombin on Cell Migration*

|  | Control | IGF-1 (0.75 nM) |
|---|---|---|
| Control | 99.8 +/− 5.9 | 184 +/− 15 |
| Thrombin (200 nM) | 30.9 +/− 5.7 | 38 +/− 9.2 |
| CDC (126 nM) | 97.5 +/− 11.0 | 118 +/− 10.4 |
| Thrombin + CDC | 107 +/− 22.0 | Not done |

*Mat-Lu cells crossing filter in % of control +/− SEM

Figure 8A:
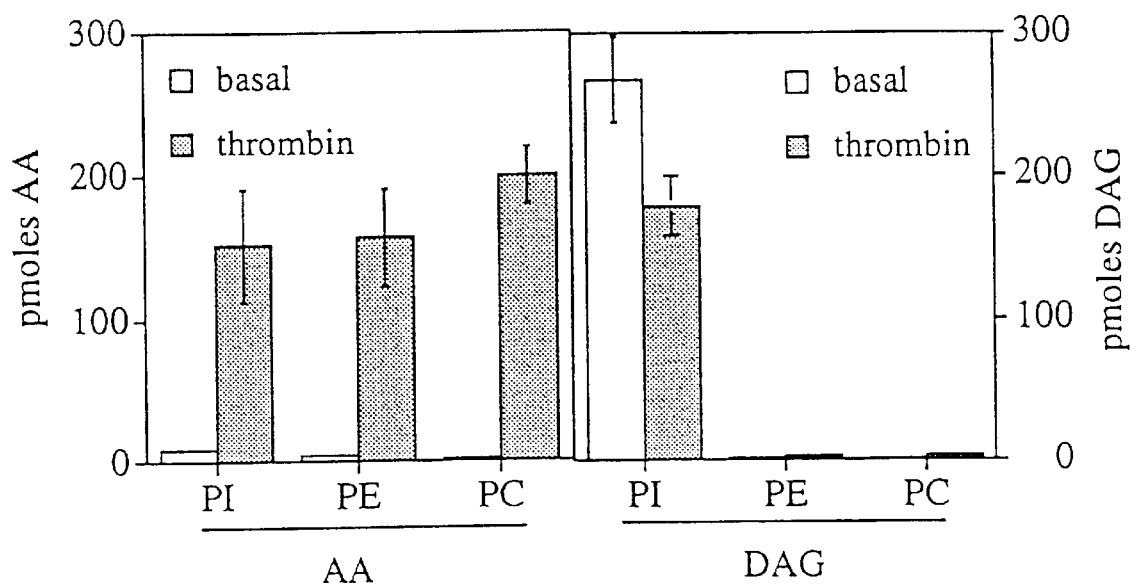
FIGS. 8A–8C. Thrombin activation of phospholipases in MAT-Lu cells. A shows the release, in the presence or absence of 200 nM thrombin, of AA (phospholipase A$_2$ activity) and of diacylglycerol (DAG; phospholipase C activity) from $^{14}$C-AA-labeled phosphatidyl-inositol (PI), -ethanolamine (PE) or -choline (PC) used as substrates. B shows thrombin-stimulated (200 nM) phospholipase A$_2$ activity as fold increase above control, in the presence or absence of the reducing agent dithiothreitol (DTT), which inactivates secreted but not cytosolic enzyme, for the three substrates. C shows the dose response of phospholipase A$_2$ activation by thrombin, as AA release from PE.
Figure 8B:
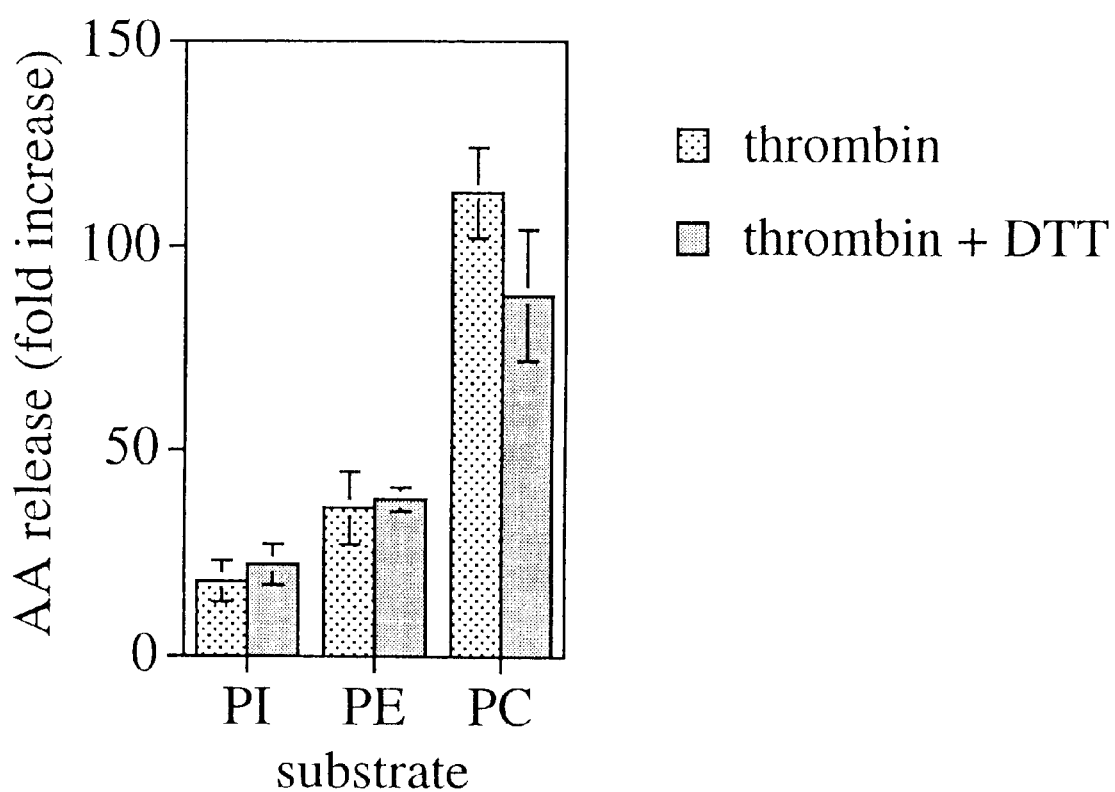

When cytosolic or membrane fractions of MAT-Lu cells are assayed for $cPLA_2$ activity (using $^{14}$C-AA-labeled PC, PE or PI as substrates), AA release from PE is readily measurable whereas PC and PI are poor substrates. In the prostate, most AA appears to be in PE (Pulido et al. 1986). In 10-min assays, exposure of MAT-Lu cells to thrombin (200 nM) increases $PLA_2$ activity ) about 20-fold if PI is used as a substrate, about 50-fold if PE is the substrate, and about 100-fold for PC as the substrate (FIG. 8). The activity is resistant to reducing agents and, therefore, not a secreted $PLA_2$ (FIG. 8B). Because of the substrate selectivity, the $cPLA_2$ is not $cPLA_2$-85 but a different enzyme or a combination of different enzymes similar to those discovered in growth cones (Negre-Aminou et al., 1996). Recombinant SemaIV, the putative tumor suppressor described in Roche et al., Oncogene 12: 1289–1297 (1996), also increases $cPLA_2$-PE activity several fold, in a dose-dependent manner, and also causes pseudopod retraction in MAT-Lu cells. Therefore, thrombin and SemaIV stimulate $cPLA_2$ and pseudopod detachment/retraction in these cancer cells.

Figure 11A:
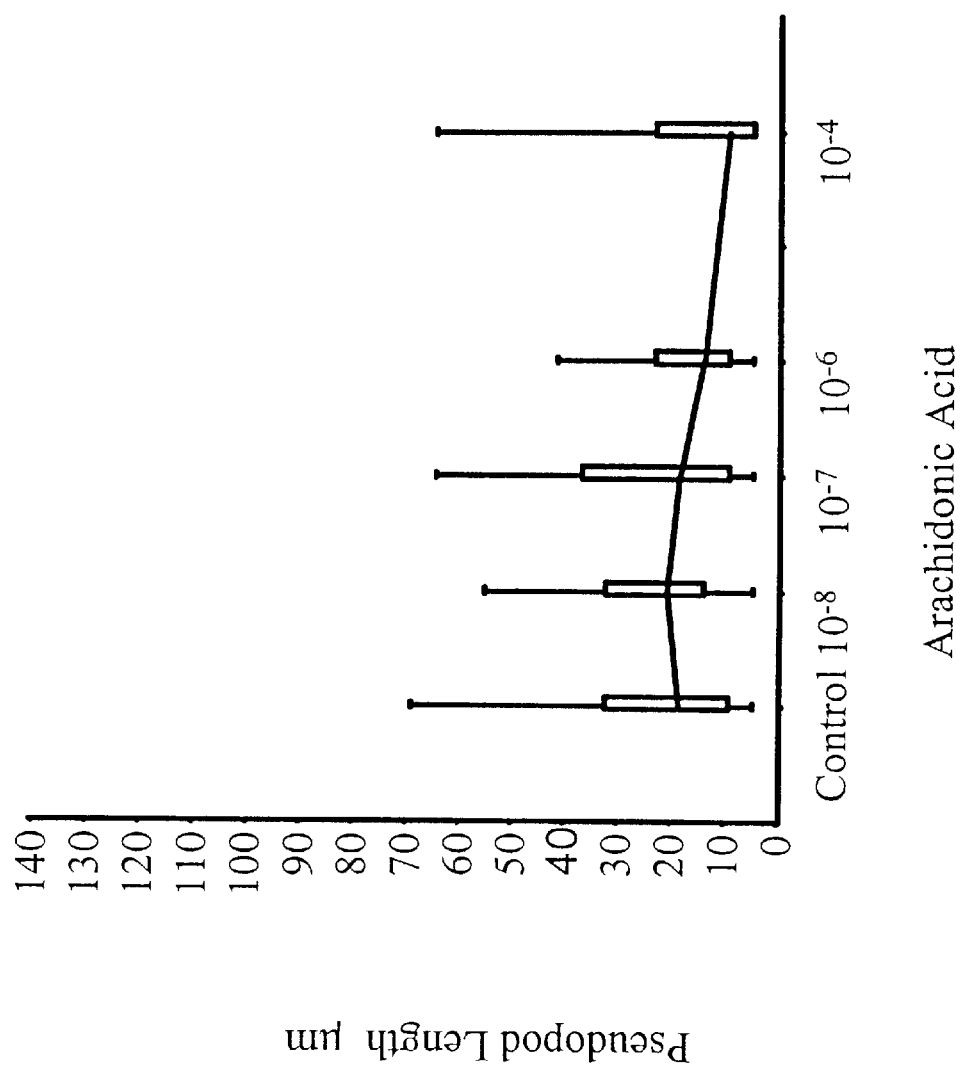
FIGS. 11A–11B. Whisker-box plots of MAT-Lu pseudopod lengths (measured from the center of the nucleus to the end of each pseudopod) after 15 min exposure to different concentrations of arachidonic acid (FIG. 11A) or to $10^{-4}$ M AA with or without pretreatment with the 12-lipoxygenase inhibitor CDC (FIG. 11B). In these plots the center points of each bar indicate the median, the ends of the boxes the 25% and 75% quantiles, and the ends of the whiskers the 5% and 95% quantiles. AA causes statistically significant pseudopod shortening, which is reversed to control levels by CDC. Plots were generated from the type of raw data shown in FIG. 14.
Figure 11B:
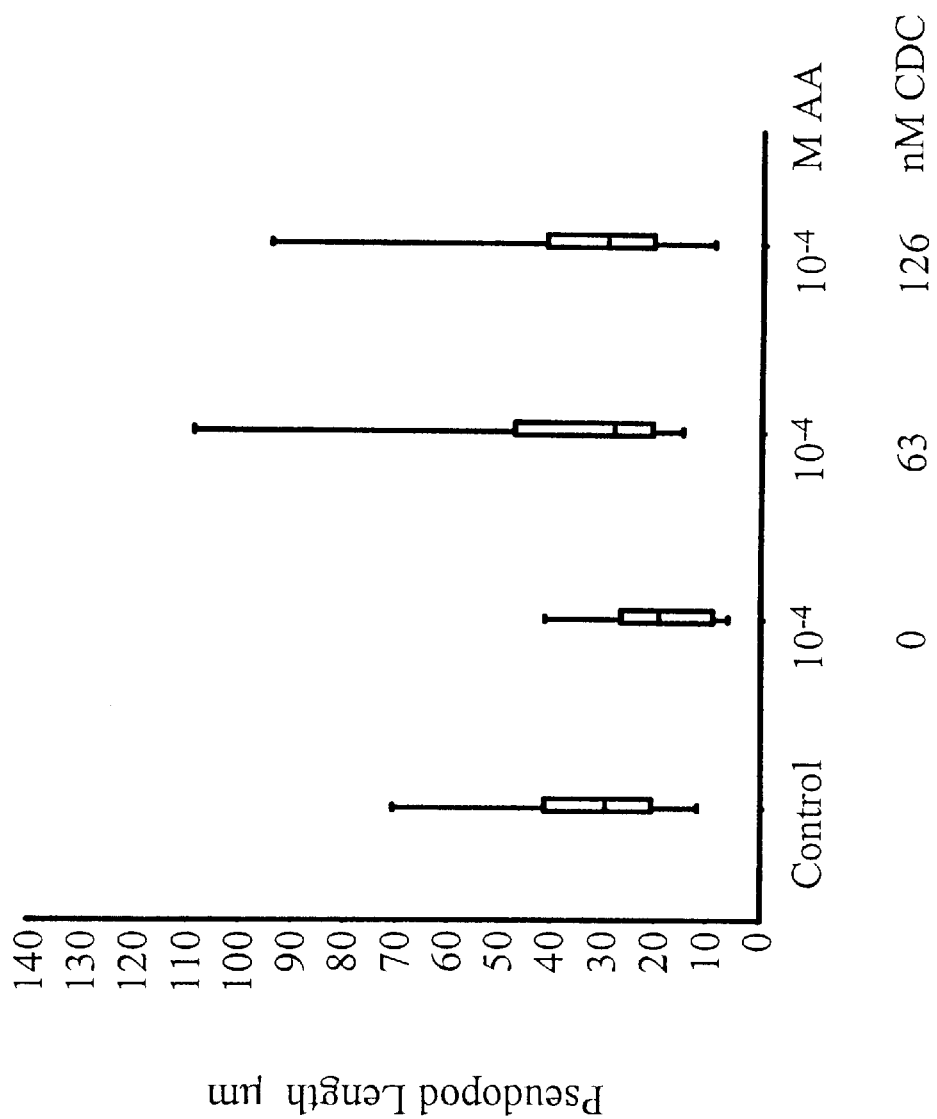

Experiments were conducted to determine the effects of free AA and its metabolites (eicosanoids) on MAT-Lu pseudopods. Because these agents are unstable, pseudopod length measurements were performed after short incubations, rather than Boyden chamber assays. Typically, cells were exposed to AA or eicosanoid (with or without inhibitor) for 15 min and then digitally imaged (see above). Pseudopod lengths were measured and their distribution (in μm) subjected to population analysis (expressed, e.g., as quantiles in Whisker-Box plots). Micromolar AA (but not stearic acid used as a control) caused significant but reversible reduction of pseudopod length (FIG. 11A). The cyclooxygenase inhibitor, indomethacin, did not influence the AA effect, but the lipoxygenase inhibitor, nordihydroguaiaretic acid (NDGA), and the more selective 12-LOX blocker, cinnamyl-3,4-dihdroxy-α-cyanocinnamate (CDC) described in Cho et al., *J Med Chem* 34: 1503–1505 (1991), blocked the AA effect completely (FIG. 11B). In fact, at the $IC_{50}$ or above, CDC seemed to cause pseudopod elongation. This pointed to an important role of 12-LOX and 12(S)-HETE in the observed phenomenon.

Results from Western blots of cultured MAT-Lu cells are consistent with this conclusion. Cultured MAT-Lu cells were harvested, solubilized and the proteins resolved by SDS polyacrylamide gel electrophoresis. Blots of these polypeptides were probed with an antibody to leukocyte 12-LOX, provided by Dr. C. Funk, University of Pennsylvania. The blots revealed a single, prominent band of the appropriate $M_r$ (75,000 Da) indicating the presence of this enzyme.

Figure 16:
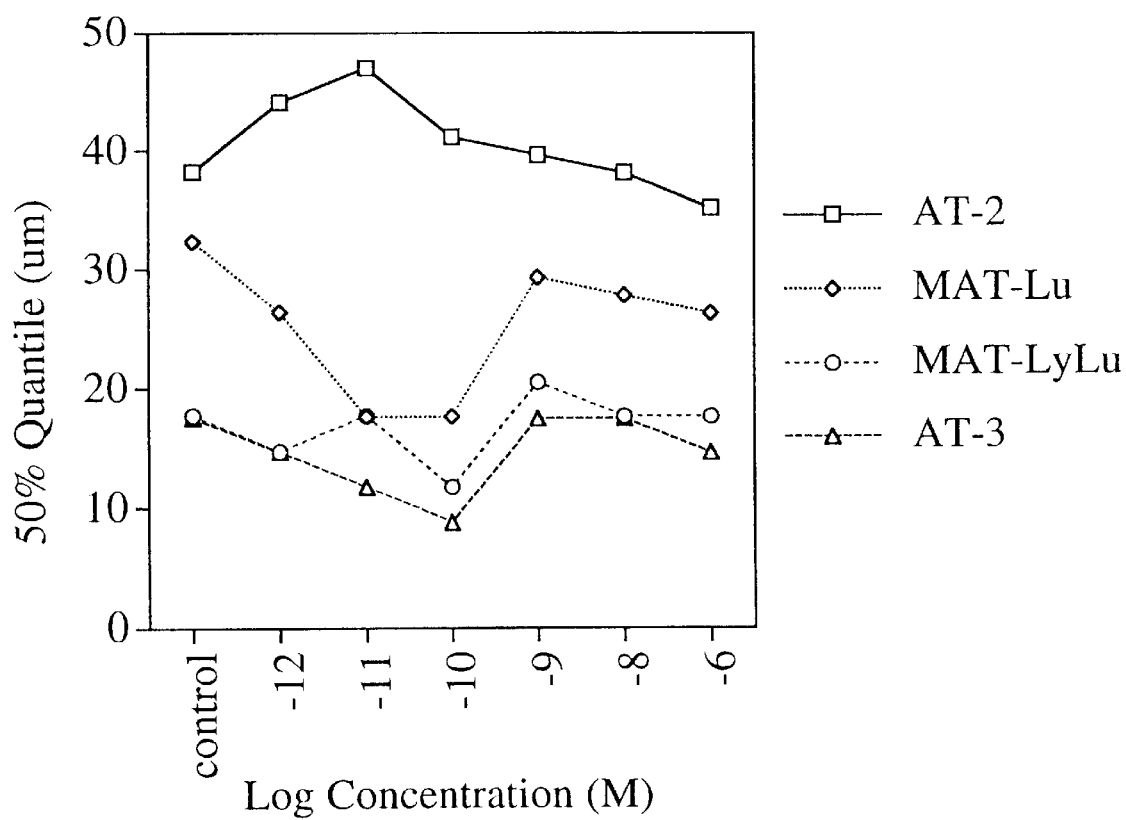
FIG. 16. 12(S)-HETE effect (15-min incubation) on the pseudopod lengths of low-motility (AT-2) and high motility (MAT-Lu, MAT-LyLu and AT-3) Dunning carcinoma cells. 50% quantiles are plotted. Note the different responses of the two classes of cells FIG. 17. Quantitative analyses of growth cone collapse induced by thrombin, TRAP or 12(S)-HETE, with or without CDC pretreatment. Collapse status was assessed on fixed neural cultures having undergone the following treatments: Control, vehicle alone; thr, thrombin (100 nM) for 7 minutes; thr/CDC, CDC (10 µM) pretreatment for 30 minutes, followed by thrombin (100 nM) for 7 minutes; TRAP (100 mM) for 7 minutes; TRAP/CDC, 30 minutes CDC (10 µM) pretreatment followed by TRAP (100 mM) for 7 minutes; 12(S)-HETE ($10^{-7}$ M) for 10 minutes. For each condition at least 50 growth cones were scored as described in Methods. Data were obtained from at least 2 independent experiments and are presented as percent of total growth cones observed.
Figure 18:
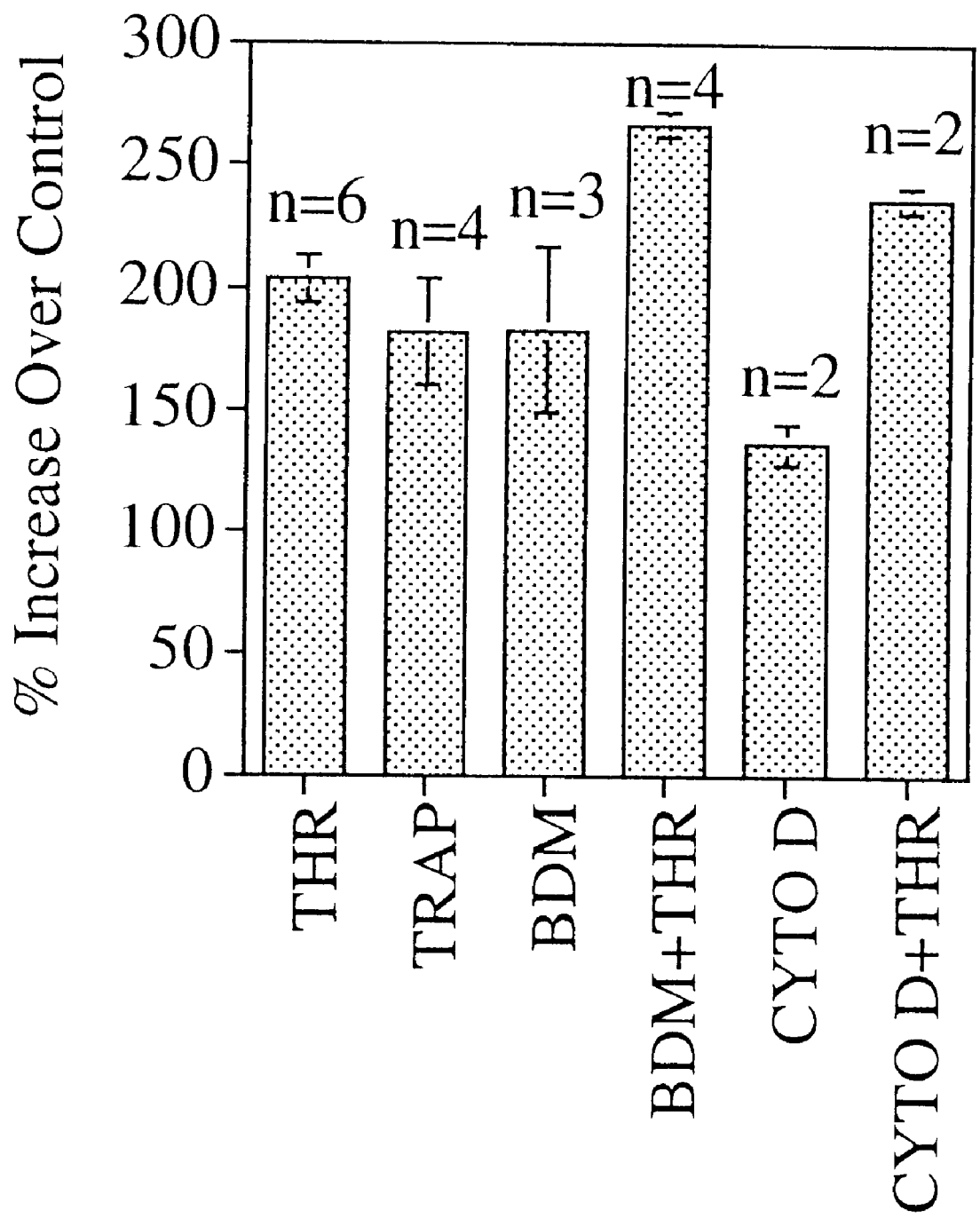
FIG. 18. Thrombin-induced detachment of GCPs from a laminin substratum. GCPs plated on laminin were exposed for 20 minutes to different concentrations of thrombin, with or without cytochalasin D (CD) pretreatment, or to TRAP. Detachment was measured as percent of pelletable protein collected in the supernatant. In control conditions detachment was 17 percent of total GCPs plated. Data shown are increases in detachment relative to control incubation.

The effects of 12(S)-HETE on MAT-Lu pseudopods are shown in FIGS. 16 and 18. The length of these pseudopods is sensitive to 12(S)-HETE. The dose-response is biphasic with a peak of pseudopod detachment and retraction between $10^{-10}$ and $10^{-11}$M. This phenomenon mirrors the MARCKS phosphorylation response observed in isolated growth cones (FIG. 7B). The isomer 15(S)-HETE was about as active as 12(S)-HETE, but 12(R)-HETE, the stereoisomer of 12(S)-HETE, and 5(S)-HETE were essentially inactive between $10^{-10}$ and $10^{-6}$ (FIG. 12). The effective 12(S)-HETE concentrations and the time necessary to see a response in our experiments were well below the $K_d$ ($10^{-9}$ M) and the saturation time (90–120 min) for the putative 12(S)-HETE receptor reported by Herbertsson and Hammarstrom, *FEBS Lett* 298:249–252 (1992) and Liu et al. (1995). Except for two papers which describe effects of $10^{-10}$ to $10^{-8}$ 12(S)-HETE on neutrophil motility (Goetzl et al., *J clin Invest* 59:179–183 (1977) and Yoshino ct al., *Gen Pharmac* 24:1249–1251 (1993), most or all published studies with this eicosanoid have been performed at much higher concentrations so that the effects reported here were not observed. The 12(S)-HETE effect is PKC-dependent. Preincubation of cultured cells with the PKC inhibitor, calphostin, not only blocks pseudopod retraction normally caused by $10^{-10}$ 12(S)-HETE, it seems to result in pseudopod elongation (FIG. 12D), as determined in the pseudopod length assay.

These observations support that thrombin-elicited pseudopod detachment and retraction of a highly motile cancer cell line are mediated b cPLA$_2$, eicosanoid production, activation of PKC, and phosphorylation of MARCKS (see FIG. 2).

EXAMPLE 4

The Signaling Cascade and its Modulation in Other Cancer Cell Lines

Figure 13:
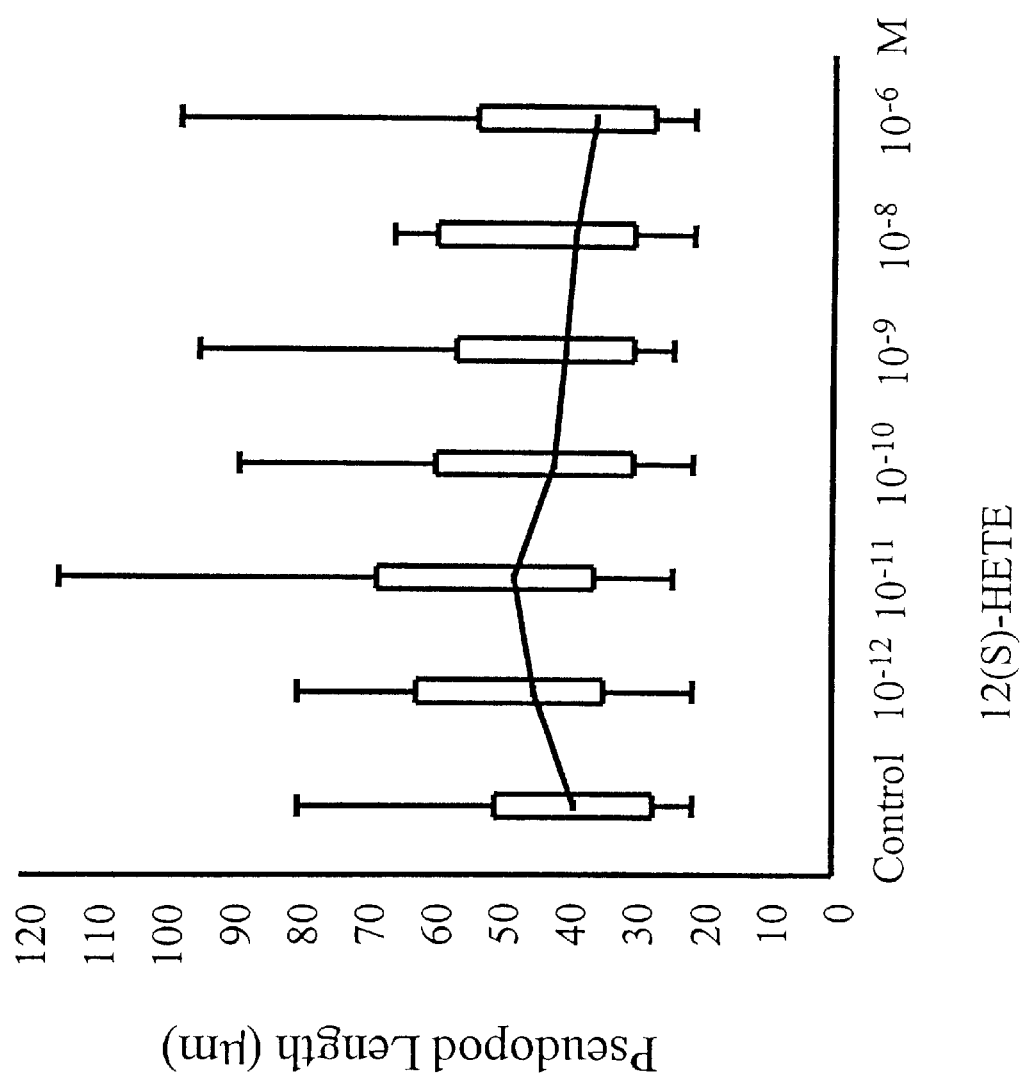
FIG. 13. Pseudopod lengths of AT-2 cells incubated for 15 min at 37° C. in different concentrations of 12(S)-HETE. The Whisker-Box plots show quantiles of pseudopod length; vertical lines, 5 and 95% quantiles; boxes, 25 and 75% quantiles; connecting line, 50% quantile. Note the differences between this dose-response curve and that for MAT-Lu cells, shown in FIG. 12A.

The cascade is compared in detail in four Dunning carcinoma cell lines of different motility: AT-2 (low) versus AT-3. MAT-LyLu and MAT-Lu (high). Based on their behavior and growth pattern in culture and, where available, on the results of Boyden chamber assays, AT-2 cells are much less motile than the other cells. Thrombin stimulated cPLA$_2$ 40–50-fold in MAT-Lu and about 30-fold in AT-2 cells (FIGS. 8 and 9), when PE was the substrate. For the substrates PI and PC the stimulation of cPLA$_2$ was even greater in AT-2 than in MAT-Lu cells, over 100-fold. This indicated that AT-2 cells contain the thrombin receptor, the signaling mechanism regulating cPLA$_2$, and the appropriate forms of activatable cPLA$_2$. However, AT-2 cells essentially did not respond to thrombin in the pseudopod retraction assay. Furthermore, AT-2 cells were almost completely insensitive to AA, even at $10^{-1}$M, whereas all three high-motility cell types responded to AA in the manner described for MAT-Lu cells. Regarding 12-LOX, AT-2 and MAT-Lu cells exhibited similar levels of enzyme protein, as determined by Western blot. The pseudopod responses to 12(S)-HETE were of particular interest. As shown in FIG. 16, high-motility cells showed various degrees of pseudopod retraction peaking at $10^{-11}$ to $10^{-10}$M 12(S)-HETE, whereas retraction was not observed in AT-2 (FIGS. 13 and 16). $10^{-11}$M 12(S)-HETE seems to increase pseudopod length in AT-2 cells in the pseudopod length assay. These observations indicated that AT-2 cells are deficient in the signaling pathway leading to pseudopod withdrawal, and that the defect must be distal to the generation of 12(S)-HETE.

Various human prostatic carcinoma (CaP) lines were obtained from Dr. G. Miller. University of Colorado, Denver Colo. (LNCAP, PPC-1, PC3. DU145, TSU-Pr1) and Dr. I. Fidler, M. D. Anderscn, Houston Tex., (PC-3M and PC-3M-MM2) (Table 2). Experiments were designed to determine the validity of some basic observations in these human CaP cells.

The motility of PC-3M-MM2 cells was examined in Boyden chamber assays and thrombin was found to be a potent inhibitor of cell motility (Table 1). The human CaP cells were tested for their pseudopod responses to thrombin and 12(S)-HETE. As indicated qualitatively in Table 2, all cells tested retracted pseudopods in the presence of the two reagents, albeit to different degrees. Stimulation of cPLA$_2$ activity by thrombin was measured in PC-3M-MM2 cells. Resting AA release from PE and PC was found to be quite low, but it was stimulated about 4-fold by thrombin. In contrast, resting levels for PI hydrolysis were much higher but not further stimulated by thrombin. PC-3M-MM2 cells contain about the same, high level of 75-kDa leukocyte-type 12-LOX observed in the other cells tested as determined by Western blot of PC-3M-MM2 polypeptides resolved by gel electrophoresis.

TABLE 2

Human CaP Cell Lines

| Type | Source | Estimated metastatic potential | References | Pseudopod retraction* thrombin | 12(S) HETE |
|---|---|---|---|---|---|
| PC-3 | Bone meta. of prostate | Low | Kaighn et al., 1979 | + | + |
| PC-3M | Sfrmpvs/ | Moderate | Koslowski et al. 1984 | + | + |
| PC-3M-MM2 | Liver meta. of PC-3 2–3 rounds of meta. selection after PC-3M injection | High | Pettaway et al., 1996 | + | + |
| LNCaP | Lymph meta. of prostate adenoca. | Low-moderate | Horoszewixz et al. 1983 | + | + |
| DU 145 | Brain meta. of prostate adenoca. | Moderate | Stone et al. 1978 | + | + |
| PPC-1 | Primary prost. Adenoca. | Low | Brothman et al., 1989 | nd | nd |
| TSU-Pr1 | Lymph meta. of prostate adenoca. | Low-medium | Iizumi et al., 1987 | + | + |

*Microscopic examination:
nd, not done

These experiments demonstrate: (i) the proposed cascade is operational in various motile cancer cells, including human CaP cells, and (ii) it appears differentially modulated in cancer cells of varying motility.

In addition, these results and the data summarized above support the concepts that: (i) growth cone and CaP cell motility is regulated not only by positive-chemotactic factors but also by repellent factors, such as thrombin, SemaIV and netrin; (ii) their inhibition of motility and pseudopod repulsion is mediated by the proposed cascade, and (iii) the signaling pathway seems to change with motility levels and metastatic progression of cancer cells.

The following examples demonstrate that the pseudopod repellent molecules, thrombin and SemaIV, and probably Semaphorin III and netrin, stimulate the signaling cascade and trigger adhesion site disassembly in human CaP cells.

The data demonstrate the existence (inside as well as outside the nervous system) of a mechanism that controls cancer cell motility and neurite growth via the action of pseudopod repellent factors. The following examples set forth the proposed mechanism of action of these factors. Data indicate a critical role for the cPLA$_2$-cicosanoid-PKC cascade, and they suggest adhesion site disassembly as its target. This indicates that pseudopod repellents can act to suppress tumor cell motility and dissemination.

EXAMPLE 5

Analysis of the Repellent-activated Signaling Pathway

The human CaP cell line(s) are analyzed systematically according to the schematic shown in FIG. 2. Repellent activation of $cPLA_2$ (using different substrates, PE, PC or PI), 12-LOX and PKC, in the presence or absence of an inhibitor of the step just upstream of the enzyme of interest, are measured. This gives a detailed view of the biochemical, structural and behavioral responses of CaP cells to repellent factors.

$PLA_2$ stimulation. Using $^{14}C$-AA-PE, -PC or -PI as a substrate, thrombin, SemaIV and netrin activation of the enzyme are measured. For these assays, commercially available thrombin or thrombin-receptor-activating peptide (TRAP) (Sigma, St. Louis, Mo.), recombinant SemaIV provided to us by Dr. H. Drabkin, University of Colorado School of Medicine, recombinant SemaIII provided by Dr. Y. Luo, Exelixis Pharmaceuticals, San Francisco Calif., and recombinant netrin from Dr. M. Tessier-Lavigne, (University of California, San Francisco) are used. Time courses and dose-response curves are generated with the appropriate substrate(s). These assays are carried out according to well-established protocols described in Negre-Aminou et al., 1996, supra, incorporated herein by reference, on cells grown to equal density levels (as determined by protein and DNA content). Some enzyme assays are carried out in the presence of reducing agent, which blocks secreted but not cytosolic $PLA_2$ activity, to exclude potential interference by secreted $PLA_2$. To characterize the stimulated $cPLA_2$ further, cultured cells are homogenized in protease inhibitor-containing buffer, in the presence of 1 mM EDTA or 0.3 mM $Ca^{2+}$, and then centrifuged in order to generate crude membrane fractions and cytosolic extracts. Both of these are analyzed (at equal calcium levels) for $cPLA_2$ activity to determine whether CaP $cPLA_2$ associates with the membrane in a calcium-dependent manner (as seen for $cPLA_2$-85). In separate experiments, enzyme activity is measured in the presence of different concentrations of free calcium to determine whether the enzyme activity is calcium-dependent or not 12-LOX protein and activation. The presence of leukocyte-type 12-LOX in prostate carcinoma (CaP) cells is determined by Western blot, using antibody received from Dr. Colin Funk. University of Pennsylvania. CaP protein is run alongside a standard sample of rat peritoneal macrophages. 12-LOX activity is assayed in two different ways, with $^{14}C$-AA or with $^{14}C$-AA-PE (or -PI or -PC) as substrate. In both cases, the generation of $^{14}C$-labeled 12(S)-HETE is measured, but in the latter case the measured value is a composite of $PLA_2$ and 12-LOX activity. Comparison of the results indicates whether 12-LOX is regulated or constitutively active. After incubation of homogenates of repellent-pre-treated or control cells with the substrate, labeled products are extracted with chloroform according to Salmon and Flower (1982). The extracts are dried and run on thin-layer plates, together with 12(S)-HETE standards. The 12(S)-HETE bands are scraped off and counted in a scintillation spectrometer. Selected samples are processed by "solid phase extraction" on Sep-Pak columns, followed by HPLC as described in Yu and Powell, *Analy Biochem* 226:241–251 (1995), incorporated herein by reference, and counting of the fractions. Absorption peaks are monitored at 237 nm, the maximum absorption of HETEs using an ultraviolet detector with variable wavelength for the HPLC instrument. Alternatively, extracted HETE can be identified and quantified mass spectrometrically. The results are expressed as pmoles lipid messenger synthesized per minute, per mg protein. In experiments involving $^{14}C$-AA-PE (or -PI or -PC) as a substrate, $cPLA_2$ inhibitors also are used. These are: bromoenol lactone (Ackermann et al., *J Biol Chem* 270:445–450 (1995)) or the AA analog $AACOCF_3$ (Street et al., *Biochem* 32:5935–5940 (1993), one of which should block the repellent-stimulated generation of $^{14}C$-AA and of $^{14}C$-12(S)-HETE (the blocker, p-bromo-phenacylbromide, is too non-specific). These experiments indicate (i) that stimulation of CaP cells by the different repellents increases the generation of 12(S)-HETE, as shown for MAT-Lu cells and growth cones and thrombin, and (ii) that this is due to the increased availability of AA and/or increased 12-LOX activity itself. The data generated herein, as well as those in the literature (Shimizu and Wolfe, *J. Neurochem* 55:1–15 (1990)) suggest that generation of AA is the rate-limiting step in eicosanoid production and that 12-LOX is constitutively active rather than being activated by the signaling pathway.

PKC activation. Repellent stimulation of CaP cells increase phosphorylation of endogenous MARCKS or an exogenous substrate, MARCKS phosphorylation site domain (PSD) peptide (commercially available from Calbiochem, LaJolla, Calif.) was determined. CaP cells in culture are pre-loaded with $^{32}P$-orthophosphate and stimulated with different repellent concentrations for different time intervals (0.5 to 10 min). The reaction is stopped and MARCKS extracted with ice-cold acetic acid as described in Robinson et al. *Analyt Biochem* 210:172–178 (1993). Extracted polypeptides are run on SDS-polyacrylamide gels (SDS-PAGE). A MARCKS antibody is used for positive MARCKS identification by Western blot and/or for immunoprecipitation. Attentively, two-dimensional gels, in which MARCKS forms a characteristic triangular and highly acidic spot as described, for example, in Katz et al., *J Neurosci* 5:1402–1411 (1985) can also be used. Phosphopeptide maps of this spot also are generated to ascertain positive identification (Wu et al., *PNAS, USA* 79:5249–5253 (1982): Katz et al., 1985). MARCKS phosphorylation is determined quantitatively in the phosphorimager and expressed based on total cell protein in the assay. Alternatively, CaP cell homogenates are incubated with $^{32}P$-ATP in the presence or absence of repellent. Phosphorylation substrate is endogenous MARCKS or exogenous PSD peptide. The reaction is stopped with ice-cold acid, and the supernatant containing the acid-soluble MARCKS or PSD is analyzed by gel electrophoresis and the phosphorimager. The results indicate (i) whether, (ii) with which time delay and (iii) at which concentration each repellent stimulates PKC activity as determined by MARCKS or PSD phosphorylation. Based on the data obtained on isolated growth cones, a dose-dependent phosphorylation of MARCKS in response to repellent incubation should be found.

These experiments provide quantitative data on the activation of the various steps of the cascade by each of the repellents tested. The inhibitor experiments confirm the dependence of later steps in the cascade on the proposed preceding steps. These biochemical data are correlated with the observations on motility and adhesion site morphology from Example 2.

EXAMPLE 6

Phosphorylation and Adhesion Site Disassembly

This example demonstrates that phosphorylation of MARCKS and its subsequent dissociation from adhesion sites triggers the disassembly of the adhesion site. The analysis of such mechanisms cannot be performed in whole cells. Instead, adhesion site preparations are generated by plating CaP cells on laminin, collagen, fibronectin or other similar substrata prepared by coating culture dishes first with nitrocellulose and then with the substrate protein as described in Lagenaur and Lemmon, PNAS, USA 84:7758–7757 (1987). Such substrata are resistant to detergents including SDS (important for the processing of the samples). After several hours of growth on these substrata at low density, CaP cells are extracted with Triton X-100 (TX100) in order to remove all membrane and soluble proteins that are not attached to the substratum or the cytoskeleton. This procedure leaves adhesion sites intact for biochemical or morphological analysis as described in Rohrschneider, PNAS, USA 77:3514–3518 (1980) and Sobue & Kanda, Neuron 3:311–319 (1989). The biochemical analyses are paired with immunofluorescence localization studies. Adhesion site disassembly is monitored by the release of actin, characteristic adapter proteins (for example, talin, paxillin and vinculin), and integrin with probes that are commercially available.

The first set of experiments is designed to examine PKC activation by 12(S)-HETE. From preliminary studies on growth cones, we know that the TX100-extracted adhesion site preparation retains PKC activity and MARCKS. Because MARCKS availability may be limiting, exogenous PSD peptide is used as a substrate. The adhesion site preparations are washed with buffer and then incubated for different periods with PSD, 12(S)-HETE (or 12(R)-HETE as control) and $^{32}$P-ATP at different, low calcium levels. In parallel experiments, diacylglycerol and AA are used as potential PKC activators, again at different calcium levels. After 10 sec to 1 min at 30° C., the reactions are stopped. The soluble supernatant of the preparation is collected and analyzed by SDS-PAGE and phosphorimaging. Time courses and dose response curves of PSD phosphorylation are analyzed to determine the profile of PKC activation.

12(S)-HETE-stimulated phosphorylation of endogenous MARCKS and its dissociation from adhesion sites also is studied. Adhesion site preparations are incubated as described, but without PSD peptide. The soluble supernatant is collected. The proteins that remain attached to the substratum also are solubilized with SDS. Phosphorylation of MARCKS is determined in both protein preparations. MARCKS is acid-extracted and then run on one- or two-dimensional gels. Alternatively, MARCKS may be immunoprecipitated with antibody, using radio-immunoprecipitation assay (RIPA) buffer (containing TX100, deoxycholate and SDS). Once MARCKS has been identified, further protein analysis is done by SDS-PAGE, if there are no other phosphoproteins seen at that Mw. One or several of these procedures are used to identify MARCKS in the substrate-bound and the supernatant fractions, and its phosphorylation is quantified by phosphorimaging. The data obtained are expressed as $^{32}$p incorporation into MARCKS of each fraction, as a function of 12(S)-HETE concentration. Most phospho-MARCKS is found in the supernatant. Using MARCKS antibody in Western blots allows one to quantify, in the same phosphorylation experiments, the relative distribution of MARCKS protein between the substrate-adherent and the soluble fractions. Western blots of the two fractions are probed with the MARCKS antibody and then an HRP-conjugated second antibody. After visualization of MARCKS, semi-quantitative data can be obtained by densitometry of the blot.

PKC-activation triggering adhesion site disassembly also is examined as indicated by the loss of characteristic adhesion site proteins into the soluble supernatant. PKC in adhesion sites is stimulated (or control incubated), in the presence of unlabeled ATP, with or without an optimal dose of 12(S)-HETE (substitution of 12(R)-HETE or addition of the PKC inhibitor calphostin serve as controls). Substrate-bound and soluble fractions are prepared and processed for Western blot analysis. The blots are probed with antibodies to talin, paxillin and vinculin, which are key components of adhesion sites. Using the semi-quantitative approach described above, the relative amounts of talin, paxillin and vinculin are monitored in the two fractions as a function of (i) 12(S)-HETE concentration in the assay and (ii) incubation time (up to 5 min). Because these experiments are carried out on laminin, collagen, fibronectin or similar substrata) matrices, we predict the involvement of particular integrin subunits (most likely $\beta_1$, but possibly $\beta_4$ for laminin, Albelda, Lab Inves. 68;4–17 (1993)). This is verified by probing first CaP cell membrane preparations and then adhesion site preparations for the presence of integrin $\beta_1$ and $\beta_4$ by Western blot (antibodies available commercially from Chemicon. Temecula, Calif. or Life Technologies/GIBCO-BRL, Gaithersburg, Md.). If PKC-activation triggers adhesion site disassembly, integrins disaggregate and dissociate from their ligands. Therefore, 12(S)-HETE-treated (vs. control) adherent and soluble fractions are examined by Western blot for the presence of integrins. In further experiments, adherent proteins from radio-phosphorylation experiments are solubilized in RIPA buffer, followed by immunoprecipitation of the integrin from this fraction as well as from the soluble supernatant. The immunoprecipitates are resolved by SDS-PAGE and analyzed with the phosphorimager to determine whether PKC activation with 12(S)-HETE also phosphorylates the integrin $\beta$ subunit, and whether this correlates with integrin distribution, between the attached fraction versus the Triton X-100 soluble supernatant.

It is helpful to pair the biochemical experiments with morphological analyses. CaP cells are grown on coverslips coated with laminin, collagen, fibronectin or other similar substrata, subjected for various periods of time to treatment with repellent or 12(S)-HETE and then fixed mildly with a low concentration of formaldehyde. Subsequently cells are permeabilized with TX100 (at a low concentration in order to preserve most of the membranes) to allow for the escape of soluble proteins. Such preparations are quenched with glycine and bovine serum albumin and then processed for immunofluorescence with primary antibody, followed by a tagged secondary antibody. Controls consist of omitting the primary antibody and using instead non-immune serum from the same species. In addition to the antibodies to talin, paxillin, vinculin and integrin $\beta_1$ (or $\beta_4$), MARCKS antibody and fluorescent phalloidin (to label polymerized actin) also are used. Preferably samples are examined by confocal microscopy. When advisable, double-immunofluorescence with phalloidin and differently tagged secondary antibodies are performed. The presence of MARCKS, talin, paxillin, vinculin, actin and the appropriate integrin are studied morphologically in pseudopod attachment sites in control cells and during their changes in response to repellents or 12(S)HETE treatment.

This example provides information about the molecular rearrangements occurring in adhesion sites in response to repellent treatment. As in growth cones, adhesion site PKC in CaP cells also is expected to respond rapidly and in a biphasic manner to very low concentrations of 12(S)-HETE. However, such a response would not exclude intermediate steps between 12(S)-HETE release and PKC activation. A biphasic dose response of PKC to 12(S)-HETE is important for understanding how a particular balance of MARCKS phosphorylation is maintained in the cell during locomotion. The example also demonstrates that phospho-MARCKS dissociates from the adhesion sites, and that this is correlated with, or triggers, the disassembly of the entire adhesion site, including integrin detachment. There may be other substrates of PKC that are important in the phenomenon.

Experiments also are performed to determine whether phospho-MARCKS dissociates from the adhesion sites and whether this is correlated with, or triggers, the disassembly of the entire adhesion site, including integrin detachment.

EXAMPLE 7

Thrombin as a Pseudopod Repellent

In this example, a highly motile cancer cell line with long, almost neurite-like processes, the MAT-Lu subline of Dunning rat prostatic carcinoma was used. We found that thrombin acts as a pseudopod repellent in these cells, and that it is a strong activator of $cPLA_2$. A variety of inhibitor experiments indicate that the generation of 12(S)-HETE as well as the activation of protein kinase C (PKC) are necessary for thrombin's repellent effect. The application of intermediates of the signaling pathway, such as AA or 12(S)-HETE, to the cells indicate that these reagents are sufficient to cause pseudopod detachment and retraction. Therefore, the present example relates to the signaling pathway that links pseudopod detachment and retraction to thrombin receptor activation.

Cell Culture. MAT-Lu cells were grown in RPMI 1640 cell culture medium (e.g., Sigma) containing 10% heat-inactivated fetal bovine serum, 2 mM L-glutamine, 100U/ml each of penicillin and streptomycin, and 250 nM dexamethasone, in 5% $CO_2$ in air at 37°, as described by Isaacs et al. (1986). Cells were monitored morphologically to ascertain the constancy of the phenotype.

Boyden Chamber Motility Assays. Disposable transwells (Coming Costar, Cambridge, Mass.) of 6.5 mm diameter and 8 μm pore size were coated with 5 μg/ml laminin on both sides. The membranes were washed twice with Hank's balanced salt solution (HBSS) and then pre-incubated with growth medium containing 10% fetal bovine serum. Trypsinized cells ($5\times10^4$) were plated into the upper well. After 1 hour the upper chamber was washed twice with HBSS, filled with serum-free medium and moved to a new lower chamber, also filled with serum-free medium, with or without thrombin and/or 0.75 nM insulin-like growth factor-1 (IGF-1).

After incubation for 4 hrs, cells on the membrane were fixed and stained with a Diff-Quick kit (Baxter Scientific Products). Cells on the upper side were scraped off, the membranes were removed, mounted onto microscope slides and analyzed. Each filter was scanned twice at right angles under the light microscope with a 16xphase contrast objective lens. A continuous series of 20 frames for each filter was digitized using a high-resolution CCD camera (Kodak) and stored in a Power Macintosh computer. The two most peripheral pairs of frames from each scan were deleted so that 12 frames were analyzed for each filter. Cells that had crossed the membrane were counted and tabulated. The sum of the cells counted in the twelve frames was an individual data point.

Pseudopod Morphometry. To study the effects of various agents on pseudopods on a short-term basis, we measured pseudopod lengths. Cells plated in 35-mm diameter dishes at low density ($1\times10^4$ per dish) were incubated overnight, tie medium was changed, and the experiments were run four hours later. First, cultures were shifted to serum-free medium, which was replaced one hour later by serum-free medium with or without the various agents (thrombin, AA or HETEs). Care was taken to avoid heat and light inactivation of the eicosanoids. Culture dishes were placed on a Zeiss inverted microscope equipped with a heated stage and viewed with a 16xphase contrast objective lens. Randomly selected fields of the cultures, containing generally about 20 cells each, were recorded, digitized and stored in the computer at the onset of the experiment and at different times thereafter.

In some cases, individual cells were monitored over different periods of time immediately after introduction of the reagent, either by mixing it into the medium or by applying it locally to one end of the cell. Local application was done with a "puffer" system that expels microliter amounts of the desired solution from a micromanipulator-controlled micropipette tip. Cell morphology was recorded, and the captured images were analyzed with a Power Macintosh computer using NIH Image. Cell process length was measured from the center of the nucleus to the end of the process. Characterization of the frequencies of pseudopod lengths, at a fixed time for each of a sequence of concentrations of reagent, utilized a gamma regression model with an inverse quadratic linear predictor (McCullagh and Nelder, *Generalized Linear Models* 2d ed., pp. 291–292 (Chapman & Hall, 1989), separately fit to each concentration data set. Although no formal goodness-of-fit tests were carried out, in virtually every case there was good visual representation of the pattern of response (see FIG. 14). Most data, however, are shown as whisker-box plots, where the center point represents the 50%, the ends of the box the 23% and 75%, and the "whiskers" the 5% and 95% quantiles (e.g., FIG. 11). Statistical comparisons of pseudopod lengths for different treatments were done by standard non-parametric techniques (Wilcoxon Rank Sum or Kruskal-Wallis Tests), as judged appropriate. Polynomial curve fittings were done by standard least-squares techniques. Statistical analyses and graphing were done with the use of SAS procedures: Reg, Phreg, Nparlway and Plot (SAS institute Inc., Cary, N.C.).

Biochemical Assays. MAT-Lu cells were plated at a density of $0.5\times10^6$ cells per flask (T-75) and grown as detailed above to approximately 25% confluency. On the day before the experiments, the serum level in the medium was dropped to 1%. Cells were fed with fresh 1% serum-medium 4 hrs prior to harvest. For harvesting, cells were rinsed with $Ca^{++}$,$Mg^{++}$-free HBSS, covered with 2 ml cold $Ca^{++}$-free modified Krebs buffer (220 mM sucrose, 50 mM NaCl, 5 mM KCl, 22 mM HEPES, 10 mM glucose. 1.2 mM $NaH_2PO_4$ and 1.2 mM $MgCl_2$, pH 7.3), and placed on ice. Cells were scraped off, pelleted for 5 min at 200 rpm and re-suspended in a minimal volume of Krebs buffer. Aliquots were used to determine protein concentration (Biorad Assay) and phopholipase activity. To measure $PLA_2$ activity 10–12 μg of cell protein was incubated with or without thrombin for 10 min on ice, $^{14}$C-AA-labeled phospholipid substrate (7 μM. 40–60 mCi/mmol) was added, and the mixture was transferred to 37° for 20 min. The reaction was stopped by adding cold cliloroform/methanol (1:2 v/v). Lipid extraction followed by thin-layer chromatography (Negre-Aminou et al., *J Neurochem* 67:2599–2608 (1996)) isolated the reaction product (identified by co-migration with AA standard), which was then scraped off the plates and analyzed in a scintillation spectrometer (Beckman). In some experiments, especially those involving $^{14}$C-AA-phosphatidylinositol as substrate, the diacylglycerol-containing band (identified by co-migration of standard) also was scraped and counted in order to measure phospholipase C (PLC) activity.

The generation of 12(S)-HETE in MAT-Lu cells in response to thrombin was assayed in cells cultured and harvested as just described. Ten to twenty mg cell protein was incubated with or without thrombin for 10 min on ice, $^{14}$C-AA-labeled phospholipid or $^{14}$C-AA was added as substrate, and the mixture was transferred to 37° for 10 or 20 min. The reaction was stopped by the addition of ice-cold chloroform. Lipid extraction followed by thin-layer chromatography or HPLC isolated the reaction product [12(S)-HETE], identified by co-migration of standard.

Cell Motility. MAT-Lu cells are highly motile (Isaacs et al., 1986). They immediately spread over the culture dish rather than forming clonal colonies. Boyden chamber assays quantify motile behavior by measuring the number of cells that migrate through the pores of a membrane within a specific period of time (Boyden, 1962). The laminin-coated filters in our assays had relatively large, open pores (8 $\mu$m) so that proteolysis of extracellular matrix was not necessary for crossing the membrane. IGF-1, which is a positive chemotactic factor for many cell types increases MAT-Lu migration by about 80% in four-hour assays (Table 1). Thrombin, in contrast, inhibits both control and IGF-1-induced migration across the membrane in a dose-dependent manner (FIG. 10), resulting in a 70–80% decrease (at 200 nM). Thus, thrombin acts as a negative chemotactic factor for MAT-Lu cells.

Because of the involvement of HETEs in the mechanism of thrombin action, Boyden chamber assays also were performed with thrombin in the presence of the LOX inhibitor, cinnamyl-3, 4-dihydroxy-alpha-cyanocinnamate (CDC). At 63 nM ($IC_{50}$) and at 126 nM CDC inhibits 12-LOX selectively (Cho et al., 1991). Table 1 shows that CDC reverses the effect of thrombin.

Effects of Thrombin and Eicosanoids on Pseudopod Length. Boyden chamber assays cannot produce short-term data on motility mechanisms. Therefore, morphometric assays were used to observe cellular effects immediately after addition of a reagent. In these assays, thrombin (200 nM) caused pseudopod shortening in MAT-Lu cells within minutes of administration. Typically, the cell processes are seen to retract slowly, with persisting knob-like enlargements at their tips. The withdrawing pseudopods frequently are curvilinear, indicating that they are not under tension. These morphologies suggest that distal pseudopod detachment is the primary event of thrombin-induced process retraction. The phenomenon of pseudopod withdrawal is reversible after thrombin removal.

The effects of AA, a potential mediator of thrombin action, also were investigated. Exogenous AA in the micromolar range (but not other fatty acids, such as stearic and linoleic acid) mimics the thrombin-induced length reduction within a similar time frame (FIG. 15A; 15 min). A linear regression of response data points across the logs of AA doses yielded a significant (p<0.002) slope of -1.26.

A 15-min pretreatment with the cyclo-oxygenase inhibitor, indomethacin (10 $\eta$m), had no effect at all on AA-induced pseudopod shortening. However, nordihydroguiaretic acid (NDGA), which blocks LOXs nonselectively at 25 $\mu$M, and CDC did interfere with the AA effect. By itself the less specific NDGA (25 $\mu$M; 15 min pretreatment) had no effect on pseudopod lengths, but it inhibited the pseudopod shortening observed at $10^{-1}$ M AA so that control and AA+NDGA samples were not significantly different (p>0.75). FIG. 15B shows the results obtained with CDC, which is selective for 12-LOX. At 63 nM ($IC_{50}$) and at 126 nM, CDC pretreatment (15 min) reversed the AA effect so that controls and AA+CDC samples were indistinguishable statistically (whereas the values for AA alone were significantly lower, at p<0.01). These results suggest the involvement of 12-LOX in the retraction phenomenon. Therefore, subsequent experiments were focused on the 12-LOX product of AA, 12(S)-HETE.

The general or localized application of 12(S)-HETE to MAT-Lu cells in culture was examined. Microliter amounts of 12(S)-HETE ($10^{-10}$M) released into the medium about 10 $\mu$m away from a particular cell process, resulted in the onset of pseudopod detachment and shortening within 1 min. After about 15 min, the pseudopod became absorbed completely into the cell, and several times the emergence of a new pseudopod was observed on the opposite pole. If 12(S)-HETE ($10^{-10}$M) was applied by medium replacement, pseudopod shortening was nearly complete for most cells within about 15 min. The observed morphologies were the same as those for thrombin. Thirty minutes after withdrawal of 12(S)-HETE by medium replacement (done 30 min. after onset of the experiment), pseudopods had reappeared indicating reversibility of the eicosanoid effect.

Figure 12A:
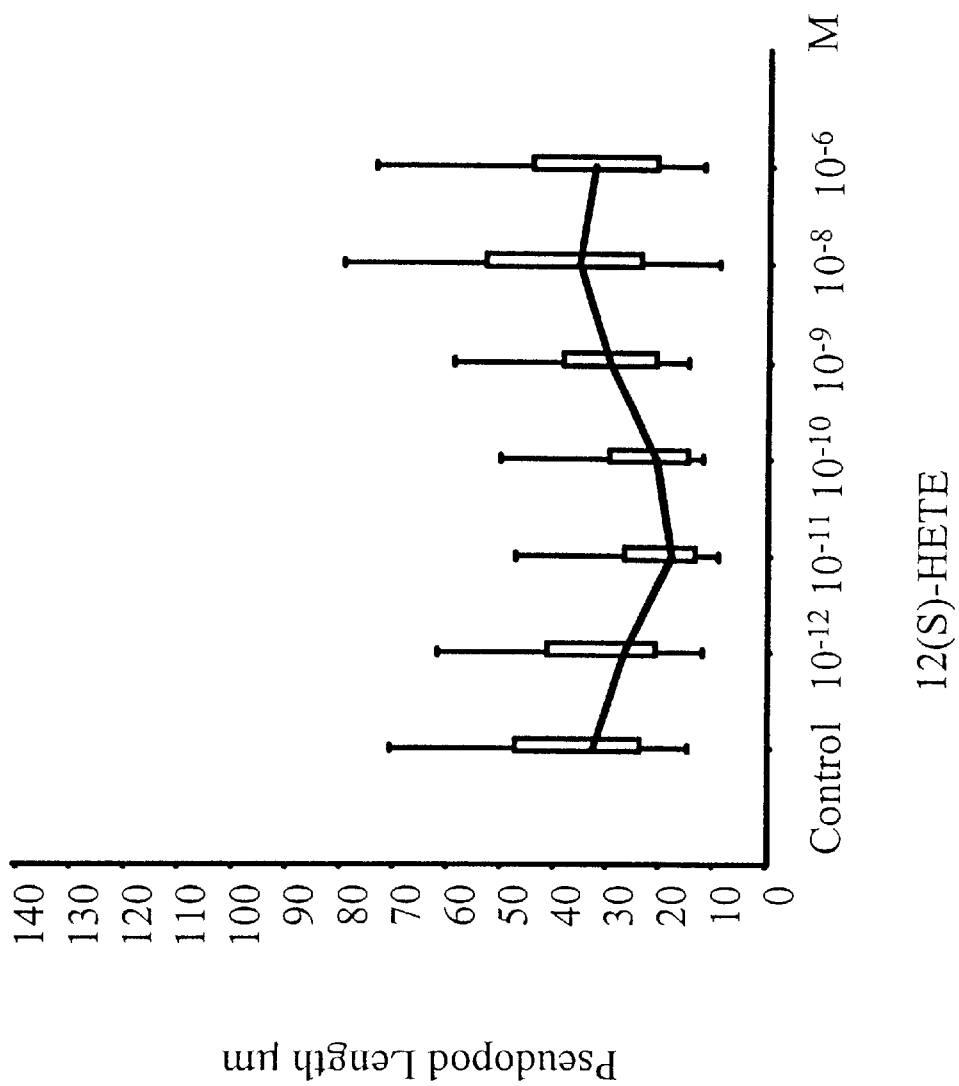
FIGS. 12A–12D. Whisker-box plots of pseudopod lengths of control cells and cells exposed for 15 min to different concentrations of various HETE isomers (A,B,C).
Figure 12B:
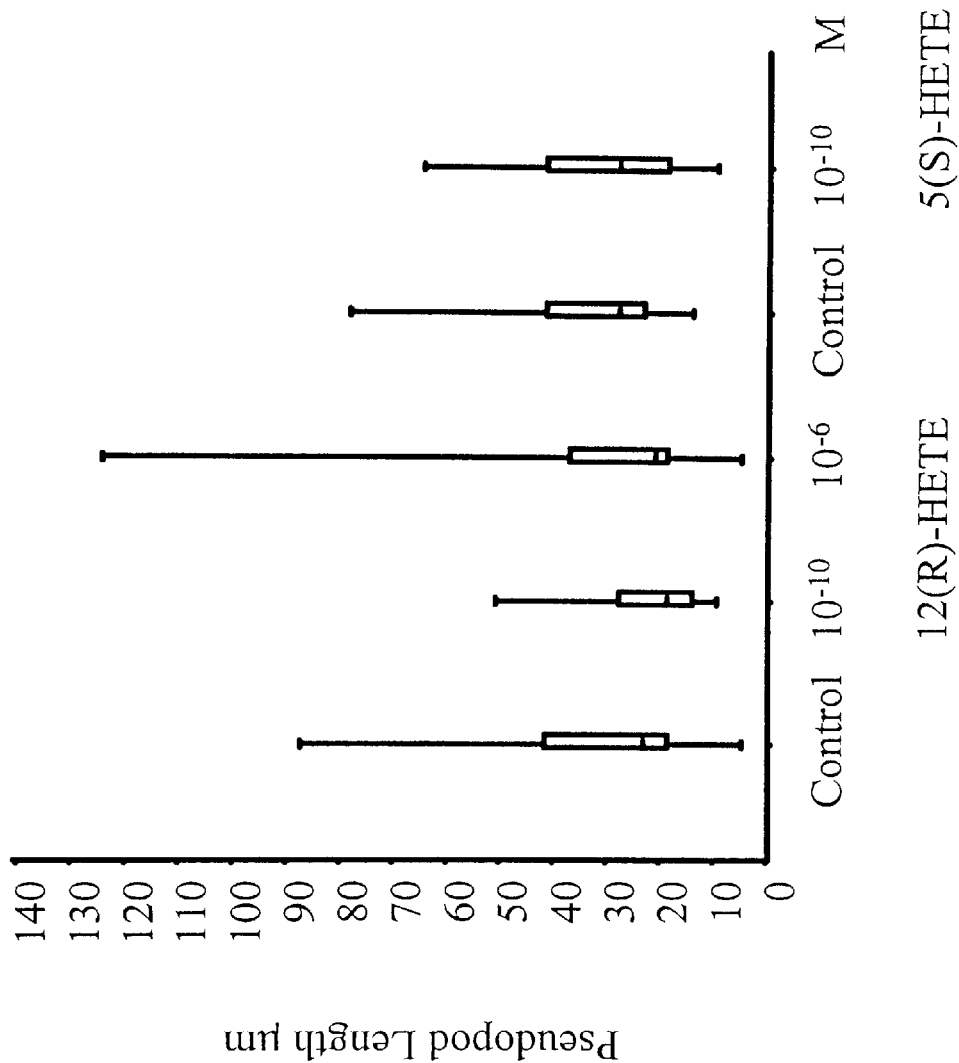
Figure 12C:
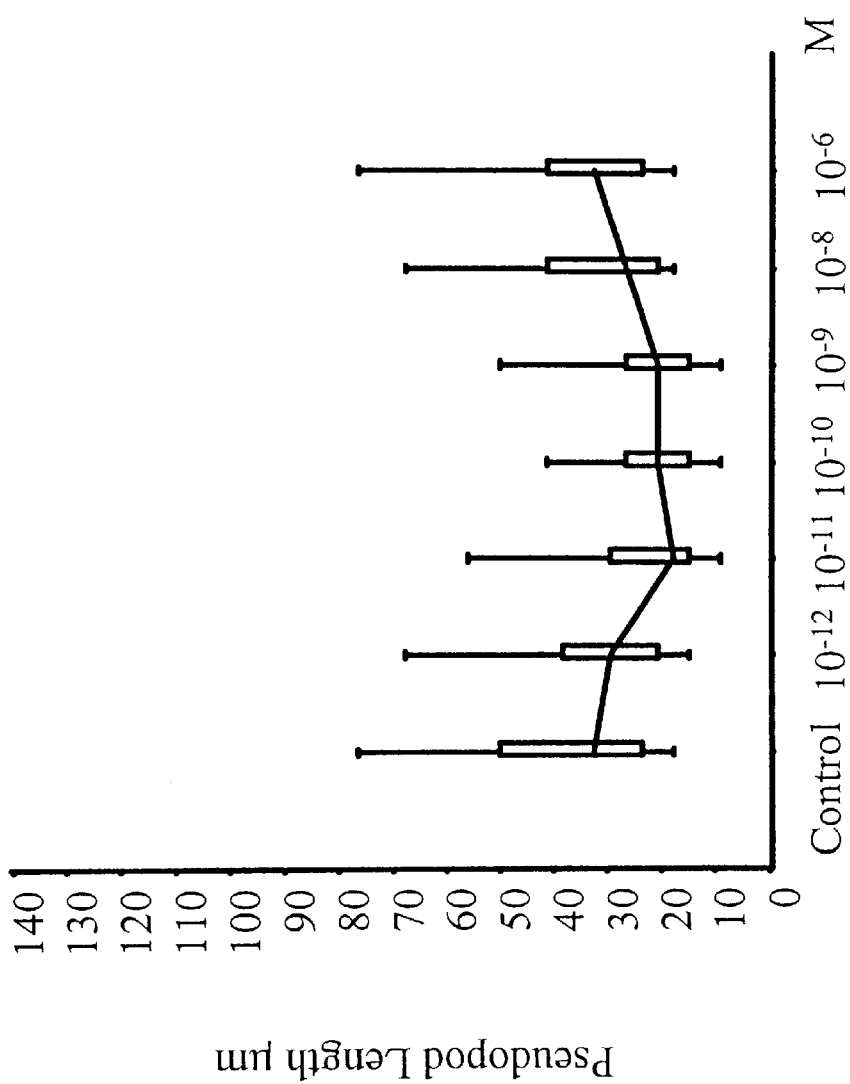
Figure 14A:
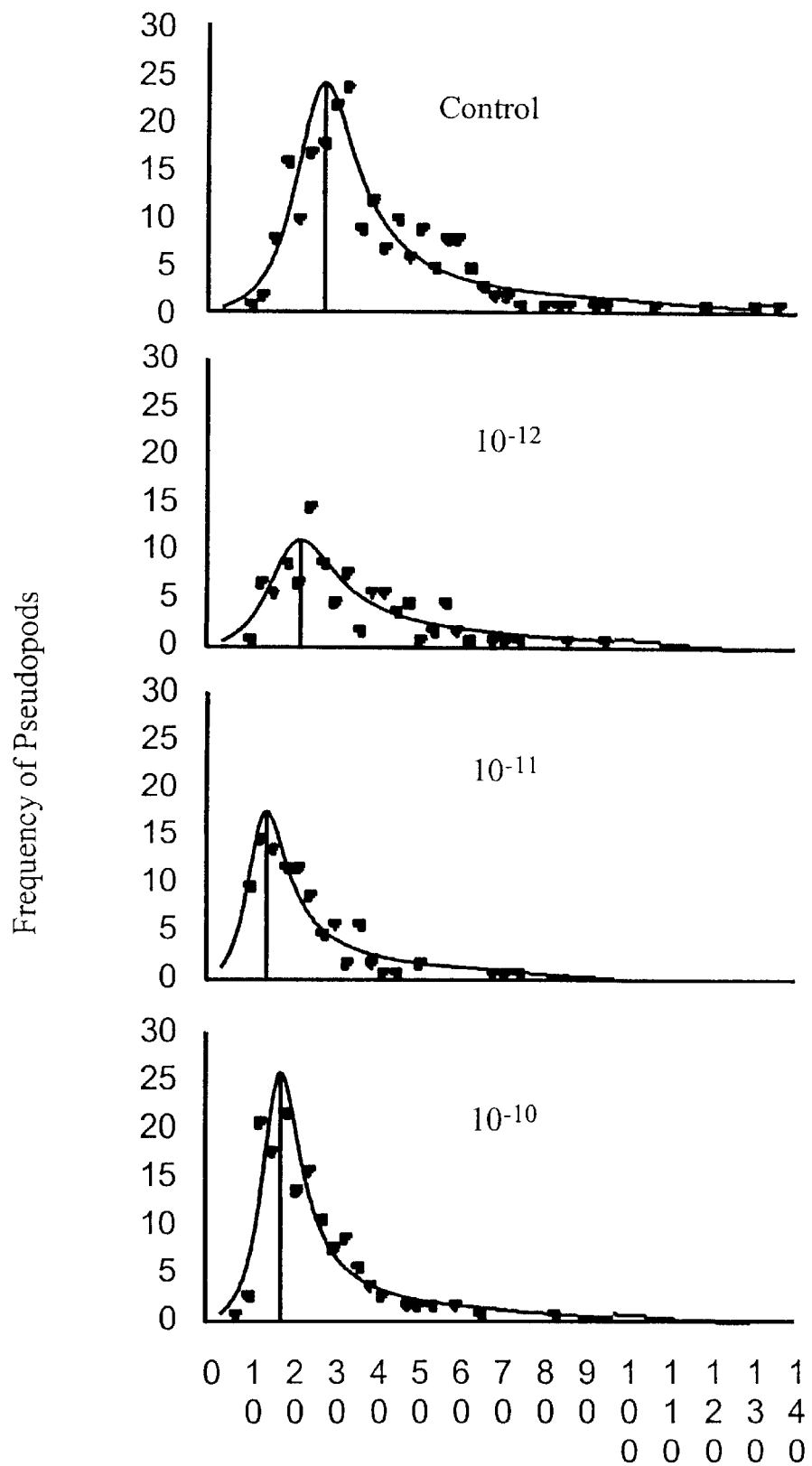
FIGS. 14A–14B. Histograms of pseudopod lengths of MAT-Lu cells exposed to different concentrations (M) of 12(S)-HETE for 15 min.
Figure 14B:
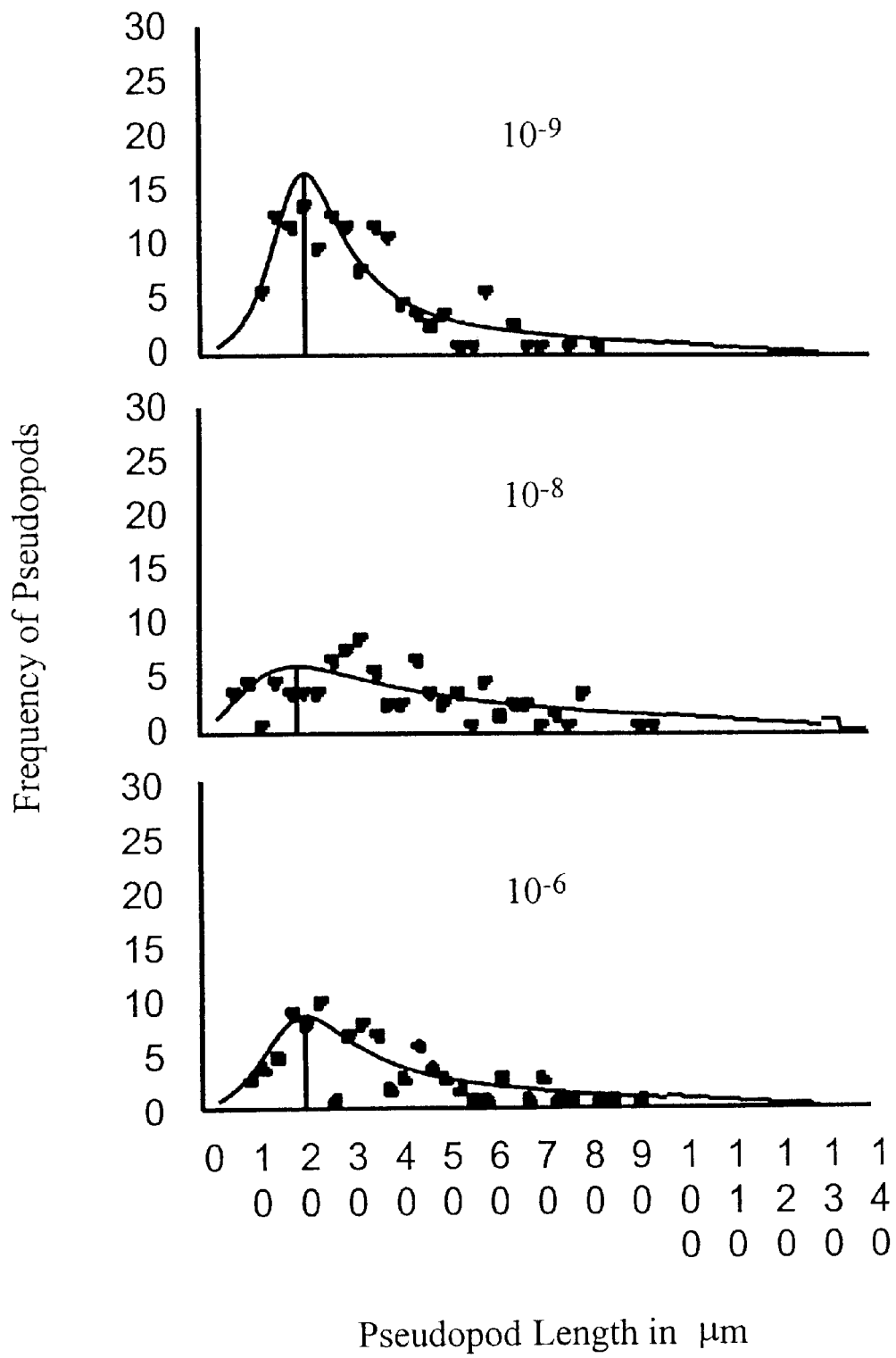
Figure 15:
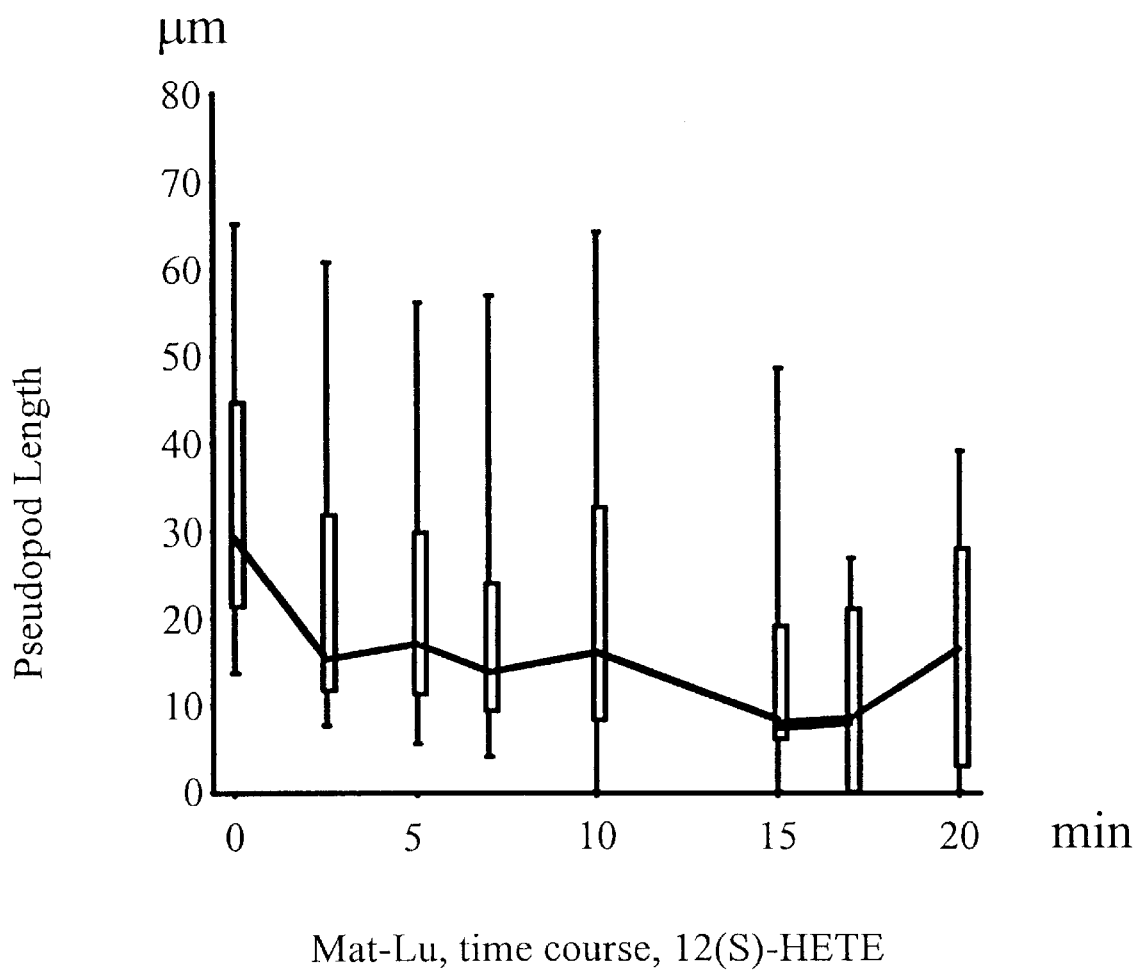
FIG. 15. Time course of pseudopod shortening induced by $10^{-10}$ M 12(S)-HETE introduced at time 0 by medium replacement. Data were pooled from 73 identified pseudopods (on 37 cells) followed over 20 min. Pseudopod lengths reach a minimum at about 17 min. For explanation of whisker-box plot, see FIG. 13.

Dose responses of pseudopod lengths to different HETEs were measured after 15 min incubation. Raw data for 12(S)-HETE are shown in FIG. 14. As expected, pseudopod lengths did not form a Gaussian distribution. However, the data could be fitted with a gamma regression model. The vertical lines in the histograms indicate the mode. It shifts to a shorter pseudopod length at $10^{-11}$ and $10^{-10}$ M and then back to approximately control levels at higher concentrations of 12(S)-HETE. The whisker-box plot in FIG. 12A shows more clearly the change in pseudopod length distributions induced by 12(S)-HETE. At $10^{-11}$ and $10^{-10}$ M, values are significantly smaller than control (>45% length reduction for the median; p<0.0001). The overall curvilinear depressed pattern, with pseudopod lengths returning to control levels at the higher concentrations ($10^{-8}$ and $10^{-6}$M), could be fitted with a quadratic polynomial across the log doses -12 through -8 (p<0.0001). This curve displayed a minimum at log -10.4M. The time course of pseudopod shortening is shown in FIG. 15 for a population of 73 identified pseudopods upon general application of $10^{-10}$ M 12(S)-HETE. As a control for 12(S)-HETE, we used its stereoisomer in the same experiments. At $10^{-10}$, but not at $10^{-6}$ M 12(R)-HETE, we observed a small reduction in pseudopod length (FIG. 12B). Two other isomers of 12(S)-HETE were tested as well. 5(S)-HETE at $10^{-10}$ M had no effect on pseudopod length (FIG. 12B). However, 15(S)-HETE reduced pseudopod lengths of MAT-Lu cells in a biphasic manner, like 12(S)-HETE (FIG. 12C). The effect was significant (p<0.0001) and peaked at log -10.0M. In summary, 12(S)-HETE and 15(S)-HETE caused a rapid and dramatic, biphasic reduction in pseudopod length, with the maximum effect observed between $10^{-10}$ and $10^{-11}$ M, whereas the other isomers tested were essentially inactive.

Figure 12D:
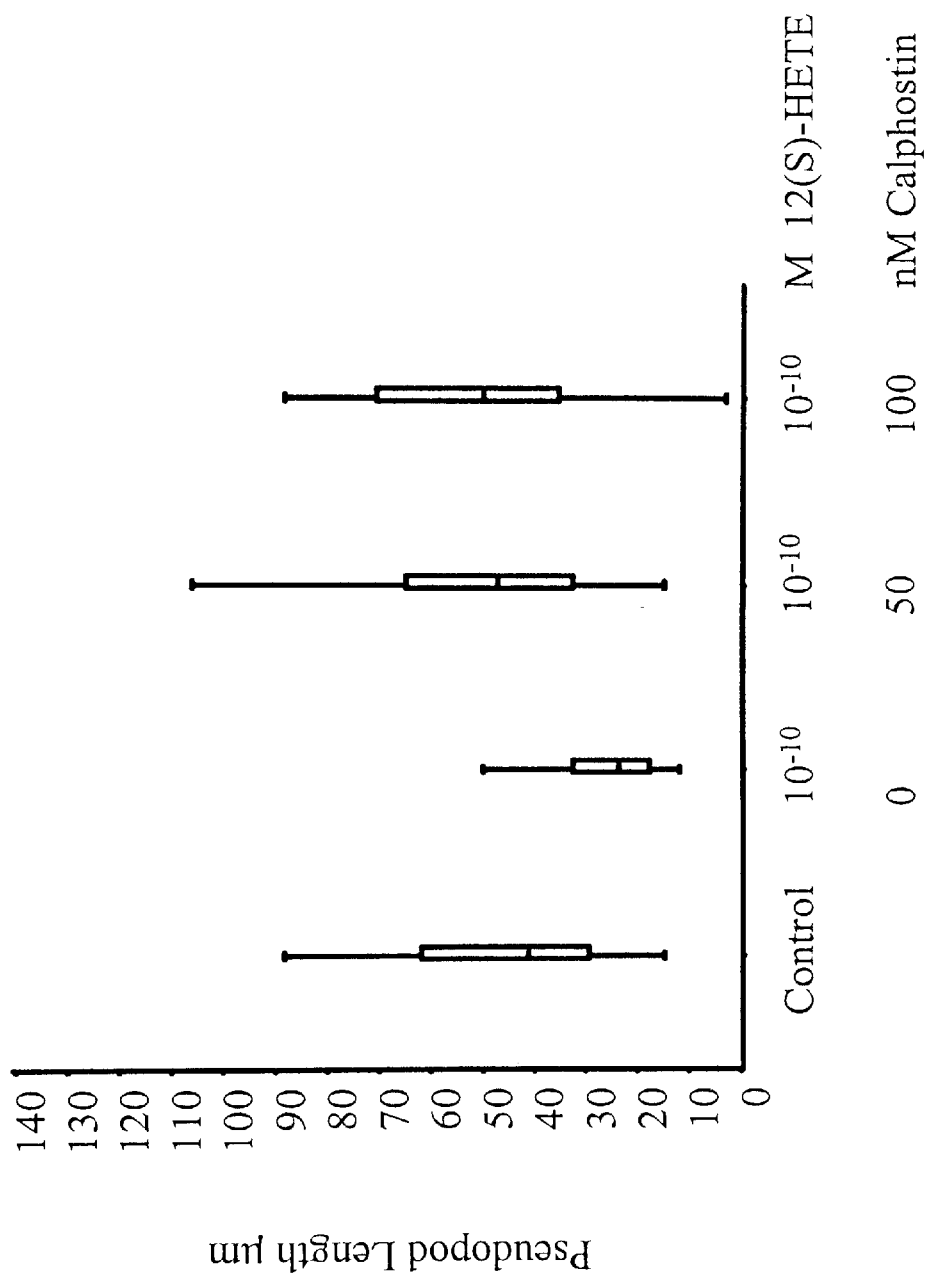

Further downstream of eicosanoid generation, 12(S)-HETE may directly or indirectly activate protein kinase C. To test the role of PKC in pseudopod detachment and shortening the blocker calphostin C was used to pretreat cells for 15 mins. (Kobayashi et al., *Biochem. Biophysi. Res. Comm.* 159:548–553 (1989)) in conjunction with 12(S)-HETE ($10^{-10}$M). As shown in FIG. 12D, at 50 nM ($IC_{50}$) and at 100 nM, calphostin completely inhibited pseudopod withdrawal triggered by 12(S)-HETE (p<0.0001).

Figure 8C:
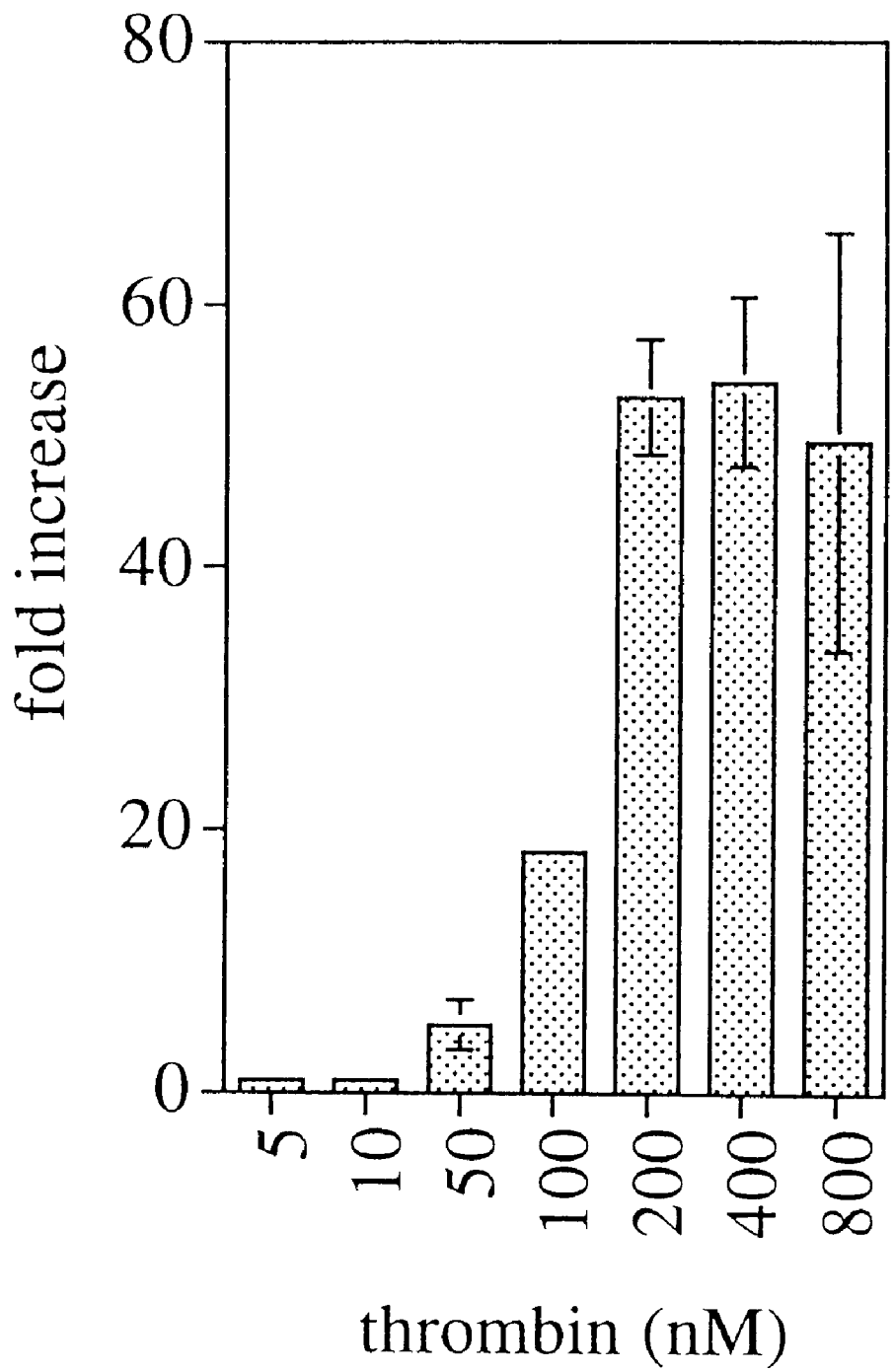
Figure 9:
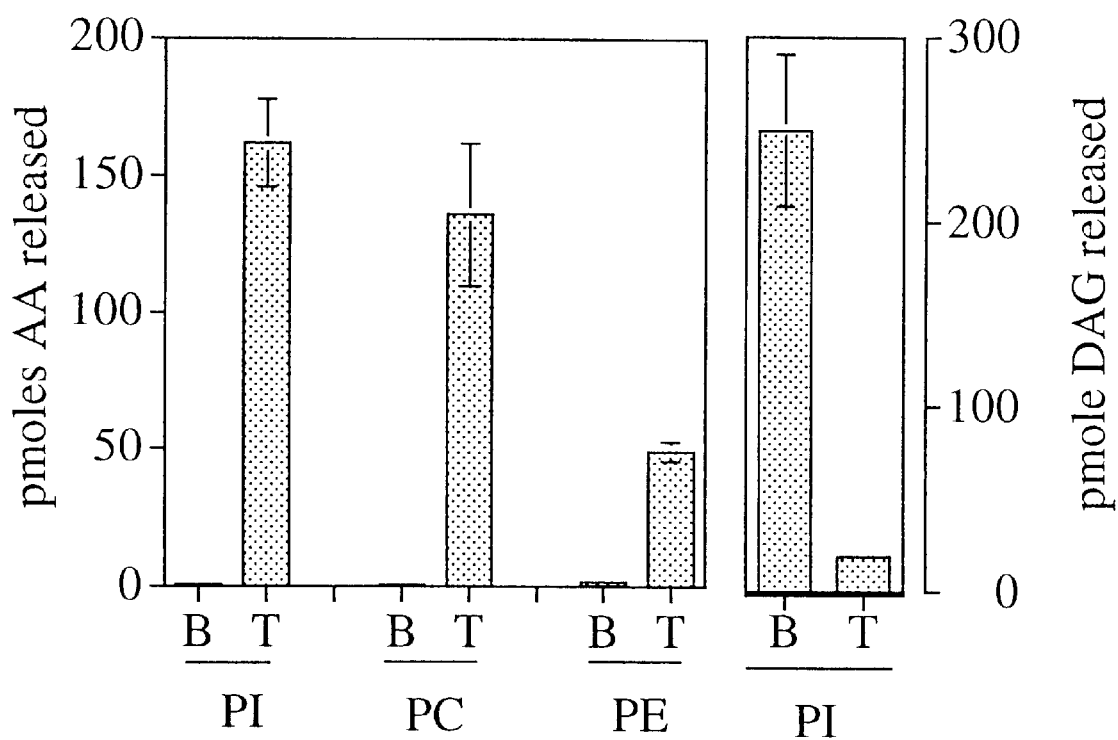
FIG. 9. Thrombin activation of cPLA$_2$ in AT-2 cells incubated with either $^{14}$C-AA-PI, -PC or -PE as substrate, for 10 min at 37° C. Released AA and diacylglycerol were isolated and counted.

Phospholipase Activity in MAT-Lu Cells. The behavioral and morphometric studies suggest that thrombin stimulates cPLA$_2$ in MAT-Lu cells. Therefore, AA release from exogenous $^{14}$C-AA-phosphatidylethanolamine (PE), -phosphatidylcholine (PC) and phosphatidylinositol (PI) were measured. Although AA release from PI is higher than from the other substrates under resting conditions, stimulation with thrombin results in a large increase (for PC>100 fold) in AA release, to about the same molar levels for all three substrates (FIG. 8A and B). Under the same conditions of thrombin stimulation, we also looked for changes in $^{14}$C-AA-diacylglycerol (DAG) release from $^{14}$C-AA-PI (FIG. 8A). While DAG release from PI was much higher than that of AA under resting conditions, thrombin actually reduced DAG release rather than stimulating it. There was essentially no DAG release from PE and PC. To test for the possible involvement of secreted PLA$_2$ we performed PLA$_2$ assays in the presence of reducing agent (5 mM dithiothreitol, DTT), which inhibits secreted PLA$_2$s but leaves cytosolic PLA$_2$s unaffected. As shown in FIG. 8B, DTT did not significantly inhibit the measured PLA$_2$ activity. The dose response of cPLA$_2$ to thrombin is shown in FIG. 8C for the PE substrate.

Thrombin Effects on MAT-Lu Cell Behavior. Thrombin greatly inhibited cell motility in our Boyden chamber assays and, thus, has a negative chemotactic effect on the MAT-Lu cells. Short-term morphometric studies revealed that pseudopod withdrawal was the reason for decreased cell migration. Therefore, thrombin's effect on these cells is that of a repellent, similar to what can be observed with growing neurites (Monard, *Trends Neurosci* 11:541–544 (1988)). Morphological observations suggest that the pseudopods react to thrombin and 12(S)-HETE first by detachment, rather than by increased tension and subsequent passive disruption of attachment sites. Therefore, thrombin and eicosanoids exert their effects on cellular adhesion sites.

Thrombin Activation of PLA$_2$. Analysis of reaction products from radiolabeled-PI substrate included not only AA but also DAG. Thrombin did not increase the levels of radiolabeled-DAG compared to controls and, therefore, did not activate phospholipase C in MAT-Lu cells. In contrast, AA release from PI was stimulated about 18 fold by thrombin, and it was increased 36 or 113 fold, respectively, when PE or PC were used as substrates. However, the molar levels of AA released from these exogenous substrates at maximum thrombin stimulation were about the same. Resistance to reducing agent and activity at low calcium levels (100 $\mu$M) indicate involvement of cPLA$_2$. Several forms of cPLA$_2$ have been characterized to date (Dennis, *J Biol Chem* 269:13057–13060 (1994); Leslie, *J Biol Chem* 272:16709–16712 (1997)). The substrate selectivity observed is consistent with the activation of a PI-selective enzyme previously observed in nerve growth cones (Negre-Aminou et al., 1996), perhaps together with cPLA$_2$-85, the PE-and PC-selective 85-kDa enzyme.

If cPLA$_2$ is causally involved in pseudopod withdrawal, then its inhibition ought to block the effect of thrombin. Likewise, if cPLA$_2$ is involved in this pathway, then one of the enzyme's products, AA or a lysophospholipid, should have the same effect. Micromolar AA mimics thrombin. Furthermore, inhibitors of 12-LOX, especially CDC, neutralize the negative-chemotactic effect of thrombin. This supports the causal involvement of cPLA$_2$ because eicosanoid synthesis depends on the cellular supply of AA.

Role of Eicosanoids in Thrombin Signaling. The thrombin-like effect of AA on pseudopod length could be due to its direct interaction with a downstream effector or it could occur indirectly, via a metabolite. The cyclooxygenase inhibitor, indomethacin, did not interfere with AA-induced pseudopod shortening. In contrast the LOX blockers NDGA and CDC inhibited the AA effect completely. At the concentrations used, CDC is quite selective for 12-LOX suggesting that 12(S)-HETE is necessary for pseudopod shortening. This is supported by the fact that CDC blocks the effects of thrombin.

While the 12-LOX inhibitor, CDC, inhibits the repellent effect of thrombin, the product of 12-LOX, 12(S)-HETE, replicates the thrombin effect at very low concentrations ($10^{-11}$ to 10 M). Thus, the MAT-Lu response to this eicosanoid is similar to the 12(S)-HETE-elicited retraction of endothelial cells described in Tang et al., *Exp Cell Res* 207:361–375 (1993). Another eicosanoid, 15(S)-HETE, also causes MAT-Lu pseudopods to withdraw, but the biologically inactive 12(R)-HETE, and another isomer, 5(S)-HETE, cause only minimal or no changes in pseudopod length. These data indicate potent, stereo-specific action of 12(S)-HETE and 15(S)-HETE on the MAT-Lu pseudopods.

The data indicate that thrombin acts on certain cell types, such as the MAT-Lu cells, or their pseudopods in a manner comparable to that of repellents on nerve growth cones. In more general terms, this suggests the operation of negative chemotactic mechanisms in non-neural vertebrate tissues.

Our observations reveal the signaling mechanism involved in thrombin's repellent action. The data indicate that cPLA$_2$ and 12-LOX are necessary, and that 12(S)-HETE is sufficient for the repellent effect. Furthermore, 12(S)-HETE stimulates PKC, without the involvement of PLC, and PKC activation is necessary for pseudopod detachment and withdrawal.

These examples establish (i) that certain growth cone repellents suppress CaP cell migration, (ii) that such repellents trigger pseudopod adhesion site disassembly in CaP cells, and (iii) that this is mediated by a signaling pathway involving cPLA$_2$, eicosanoid production and PKC activation.

EXAMPLE 8

Thrombin-Induced Growth Cone Collapse Studies

The following studies were conducted to show that (a) PLA$_2$ activation and 12(S)-HETE generation are necessary for thrombin-induced growth cone collapse, (b) 12(S)-HETE mimics the thrombin response, and (c) a signalling pathway involving PLA$_2$ and 12-LOX regulates growth cone detachment.

1. Materials and Methods

Materials. Free arachidonic acid (AA) was purchased from Sigma (St. Louis, Mo.) and 1-stearoyl-2-arachidonyl-sn-glycerol (DG) from Avanti-Polar Lipids (Alabaster, AL). L-$\alpha$-stearoyl-2-$^{14}$C-arachidonyl-phosphatidylinositol ($^{14}$C-AA-PI; 20–40 mCi/mmol), -phosphatidylethanolamine ($^{14}$C-AA-PE; 40–60 mCi/mmol) and -phosphatidylcholine ($^{14}$C-AA-PC; 40–60 mCi/mmol) were obtained from Dupont New England Nuclear (Boston, Mass.) as was $^3$H-arachidonic acid ($^3$H-AA). Reagents for chemiluminescence were from the same vendor. Analytical grade solvents for routine thin-layer-chromatography (TLC) analysis and tissue culture dishes were purchased from Fisher (Pittsburg, Pa.). BDM (2,3-butanedione monoxime), TES (N-tris-[hydroxymethyl]-methyl-2-aminoethane-sulfonic acid), thrombin and other chemicals were from Sigma (St. Louis, Mo.). Aprotinin was from Calbiochem (San Diego, Calif.). Polyacrylamide, pre-stained molecular weight standards and other reagents for sodium-dodecyl-sulphate (SDS)-polyacrylamide gel electrophoresis (PAGE) were from Gibco BRL (Grand-Island, N.Y.). Tissue culture media and laminin were also from Gibco BRL. HETE, nordihydroguaiaretic acid (NDGA), cinnamyl-3,4-dihydroxy-α-cyanocinnamate (CDC) and indomethacin were purchased from Biomol (Plymouth Meeting, Pa.). Thrombin receptor activating hexapeptide TRAP) came from Peninsula Laboratories (San Carlos, Calif.). TLC plates were obtained from EM Science (Gibbstown, N.J.) and from WHATMAN (Clifton, N.J.). Sprague-Dawley rats were from Harlan (Indianapolis, Ind.). SPE columns were purchased from J. T. Baker (Phillipsburg, N.J.). Antibody to platelet-Lox was from OXFORD Biomedical Research (Oxford, Mich.) and antibody to leukocyte-Lox was purchased from Cayman Chemical Company (Ann Arbor, Mich.). HRP-conjugated goat anti-rabbit antibody was purchased from Vector Laboratories (Burlingame, Calif.). Coverglasses and slides were purchased from Carolina Biological Supply (Burlington, N.C.). Texas-Red-conjugated phalloidin and Slow-Fade Light were products of Molecular Probes (Eugene, Ore.). Insulin and IGF-1 were from Collaborative Biomedical Products (Bedford, Mass.) and BDNF from Amgen Inc. (Thousand Oaks, Calif.).

Neuron Culture. Cerebral cortices were dissected from embryonic day 18 Sprague-Dawley rats, cut into explants of less than 1 mm$^3$ and cultured on either poly-D-lysine-coated coverglass (Assistent) or poly-D-lvsine-coated tissue culture plastic. After 24 hours in B27 neurobasal medium (NB) supplemented with 10% fetal bovine serum, cultures were switched to serum-free B27/NB. The cultures were incubated at 37° C. in 5% $CO_2$ in air. Sprouting neurons were observed readily on day 1. On day 2 or 3, long neurites were present, and the cultures were used for collapse experiments.

Actin Staining. After experimentation, cultures were fixed by slow infusion of fixative (4% paraformaldehyde in 0.1 M phosphate buffer, pH 7.4) into the culture dishes over 10 min (Pfenninger and Maylié-Pfenninger, *J. Cell Biol.* 89:53–546 (1981)). Thereafter, the fixative was removed by rinsing three times with phosphate-buffered saline (PBS) containing 1 mM glycine. Cultures were then blocked with PBS/1% bovine serum albumin (BSA) and permeabilized by incubation in 0.02% Triton X-100 for 5 min. After three washes in PBS/BSA, cultures were incubated with Texas-Red-conjugated phalloidin for 30 min. Unbound phalloidin was washed away by two PBS rinses, after which the coverglasses were mounted in Slow-Fade Light on microscope slides. Images were recorded on 35 mm film using a Zeiss Axiophot fluorescence microscope equipped with epiillumination.

Growth Cone Collapse Assay. Prior to repellent factor treatment, some of the day 2–3 explant cultures were pre-incubated (at 37° C.) with inhibitor or vehicle control (dimethylsulfoxide or ethanol) for 30–60 min. Cultures were then challenged with a repellent factor or vehicle control for 1–30 min. In some experiments, live cultures were photographed with a Zeiss IM 35 inverted photo microscope equipped with a stage heater, while in others cultures were fixed (as above) after 7 minutes of repellent factor treatment. Growth cone collapse was assessed quantitatively in aldehyde-fixed cultures by grading the degree of collapse in a large number of randomly selected growth cones. Growth cones were classified in one of four categories: fully spread, "veiled" growth cones; partially spread growth cones possessing filopodia; partially collapsed growth cones with filopodia; and fully collapsed, "club"-shaped growth cones.

Growth Cone Particle (GCP) Isolation. GCPs were prepared as described by Pfenninger et al. (1983) and modified by Lohse et al., *Dev. Brain Res.*, 96:38–96 (1996). Briefly, 18-day fetal brains were homogenized in approximately 8 volumes of 0.32 M sucrose containing 1 mM $MgCl_2$, 2 mM TES buffer, pH 7.3, and 3 µM aprotinin. A low-speed supernatant (1,660 g×15 min) was loaded onto a discontinuous sucrose density gradient With steps of 0.83 M and 2.66 M sucrose containing $MgCl_2$ and TES. The gradients were spun to equilibrium at 242,000 g for 40 min in a vertical rotor (Vti50, Beckman). The GCP fraction at the 0.32/0.83 M sucrose interface was collected and used for the experiments described below.

GCP Release Assay. Petri dishes (35 mm diameter) were coated with 10 µg mouse laminin in PBS by incubation at room temperature for 60 min with shaking. Dishes were subsequently rinsed three times with PBS to remove unbound laminin and then blocked with 5% non-fat dry milk (Carnation) in PBS for 30 min. After three PBS rinses to remove blocking agent, the dishes were ready for the addition of GCPs. Prior to plating, the GCP fraction was slowly added at 4° C. to an equivalent volume of 2× concentrated, modified Krebs buffer (22 mM sucrose, 50 mM NaCl, 5 mM KCl, 22 mM Hepes pH 7.4, 10 mM glucose, 1.2 mM $NaH_2PO_4$, 1.2 mM $MgCl_2$ and 2 mM $CaCl_2$). After incubation for five min at 37° C. this buffered GCP preparation was added to the lamincoated petri dishes. Contact with the substratum was facilitated by centrifuging the dishes for 15 min at 5000 g (Beckman JS5.2 rotor) at room temperature, followed by incubation at 37° C. to allow adhesion site formation. After 10 min, unattached GCPs were removed by rinsing the dishes twice with 1× modified Krebs buffer. Plated GCPs were then challenged with repellent factor (TRAP or thrombin) for 20 min at 37° C. The supernatant containing released GCPs was collected and centrifuged for protein determination of the pellet. GCPs that remained attached after repellent treatment were removed with 5% sodium dodecyl sulfate (SDS) for protein assay. Protein was measured according to Lowry et al. (1951) as modified by Peterson (1983). Results of these experiments were expressed as the percentage of released versus total GCP protein in the assay.

Gel Electrophoresis and Western Blotting. SDS-PAGE was performed according to Laemmli (1970), using 5–15% acrylamide gradients. The GCP fraction was diluted 3–4 fold with 0.32 M sucrose buffer and spun for 30 min at 39,800 g. Protein amounts in the pellets were determined by dye-binding assay as described in Brafford, *Anal Biochem* 72:248–257 (1976). Polypeptides of pelleted GCPs (30 µg/lane) were resolved by SDS-PAGE. Pre-stained standards were used to determine apparent molecular mass. Resolved proteins were transferred to nitrocellulose essentially as described by Towbin et al., *Proc. Natl Acad Sci USA*, 76:4350–4354 (1979), with a semidry blotting apparatus for 60 min at 300 mA for a 14×17 cm gel. Ponceau S staining served to monitor the efficiency of protein transfer. Blots were then rinsed in PBS and distilled water and dried. Prior to incubation with primary antibody, blots were blocked with 5% non-fat milk powder and 0.02% Tween-20 in PBS for two hours at room temperature. Blots were probed in the same blocking solution and conditions with either polyclonal rabbit anti-platelet or polyclonal rabbit anti-leukocyte 12-Lox antibody at 1:2000 or 1:5000, respectively. Blots were washed five times in blocking solution, followed by incubation with secondary antibody (HRP-conjugated goat anti-rabbit antibody at 1:5000) for one hour in blocking solution. After extensive washing, bound antibody was detected by enhanced chemiluminescence according to the manufacturer's directions (New England Nuclear, Boston Mass.) by contact-exposing x-ray film (Kodak X-OMAT BLUE XB-1).

Phospholipase Assays. For $PLA_2$ assays, GCPs suspended in modified $Ca^{2+}$-free Krebs buffer (10–30 μg protein/assay) were first incubated for 10 min on ice in the presence or absence of effectors. Subsequently, phospholipid substrate (PC, PE or PI) containing radiolabelled AA (7 μM; 50,000 cpm/assay) was added and the reaction carried out at 37° C. for 10 minutes. Typically, assay mixtures contained 10 μM $CaCl_2$; specific modifications are described in the figure legends. For phospholipase C (PLC) assays, conditions were the same when run in parallel with $PLA_2$ assays. When PLC assays were run independently, $Ca^{2+}$ was increased to 1 mM. Reactions were terminated by the addition of 3.75 volumes of cold chloroform/methanol (1:2). $PLA_2$ assays also were performed on neurons dissociated from fetal rat cerebral cortex. The assay conditions were the same as those just described for GCPs.

Extraction of phospholipase products was carried out according to Bligh and Dyer, *Canadien J Biochem and Physiol*, 37:911–917 (1959). Products recovered in chloroform were loaded onto silica gel 60 TLC plates and developed as described earlier (Nègre-Aminou and Pfenninger, 1993) in hexane/ether/acetic acid (40:60:1). AA and DG were identified on TLC by co-migration with authentic standards. The appropriate bands were excised into scintillation fluid and counted on a Beckman LS 1801 scintillation sprectometer. All assays were run in triplicate.

Eicosanoid Assays. Eicosanoid production in GCPs was measured by metabolic labelling from $^{14}C$-AA or $^{14}C$-AA-PC or by mass spectrometric detection. To determine HETE synthesis by radiolabelling, assays were run essentially as for $PLA_2$ except that phospholipid substrate was increased to 100,000 cpm/assay, and assay time at 37° C. was 15 minutes. To measure Lox activity directly, without $PLA_2$ involvement, $^3H$-AA was the substrate of choice. Reactions were stopped by the addition of chloroform/methanol as for the phospholipase assays. Reaction products were extracted as described by Birkle et al., Neuromethods, vol. 7, pp.227–244 (Humana Press, N.J. 1988), spotted on pre-activated si gel 60 TLC plates, and the plates developed in the upper phase of ethyl acetate/isooctane/acetic acid/water (100:60:20:100). AA and HETEs were identified by co-migration with standards. Appropriate bands were counted by liquid scintillation spectrometry.

For mass-spectrometric (MS) identification of HETEs, two different strategies were pursued:

(1) the appropriate bands from non-labelled samples (PC substrate) were scraped from the TLC plate into ether/methanol (9:1) and stored under $N_2$ at –20° C. Authentic 12(S)-HETE, run alongside in the same manner, was used as a standard. Just prior to analysis, samples were passed over an SPE filter to eliminate silica particles, dried under argon, resuspended in 500 μl ethanol, and injected (at 3 μl/min) into a Finnigan LCQ quadrupole ion trap mass spectrometer (Finnigan MAT, San Jose, Calif.) equipped with an electrospray ionization source. All spectra were acquired at a capillary temperature of 80° C., and ion guide voltages were tuned to maximize the abundance of the deprotonated ion species $[M-H]^-$ in negative mode. In order to generate a spectrum, typically 100 single scans were averaged.

(2) For the other strategy (liquid chromatography/tandem MS, $LC/MS^2$), the reaction substrate consisted of 3.5 μM AA, with the addition of 3.5 μM deuterated AA ($AA-D_8$) plus 1 μCi $^3H$-AA to track reaction products by mass and radioactivity, respectively. Reactions were stopped with ice-cold ethanol, the mixtures kept overnight at –20° C. under $N_2$, and the proteins spun out The supernatants were diluted with $H_2O$ and loaded onto 1-ml $C_{18}$ Sep-Pak columns (Varian). After washing with $H_2O$, eicosanoid was eluted with 2 ml methanol. These samples were resolved by reverse-phase HPLC, and the eluted fractions analyzed by tandem MS on-line (MacMillan and Murphy, 1995). Collision-induced decomposition of HETE isomers produced characteristic fragments that were identified at the second MS stage.

2. Results

Growth Cone Collapse in Culture. Experiments were performed on growth cones in cultures of rat cerebral cortex to assess qualitatively and quantitatively the collapsing effects of thrombin and the non-proteolytic TRAP, with or without inhibitors of AA metabolism. In these studies, cultures of E18 rat cortical neurons were either pretreated with vehicle alone or inhibitor for 45 minutes prior to collapse factor treatment with thrombin or 12(S)-HETE. The treatments included: (1) 100 nM thrombin treatment; (2) 25 μM indomethacin pretreatment followed by 100 nM thrombin; (3) 10 μM CDC pretreatment followed by 100 nM thrombin; (4) $10^{-7}$ M 12(S)-HETE treatment of growth cones at different times. Within minutes, thrombin causes disappearance of lamellipodia and, eventually, filopodia. After 10–20 min, most growth cones are fully collapsed and neurites exhibit beading and length reduction. TRAP was used at a concentration about 1000 times higher than that of thrombin, consistent with data on receptor binding and TRAP activation in other systems. TRAP has qualitatively the same effect as thrombin, but the change is not as pronounced, and neurite beading is not as common. The collapse phenomenon can be seen at higher magnification after staining of filamentous actin with Texas-Red-conjugated phalloidin. Control growth cones exhibit spread-out veils and/or filopodia with filamentous actin enriched in the periphery whereas thrombin or TRAP treatment causes withdrawal of lamellipodia and filopodia and actin redistribution from the peripheral to the proximal growth cone.

In order to test for the putative role of $PLA_2$ in thrombin/TRAP signalling, it would ideally inhibit or activate growth cone $PLA_2$. However, the molecular identities of growth cone $PLA_2$s have not been established, and selective inhibitors that block these enzymes are not known. Therefore, we proceeded with experiments involving inhibitors of the metabolism of the $PLA_2$ product, AA. Indomethacin is a specific blocker of cyclooxygenase, thereby inhibiting the synthesis of prostaglandins and related eicosanoids (Salari et al., *Prostaglandins Luckotrienes and Medicine*, 13:53–60 (1984)). As indicated above, CDC is a selective inhibitor of Loxes, including 12-Lox, which catalyzes the synthesis of 12(S)- and some 15(S)-HETE. Indomethacin has no effect on control or thrombin treatment of growth cones. However, pretreatment with CDC inhibits the thrombin effect on growth cones. While thrombin collapses growth cones even after incubation with indomethacin, CDC-pretreated growth cones retain their spread-out appearance. A more potent but less selective inhibitor of all Loxes, NDGA (Salari et al., 1984), also protects growth cones from thrombin- or TRAP-induced collapse.

Comparisons were done of phalloidin-stained growth cones, in control cultures and in cultures challenged with thrombin or TRAP after CDC incubation. Cultured E18 rat cortical neurons were fixed and stained with Texas-Red-conjugated phalloidin after the following experimental treatments: control (vehicle alone); thrombin (100 nM) for 7 minutes; TRAP (100 mM) for 7 minutes; 45 minutes pretreatment with CDC (10 μM) followed by TRAP (100 mM) for 7 minutes; 12(S)-HETE ($10^{-7}$ M) for 10 minutes. Thrombin and TRAP cause collapse but the TRAP effect, while clear-cut, is not as dramatic as that of thrombin (arrows point at collapsed growth cones); CDC partially inhibits collapse; and 12(S)-HETE mimics the effects of thrombin and TRAP. The Lox inhibitor, CDC, inhibits thrombin-induced shape change of the growth cone, but not retraction of the actin cytoskeleton. Growth cones were fixed and stained with Texas-Red-conjugated phalloidin after control (vehicle alone) incubation and pretreated 30 minutes with CDC (1 μM), followed by thrombin challenge (100 nM) for 7 minutes. Intact filopodia with diminished actin staining were seen as well as "clumped" actin filaments in the proximal growth cone. This illustrates an important point: even though CDC-pretreated growth cones typically retain their spread-out shape with attached filopodia, a substantial amount of filamentous actin appears clumped in the proximal body of many of the growth cones. Some actin de-polymerization may have taken place as well. This observation suggests a dissociation of cytoskeletal redistribution (not inhibited) from filopodial detachment (inhibited by CDC).

Figure 17:
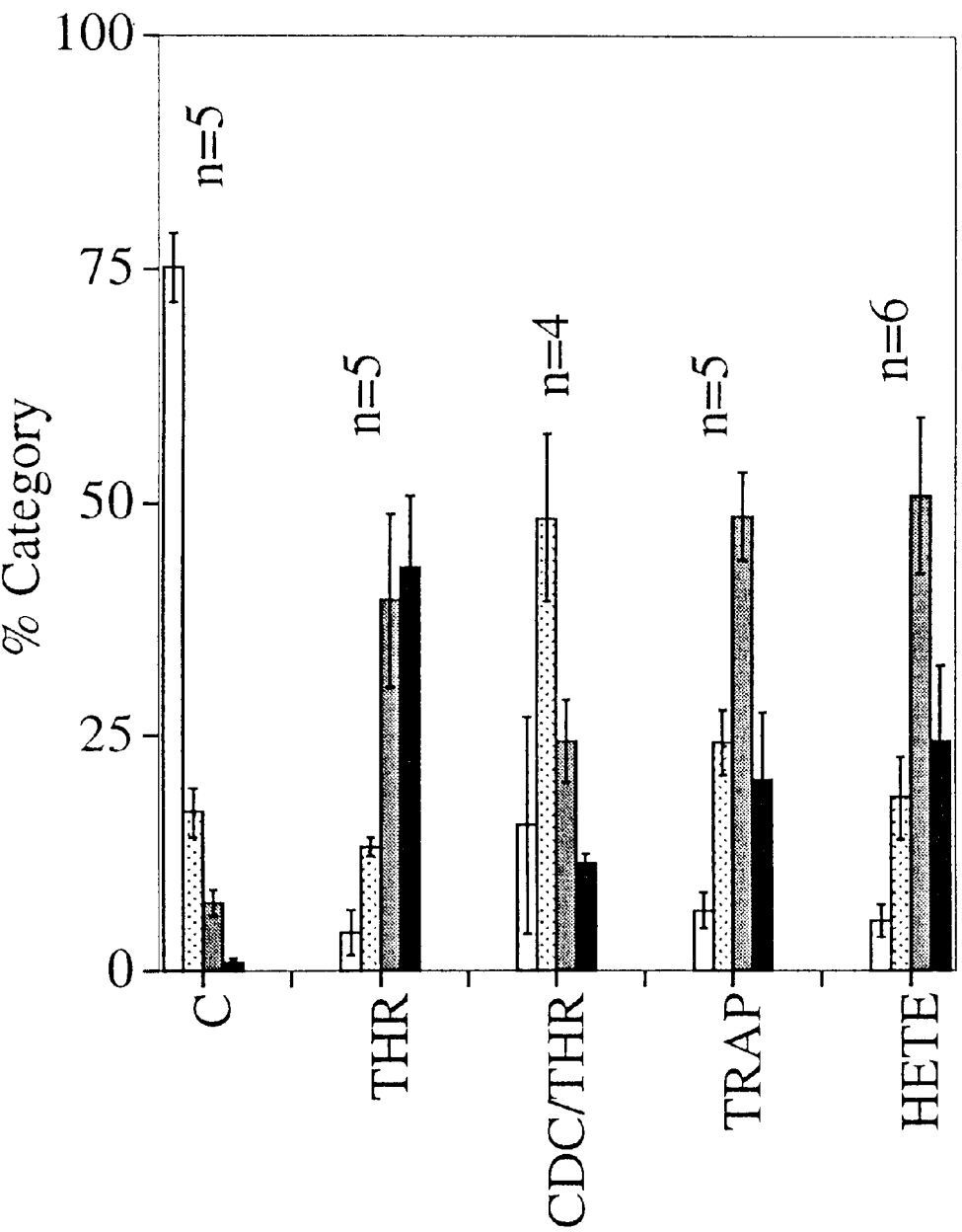

The results of these experiments have been analyzed quantitatively. At least 50 growth cones in each of 4 to 6 experiments were classified into four different categories: collapsed, partially collapsed, partially intact, and intact (see Methods). FIG. 17 shows a shift of growth cones from predominantly intact (controls) to predominantly collapsed (thrombin or TRAP) and the almost complete inhibition of this effect by CDC.

If 12-Lox is necessary for at least a part of the collapsing action of thrombin/TRAP, as the experiments with CDC suggest, then the primary 12-Lox product, 12(S)-HETE, should mimic the effect of thrombin/TRAP. This is shown quantitatively in FIG. 17. In this system at $10^{-7}$M, 12(S)-HETE does indeed cause growth cone collapse that is morphologically very similar to the effect of thrombin/TRAP. However, 12(S)-HETE-induced collapse is less dramatic (see FIG. 17), and the neurite beading seen after maximum thrombin exposure is observed only rarely. The collapse effect of 12(S)-HETE is not affected by growth cone pretreatment with the Lox inhibitor, CDC.

Growth Cone Detachment. Morphologic analysis of growth cones, as described above, suggests that cytoskeletal redistribution and filopodial detachment during collapse are separate phenomena. In order to test this hypothesis further we designed a cell-free substrate detachment assay involving so-called growth cone particles (GCPs) isolated from fetal rat brain (Pfenninger et al., 1983). GCPs contain a full complement of growth cone organelles, are viable for at least one hour after isolation and have been shown to be derived primarily from axonal growth cones (Lohse et al., 1996). When GCPs attached to laminin were exposed to thrombin, many of them detached from the substratum in a dose-dependent maaner and could be collected in the supernatant (FIG. 18). TRAP mimics the effect, indicating that protease activity is not required for detachment.

GCPs contain a substantial actin meshwork (Pfenninger et al., 1983). Despite their small size (about 0.3–0.5 μm diameter), contraction of the actin/myosin system could be responsible for at least some of the detachment effect observed in the assay. Therefore, laminin-attached GCPs were first treated for 20 min at 37° C. with 1 μM cytochalasin D to depolymerize the actin cytoskeleton or with 20 mN BDM to inhibit selectively myosin ATPasc. Both reagents caused considerable release of GCPs by themselves (FIG. 18) consistent with known effects on cell spreading. However, thrombin challenge increased detachment further, by 1.5 to 1.75 fold (p<0.05 for BDM; p<0.01 for cytochalasin D).

Phospholipase Activation. Our hypothesis predicts that one of the important steps in thrombin-induced growth cone collapse is the activation of cytosolic $PLA_2$. Therefore, we studied $PLA_2$ activation in primary neurons and in GCPs isolated from fetal rat brain. In $PLA_2$ assays performed on primary neurons dissociated from cerebral cortex, thrombin greatly stimulated AA release from PE or PI, as shown in Table 3a. Because of the specific effect of thrombin on growth cones and because of the enrichment of $PLA_2$ in growth cones (Nègre-Aminou et al., 1996), we proceeded with the more detailed analysis of $PLA_2$ activation in GCPs. Table 3a shows that, under comparable experimental conditions, thrombin stimulates $PLA_2$ in GCPs to much higher levels of free AA than in whole neurons. FIG. 6 shows the release of AA from PI as a function of increasing concentrations of thrombin or TRAP. We observed a high level of activation (from 5- to 7-fold) saturating at about 250 nM for thrombin. TRAP also clearly stimulated $PLA_2$, but to a considerably lesser degree and at a roughly 1000-fold higher concentration. We had determined previously that GCPs contain very little, if any, secreted $PLA_2$ (Nègre-Aminou et al., 1996). In order to exclude the possibility that thrombin stimulated the release of a secreted $PLA_2$ we performed $PLA_2$ assays in the presence of reducing agent, which inactivates the catalytic domain of all secreted forms of the enzyme. As Table 3b shows, dithiothreitol (DTT) does not reduce the control or thrombin-stimulated levels of $PLA_2$ activity. This confirms the role of cytosolic $PLA_2$ in a thrombin-activated pathway.

Figure 20:
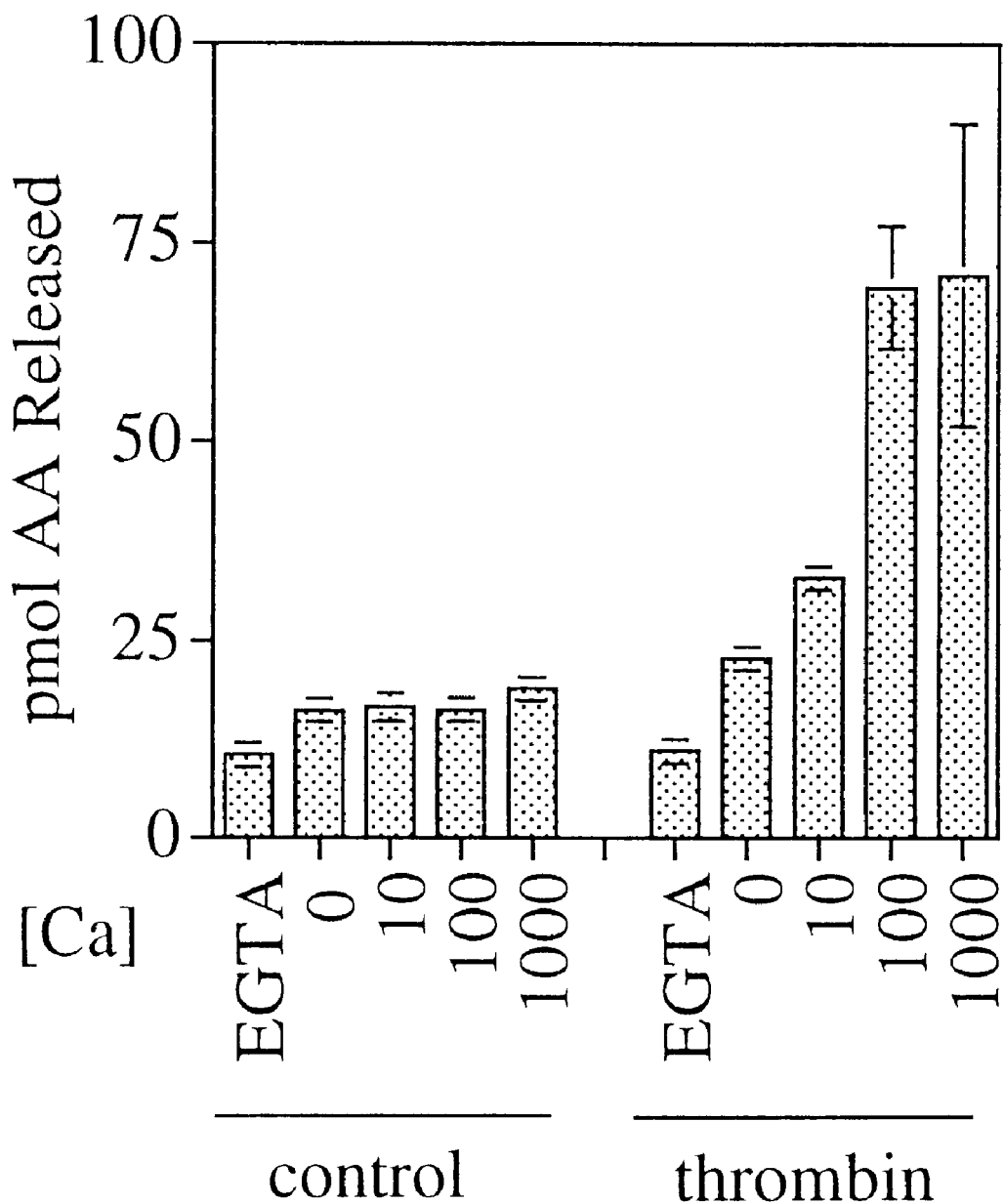
FIG. 20. Effects of calcium on control and thrombin-stimulated levels of PLA$_2$ in GCPs. GCPs were incubated alone (control) or in the presence of 100 nM thrombin for 10 minutes on ice, then combined with substrate ($^{14}$C-AA-PI) for 10 minutes at 37° C., in the presence of EGTA or varying µM concentrations of CaCl$_2$ ("0 Ca" indicates no addition of Ca$^{2+}$ or EGTA). AA release was measured as described in Methods. Data represent several experiments, each done in triplicate. Error bars are s.d.

The $PLA_2$ response to thrombin is calcium-dependent in permeabilized GCPs, as shown in FIG. 20. In the presence of EGTA, there is no stimulation of enzyme activity, whereas the thrombin response reaches a maximum at about 100 μM $Ca^{2+}$, without much change in basal, non-stimulated conditions.

Figure 21:
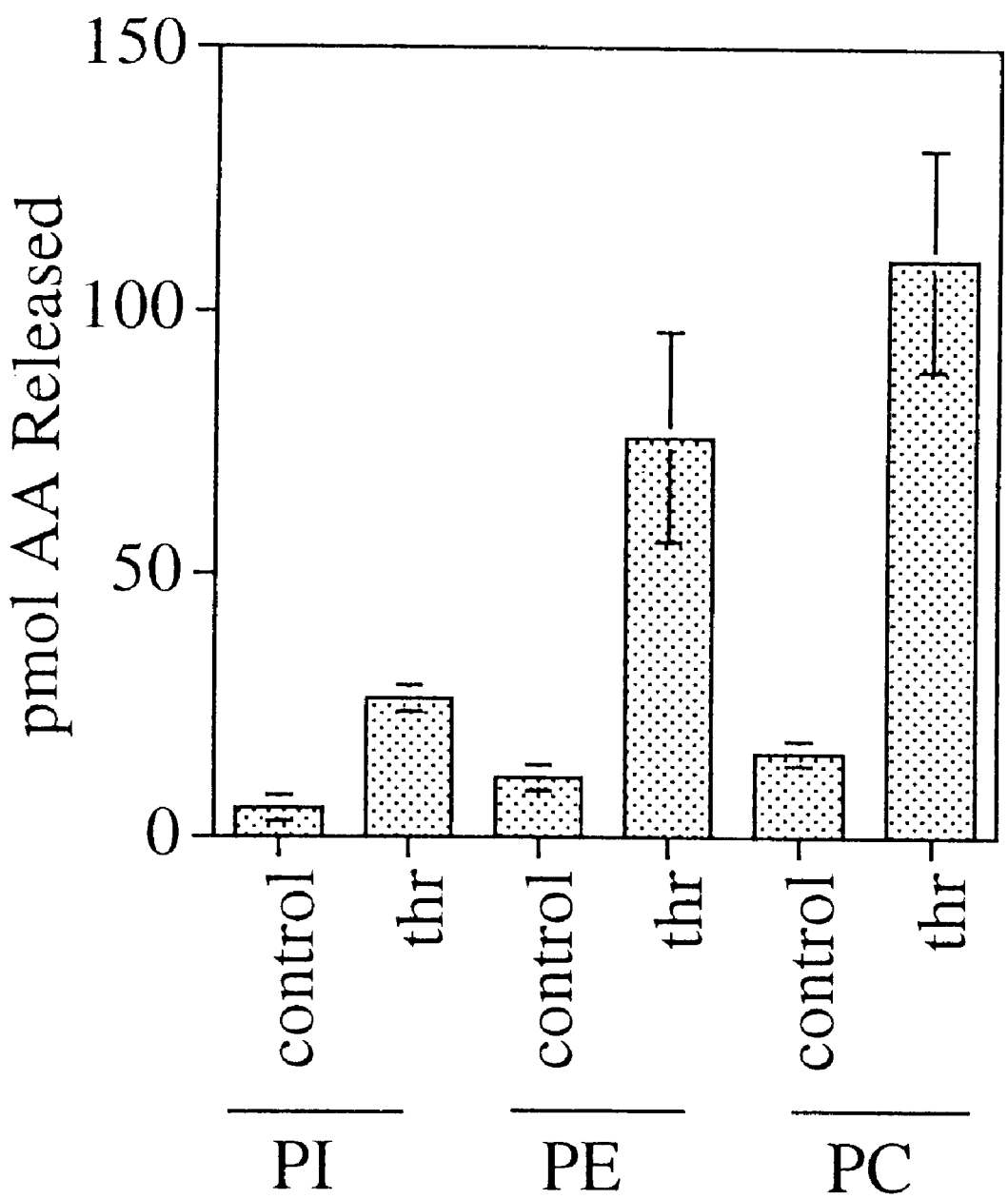
FIG. 21. Substrate selectivity of thrombin-stimulated growth cone PLA$_2$. GCPs were assayed in the absence (control) of presence of 100 nM thrombin (thr) with 10 µM CaCl$_2$ and equal concentrations of either $^{14}$C-AA-PI, -PE, or -PC as substrate. Numbers above thrombin columns indicate increase in activity relative to control levels. Data are averages of 3 experiments, all done in triplicate, error bars indicate s.e.m.

In a previous publication (Nègre-Aminou et al., 1996), we reported that GCPs contain at least two biochemically separable $PLA_2$ activities selective for PI and PE, respectively. Under experimental conditions used at the time, PC hydrolysis in GCPs was at background level without stimulation. However, FIG. 21 shows that thrombin stimulates AA release from all three phospholipid substrates, but at different levels, ranging from about 5-fold for PI to about 7-fold for PC.

Figure 19:
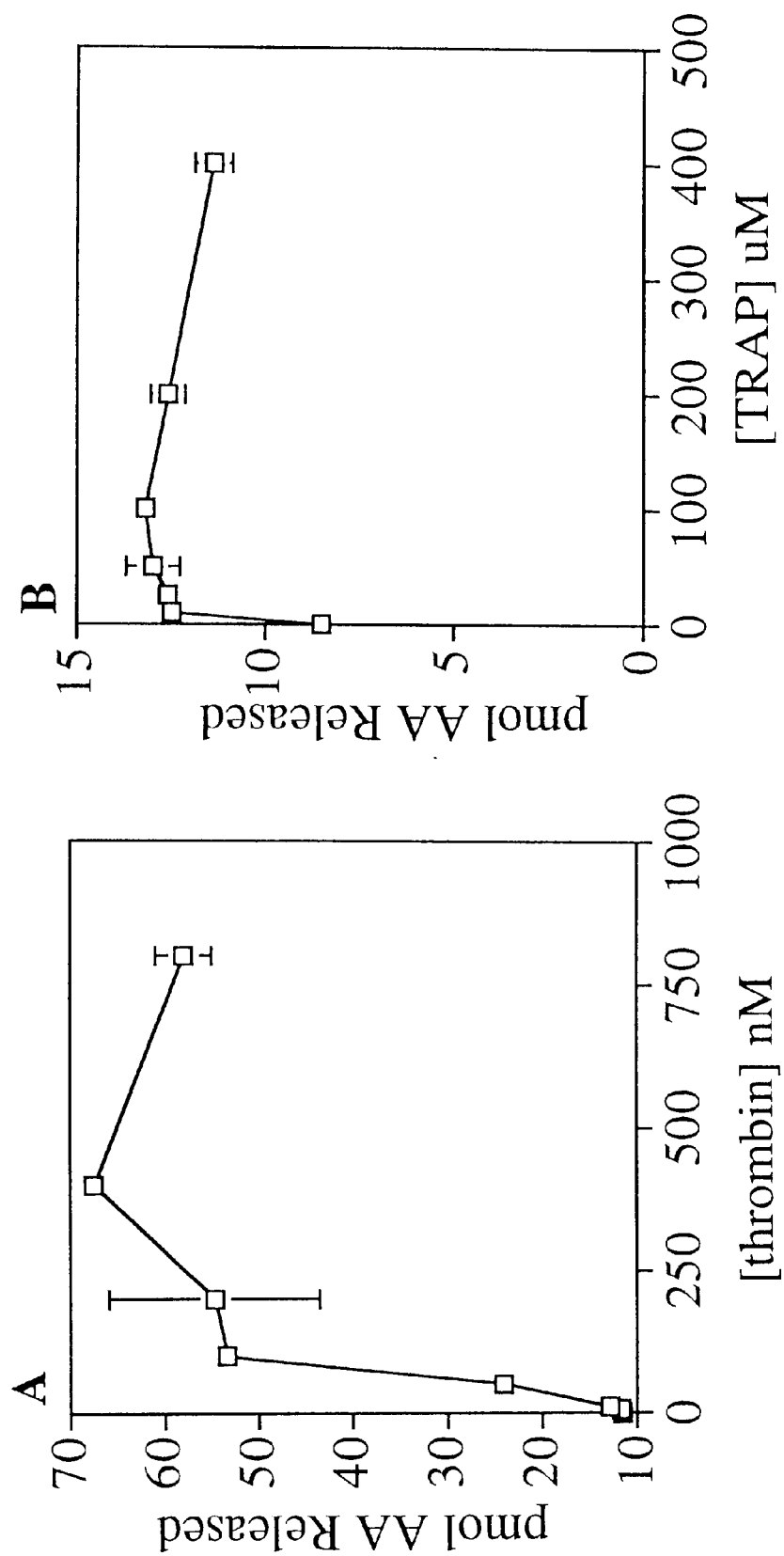
FIGS. 19A–19B. Dose Response curves of PLA$_2$ activation by thrombin (A) and TRAP (B) in GCPs. GCPs were incubated for 10 minutes on ice with varying concentrations of thrombin (A) or TRAP (B), then for 10 minutes at 37° C. in the reaction mixture, in the presence of 10 µM CaCl$_2$. The substrate was $^{14}$C-AA-PI. The data presented are in triplicate. The error bars represent s.d.; where not present error bars were too small to be indicated.
Figure 22:
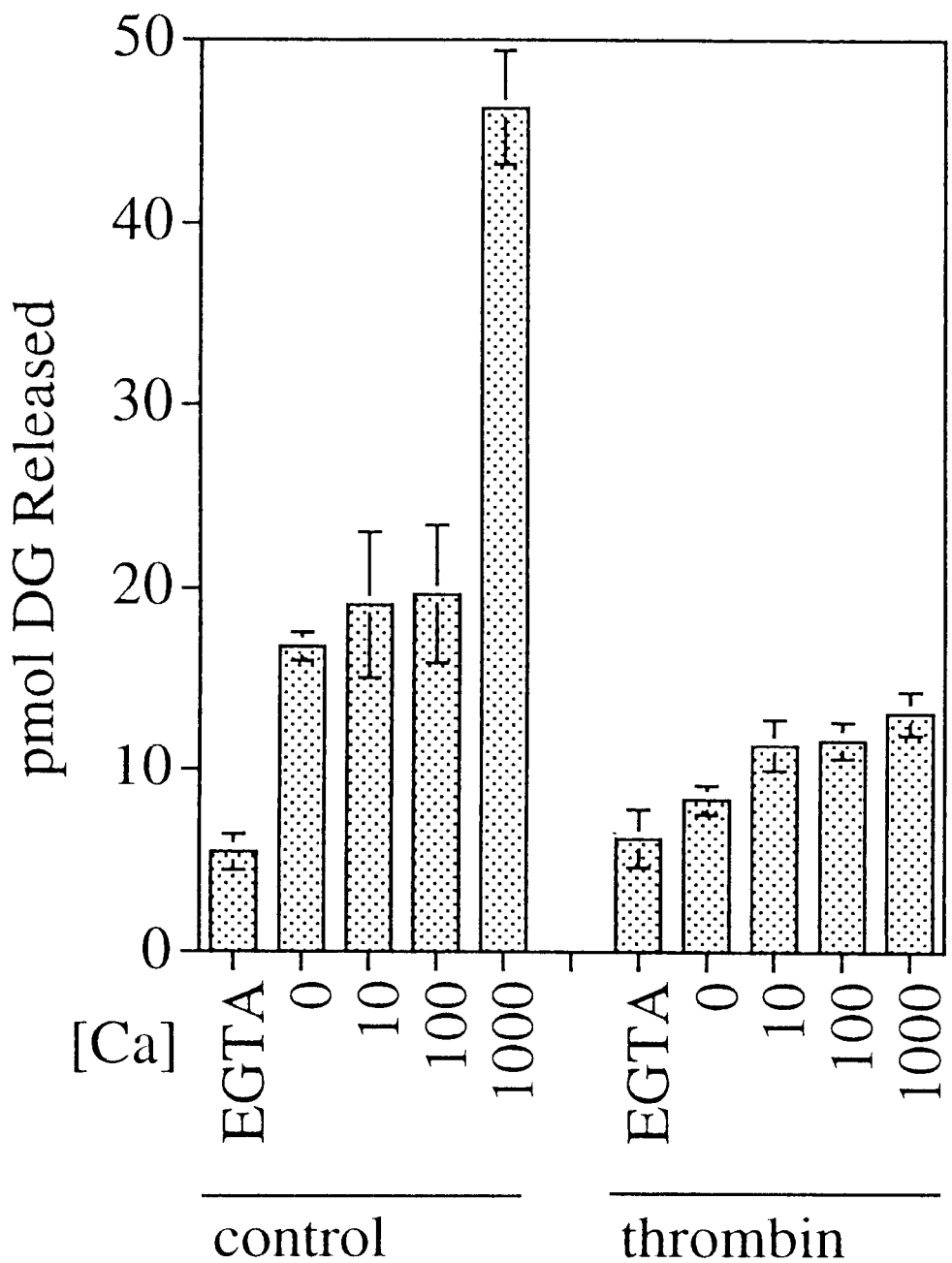
FIG. 22. Thrombin inhibits growth cone PLC in a calcium-dependent manner. GCPs were incubated alone (control) or in the presence of 100 nM thrombin for 10 minutes on ice, then combined with substrate ($^{14}$C-AA-PI) for 10 minutes at 37° C., in the presence of EGTA or varying $\mu$M concentrations of CaCl$_2$ ("0 Ca" indicates no addition of Ca$^{2+}$ or EGTA). DG release was measured as described in Methods. Data represent several experiments, each done in triplicate. Error bars are s.d.
Figure 23:
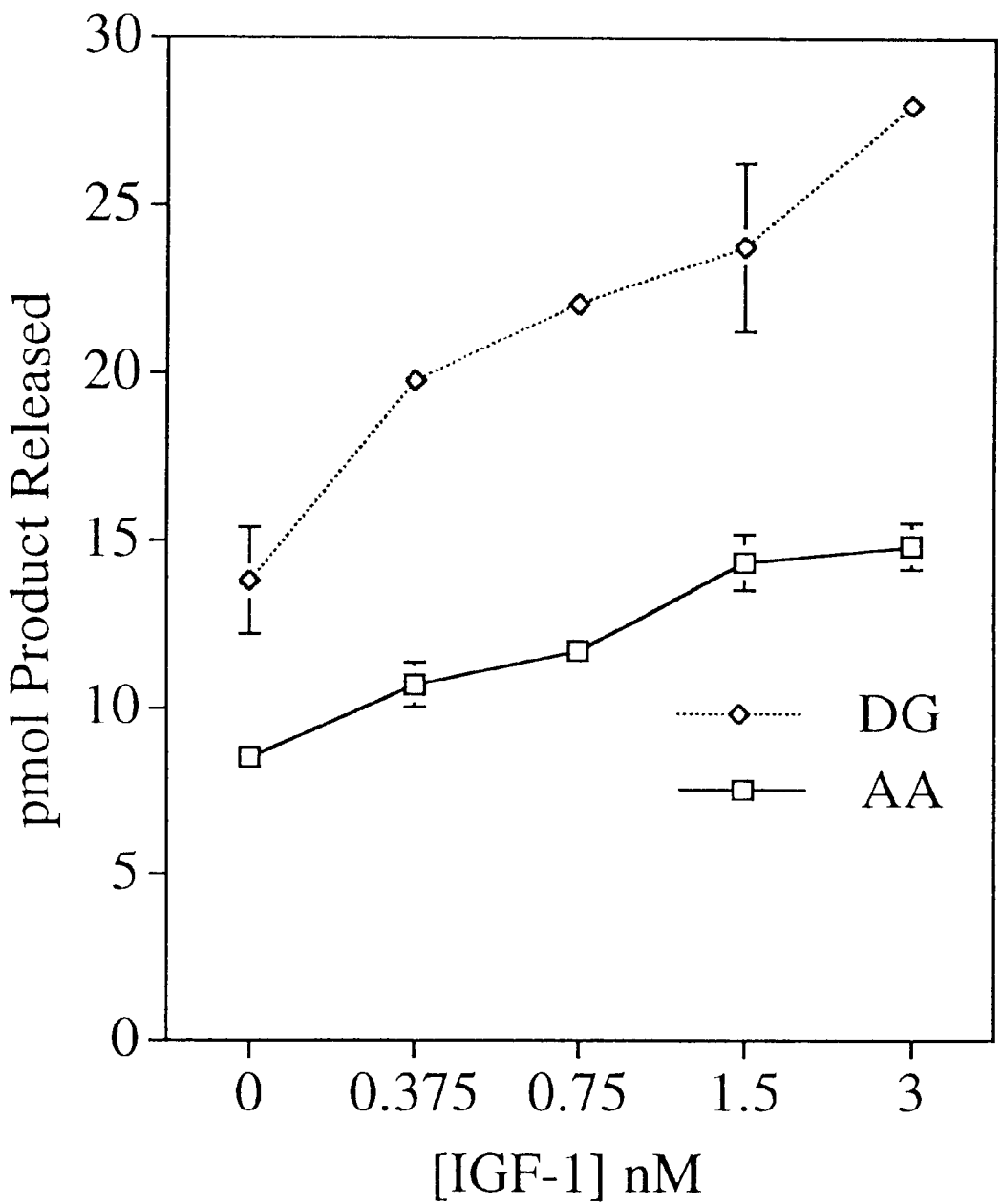
FIG. 23. IGF-1 stimulation of PLC and PLA$_2$ in growth cones. GCPs were assayed for both PLA$_2$ and PLC activity as described, in the presence of 10 $\mu$M CaCl$_2$ and varying concentrations of IGF-1, using $^{14}$C-AA-PI as substrate and recovering $^{14}$C-AA and $^{14}$C-AA-DG as products. Data are averages of several experiments, each done in triplicate. Error bars indicate s.d. Where no error bars appear s.d. was too small to register.

In other systems, such as platelets, thrombin has been reported to activate PLC (Crouch and Lapetina, *J. Biol. Chem.*, 263:3363–3371 (1998); Huang et al., *J. Biol. Chem.*, 266:18435–18438 (199)). Therefore, we measured diacylglycerol (DG) release from PI in parallel to AA release. FIG. 22 shows that thrombin inhibits DG release, rather than stimulating it, and that the effect is calcium-dependent in a manner similar to the stimulation of $PLA_2$. In order to ascertain the authenticity of thrombin-induced PLC inhibition, we compared the effects of thrombin and insulin-like growth factor 1 (IGF-1) on $PLA_2$ and PLC in GCPs. GCPs are known to be rich in IGF-1 receptors and IGF-1 is known to activate PLC in many systems. FIG. 23 shows AA and DG release from PI (at 10 μM free $Ca^{2+}$) in response to different concentrations of IGF-1. In the low nanomolar range, IGF-1 does indeed stimulate DG release in GCPs, approximately two-fold (FIG. 23). IGF-1 also stimulates AA release from PI, but only about 1.7 fold. This acuvanon or PLA$_2$ is a much weaker response than that observed with thrombin (see FIGS. 19 and 21).

Because of the mild stimulation of PLA2 by IGF-1, we assayed for PLA$_2$ activation by other trophic factors whose receptors are known to be present on growth cones or to be linked to PLA$_2$ stimulation in other cellular systems. (In these experiments, shown in Table 3, net control levels of PLA$_2$ activity in GCPs range from 38 to 107 pmol AA released/min/mg protein, probably because of slight variations in the GCP fraction. However, data sets are shown always with controls measured in the same experimental series.) TrkB, the receptor for brain-derived neurotrophic factor (BDNF), is readily detectable by immunoblot and enriched in GCPs isolated from whole fetal brain. However, BDNF did not significantly stimulate PLA$_2$ activity in GCPs (Table 3c). BDNF combined with IGF-1 or insulin alone also failed to stimulate PLA$_2$ significantly in our assays (Table 3c).

TABLE 3

PLA$_2$ Activity in Neurons and Growth Cones a) Whole neurons versus GCPs.

| condition | concentration nM | substrate | net activity (pmol/min/mg protein) | |
| --- | --- | --- | --- | --- |
| | | | intact neurons | GCPs |
| control | — | PI | 0.6 ± 0.45 | 37.9 ± 1.1 |
| | | PE | 4.4 ± 0.99 | 25.7 ± 2.3 |
| thrombin | 100 | PI | 42.5 ± 16 | 262 ± 47 |
| | | PE | 26.8 ± 1.9 | 210.2 ± 4.8 | b) Effect of reduction on PLA$_2$ activity in GCPs.

| condition | concentration nM | substrate | net activity (pmol/min/mg protein) | |
| --- | --- | --- | --- | --- |
| | | | no DTT | 50 nM DTT |
| control | — | PI | 41.9 ± 1.1 | 66.0 ± 4.7 |
| thrombin | 100 | PI | 221 ± 39.9 | 223 ± 53.4 | c) Response of GCPs to different factors.

| condition | concentration nM | substrate | net activity (pmol/min/mg protein) |
| --- | --- | --- | --- |
| control | — | PI | 159 ± 6.2 |
| BDNF | 100 | PI | 164 ± 10.6 |
| IGF-1 | 0.75 | PI | 177 ± 14.5 |
| BDNF + IGF-1 | 100/0.75 | PI | 154 ± 12.4 |
| insulin | 1 | PI | 158 ± 8.4 |
| thrombin | 200 | PI | 355 ± 28.0 |

Figure 24:
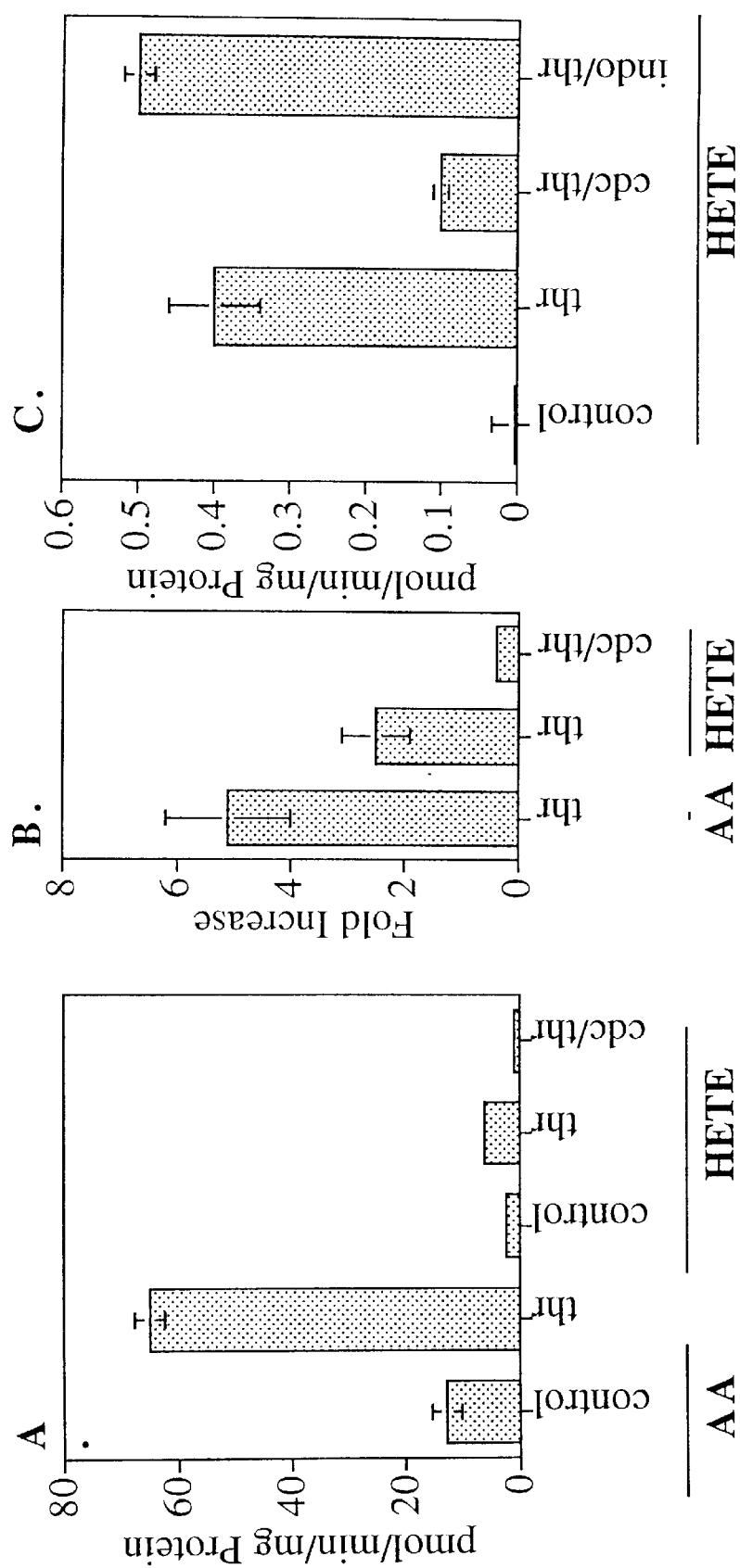
FIGS. 24A–24C. Thrombin-stimulated release of AA and HETE. GCPs were assayed for both PLA$_2$ and Lox activity as described. Inhibitor (0.156 $\mu$M or 0.2 $\mu$M indomethacin) was introduced to some GCP samples for 5 minutes on ice prior to the addition of 100 nM thrombin. Following an additional 10 minutes incubation on ice, the GCP mixture was then incubated with either $^{14}$C-AA-PC (A,B) or $^3$H-AA (C), in the presence of 10 $\mu$M CaCl$_2$ for 5 minutes at 37° C. A and B show thrombin-stimulated release of AA and HETE in assays using the PC substrate, as actual amounts (A) and fold increase (B). C illustrates thrombin stimulation of HETE directly from the AA substrate. In A and B, values for control and thrombin-stimulated conditions were averaged from 6 experiments, all done in triplicate, while the values for CDC and indomethacin-treated GCPs were averaged from 2 experiments, done in triplicate. Data in C are from one representative experiment, done in triplicate. Error bars indicate s.d.; where not seen, error bars were too small to be indicated.

Generation of Eicosanoid. The effect of CDC in collapse and growth cone detachment assays suggests that eicosanoid synthesis from AA is an important step in thrombin/TRAP signalling. Lipid extracts prepared in acid conditions can be resolved by TLC to separate 12- and 15-HETE (which co-migrate) from the other compounds, including AA, DG and 5-HETE (Birkle et al., 1988). With this approach we studied the generation of HETE in GCPs, without or with thrombin stimulation. FIG. 24A shows, in assays involving $^{14}$C-AA-PC as a substrate, the generation of AA and of a compound co-migrating in TLC with 12- or 15-HETE. As seen already, there is substantial stimulation of AA release by thrombin. Radioactivity co-migrating with 12-HETE also is increased, approximately 2.5-fold above control (FIG. 24B). The selective 12-Lox inhibitor, CDC, reduces thrombin-stimulated HETE levels to below control, suggesting that this compound is indeed 12- and/or 15-HETE. This experiment indicates that thrombin stimulates HETE synthesis in GCPs, but it does not discriminate between the activation of PLA$_2$ (shown by increased AA release) and the possible stimulation of Lox activity.

In order to determine whether thrombin regulates Lox activity, analogous assays were performed with $^3$H-AA as the substrate (total AA concentration, about 8 μM. As shown in FIG. 24C, thrombin does indeed stimulate HETE production from AA, and the effect is strongly inhibited by CDC, but not by the cyclooxygenase blocker, indomethacin. This suggests thrombin activation of Lox, in addition to PLA$_2$. However, the amount of HETE generated upon thrombin stimulation is only a small fraction of the amount of AA released (FIG. 24A).

Although TLC is suitable for isolating eicosanoids, identification of the compounds is based on co-migration with standards. Therefore, we performed mass-spectrometric analysis (a) to ascertain HETE identity of the $^{14}$C-AA-PC- or $^3$H-AA-derived substance co-migrating in TLC with 12(S)-HETE and (b) to identify HETE isomers endogenously generated by growth cones. HETE isomers have a negative ion m/z of 319. However, when 12(S)-HETE is first run on TLC, subsequently desorbed from the silica and then analyzed by MS, it generates a primary negative ion peak at m/z 381. Extracts from control GCPs subjected to the same procedure also contain a predominant peak at m/z 381, in the TLC band co-migrating with 12(S)-HETE. This peak is increased nearly 2-fold if GCPs are first stimulated with thrombin. Thus, MS supported the assumption that the TLC band analyzed to determine Lox activity contained 12- or 15-HETE.

Figure 25:
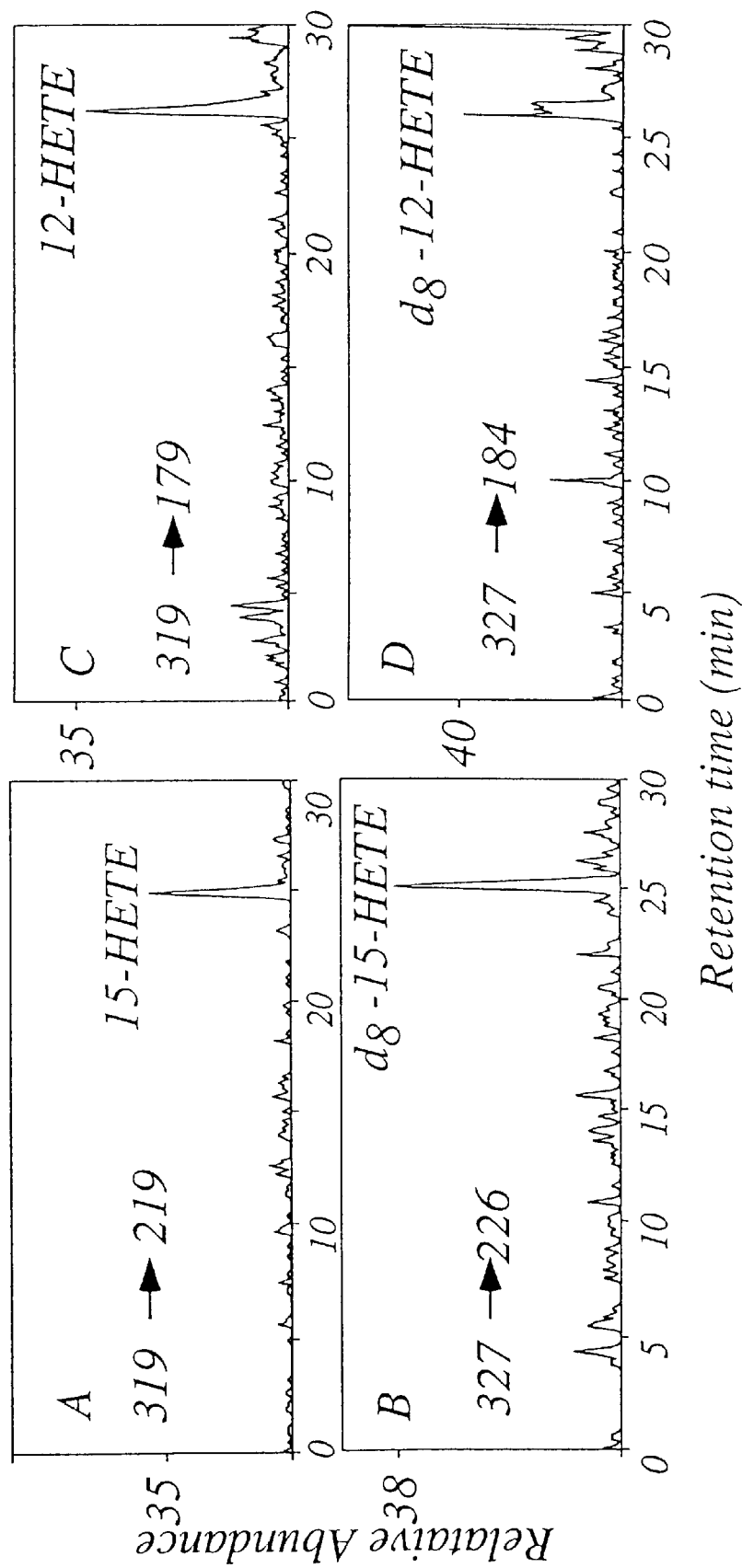
FIGS. 25A–D show HPLC elution patterns. The abscissa indicates relative detection levels of fragments derived from HETE isomers (negative ion m/z 319.3) and characteristic of 12-HETE (fragment m/z 179.1) (FIGS. 25C and 25D) and 15-HETE (fragment m/z 219.1) (FIGS. 25A and 25B), respectively.

LC/MS$^2$ was used to demonstrate GCP synthesis of specific HETE isomer(s). FIG. 25 shows HPLC elution patterns. The abscissa indicates relative detection levels of fragments derived from HETE isomers (negative ion m/z 319.3) and characteristic of 12-HETE (fragment m/z 179.1) and 15-HETE (fragment m/z 219.1), respectively. Based on scale and peak width, 12-HETE is the predominant species, but a significant level of 15-HETE is evident. 5-HETE was not detected.

The generation of 12- and 15-HETE by growth cones, the inhibition of this synthesis by CDC (at 0.156 μM), and the inhibition of the thrombin effect on growth cone morphology by CDC suggest that growth cones contain one or several forms of 12-Lox. To test for this possibility, we analyzed GCPs by Western blot with the two 12-Lox antibodies currently available, specific for platelet and leukocyte 12-Lox, respectively. Gels contained equal amounts of protein from fetal-brain low-speed supernatant (LSS, the crude parent fraction of GCPs) and GCPs. The results indicate that GCPs are significantly enriched, relative to LSS, in a protein of about 75 kDa and reactive with the antibody to leukocyte 12-Lox. No immunoreactivity was detected with anti-platelet 12-Lox antibody.

3. Discussion

Thrombin as a Growth Cone Repellent. Thrombin receptor activation leads to diverse cellular responses, such as secretion and pseudopod spreading in platelets, and locomotion and mitogenesis in fibroblasts. However, it causes cell rounding in endothelial and neural cells and pseudopod withdrawal in certain cancer cells (Grand et al., *Biochem J.* 313:353–368 (1996); Jalink and Moolenaar, *J. Cell Biol.*, 118:411–419(1992); Vouret-Craviari et al., *Mol. Biol. Cell*, 9:2639–2653 (1998)). In neurons, thrombin induces growth cone collapse comprising redistribution and partial depolymerization of the actin skeleton as well as detachment of filopodia and lamellipodia. This is very similar to collapse induced by other factors (e.g., Kapfhammer and Raper, *J. Neurosci*, 7(5):1595–1600 (1987; Fan et al., *J. Cell Biol.*, 121:867–878 (1993)). TRAP mimics the effect of thrombin, indicating that this is a receptor-mediated event, not dependent on proteolysis of adhesion molecules or their extracellular ligands. Thus, thrombin qualifies as a bona-fide collapsing factor and repellent.

Activation of Phospholipase and Lipoxygenase. In plaelets, thrombin activates both $cPLA_2$ and PLC. It seemed logical, therefore, to assay for these enzymes in cultures of thrombin-responsive primary neurons. Isolated growth cones were of particular interest in view of the enrichment of at least two different $cPLA_2$s in them (Nègre-Aminou et al., 1996; whether the two enzymes occur separately in distinct growth cone populations, or together in all GCPs in unknown).

Thrombin and, to a lesser extent, TRAP stimulate $PLA_2$ activity in primary neurons and GCPs, with the highest levels of free AA achieved in GCPs. Growth factors whose receptors are present on GCPs, such as BDNF, NGF, insulin and IGF-1, stimulate growth cone $cPLA_2$ only weakly or not at all, indicating that thrombin activation is selective. Thrombin increases AA release from phospholipid from 7- to 5-fold, with the substrate preference PC>PE>PI. Resting as well as stimulated levels of $PLA_2$ activity are resistant to reducing agents, excluding a contribution of secreted $PLA_2$. PC hydrolysis had not previously been detected in unstimulated GCPs (Nègre-Aminou et al., 1996). Thus, present results suggest a third, PC-selective $cPLA_2$ may possibly exist in GCPs. We show that thrombin activation of $cPLA_2$ requires $Ca^{2+}$. However, Nègre-Aminou et al. (1996) reported PE- and PI-selective $cPLA_2$s to be $Ca^{2+}$-independent. Therefore, $Ca^{2+}$ is likely to be necessary for a signalling step upstream of $cPLA_2$.

While growth cones and platelets share receptor-mediated thrombin stimulation of $cPLA_2$, they are different with regard to PLC regulation. Thrombin stimulates platelet PLC but inhibits this phosphoinositidase in GCPs. PLC activation causes the release of $IP_3$ and subsequent efflux of $Ca^{2+}$ from intracellular storage sites. Our observations thus suggest that release of $Ca^{2+}$ from intracellular stores is not important for the collapse response. Thrombin-induced $Ca^{2+}$ transients have been reported for platelets (see Grand et al., 1996) and neuroblastoma cells (Jalink and Moolenaar, 1992), but they were shown not to be necessary for thrombin-induced rounding of neuroblastoma and endothelial cells (Jalink and Moolenaar, 1992; Vouret-Craviari et al., 1998). Therefore, our findings are consistent with these observations as well as the fact that (at least so far) $Ca^{2+}$ transients have not been detectable in nerve growth cones treated with repellents. The second consequence of PLC stimulation, the release of DG, activates PKC in platelets. Lack of PLC stimulation in thrombin-treated GCPs, however, does not rule out a role for PKC in repellent action.

$cPLA_2$s cleave phospholipids into an unsaturated fatty acid, in brain typically AA, and a lysophospholipid. Whether lyso-PI, -PE and -PC generated in growth cones have functional role(s) is not known. Most released AA is rapidly reincorporated into phospholipid (Nègre-Aminou and Pfenninger, 1993), but AA may directly influence growth cone functions and/or may be converted into one or more eicosanoids (Smith, *Biochem J.*, 259:315–324 (1989); Shimizu and Wolfe, *J. Neurochem.*, 55:1–15 (1990)). Our biochemical studies show that thrombin stimulates in growth cones not only the release of AA but also the synthesis of an AA-derived compound that co-extracts and co-migrates in TLC with 12- or 15-HETE. The generation of this product is inhibited by the selective 12-Lox blocker, CDC, but not by the cyclooxygenase inhibitor, indomethacin. MS analysis of the material eluted from TLC at the same $R_f$ reveals a single major peak at m/z 381, the negative ion m/z seen for pure 12(S)-HETE subjected to the same extraction and TLC protocol. (The observed compound may be an acetylated and reduced derivative produced during TLC, as suggested by variations of the protocol). In agreement with the radiolabel data, the peak seen at m/z 381 is increased significantly by thrombin stimulation of GCPs prior to extraction. Finally, $LC/MS^2$ analysis of GCP extracts definitively demonstrates GCP synthesis of primarily 12- and also 15-HETE, but not of 5-HETE.

In summary, our results demonstrate strong and selective thrombin stimulation of one or multiple $cPLA_2$s in growth cones, followed by conversion of some of the released AA into 12- and 15-HETE. We estimate the conversion to amount to about 1 pmole, or 5%, out of approximately 20 pmoles AA released in the same assay (assuming equal recoveries). Although we cannot exclude a role of 15-Lox in GCPs, HETEs are likely to be synthesized by 12-Lox because of the selective inhibitory effect of CDC at 0.156 $\mu$m (Cho et al., 1991) and a recent report that 12-Lox also generates 15 (Yamamoto, *Prog. Lipid Res.* 36(1):23–41 (1991)). This view is consistent with the observation that growth cones are enriched in a polypeptide that co-migrates in SDS-PAGE with 12-Lox (at 75 kDa) and immunocrossreacts with an antibody to leukocyte-type 12-Lox (but not platelet 12-Lox).

It is generally assumed that eicosanoid synthesis, including that of 12-HETE, is regulated by the supply of AA, and that 12-Lox is constitutively active (Smith, 1989; Shimizu and Wolfe, 1990; Yamamoto et al., 1997). However, we observed that thrombin stimulates not only $cPLA_2$ but also the Lox in GCPs.

Functional Role of Lipid Messengers in Growth Cone Collapse. The data discussed so far correlate thrombin's collapsing effect with $cPLA_2$ activation and eicosanoid synthesis. In order to determine whether a causal relationship exists, inhibitor experiments were performed. Selective inhibitors of most or all growth cone $cPLA_2$ activity are not known, but exist for eicosanoid synthesis. The cyclooxygenase inhibitor indomethacin does not interfere with thrombin-induced growth cone collapse. However, the general Lox inhibitor, NDGA, and the specific 12-Lox inhibitor, CDC, block thrombin- and TRAP-induced collapse, as well as Lox activity in biochemical assays. Conversely, exogenous 12(S)-HETE added to cultures mimics the effects of thrombin or TRAP. These results are consistent with the observed thrombin stimulation of HETE synthesis and link $cPLA_2$ activation and HETE synthesis functionally to the collapse mechanism.

As pointed out earlier, growth cone collapse involves filopodial and larmellipodial detachment and withdrawal, as well as reorganization of the actin cytoskeleton. Our growth cone detachment assay and the effect of CDC dissociate these two phenomena: Thrombin and TRAP trigger GCP detachment from laminin. Disassembly of the actin cytoskeleton with cytochalasin D or inhibition of myosin ATPase with BDM interfere to some degree with GCP attachment, but rather than blocking thrombin-induced detachment, they facilitate it. So, detachment does not require an intact actin cytoskeleton, at least in these assays. A complementary observation is that intact growth cones pretreated with CDC and then challenged with thrombin retain their spread-out, attached filopodia and overall shape, but phalloidin staining often reveals peripherally depleted and proximally condensed F-actin. These results taken together suggest that cPLA$_2$ and 12-Lox are involved in triggering detachment rather than cytoskeletal redistribution. Because Lox inhibitors do not seem to affect thrombin-induced change of the actin cytoskeleton, signalling to this entity seems to follow an alternate pathway, presumably involving Rho-family G-proteins (see Jalink et al., 1994; Vouret-Craviari, 1998).

In conclusion, our data suggest that the growth cone repellent, thrombin, activates a branching signalling cascade, with one path leading to redistribution of the actin cytoskeleton and the other (involving cPLA$_2$ and 12-Lox) triggering pseudopod detachment. The results indicate that eicosanoid synthesis is necessary and the 12-Lox product, 12(S)-HETE, sufficient to cause pseudopod detachment, presumably via disassembly of adhesion sites. The modes of action of 12(S)- and 15(S)-HETE are not known, but our preliminary data suggest the involvement of PKC activation and phosphorylation of the adhesion site-associated protein, MARCKS and/or MacMARCKS (de la Houssaye et al., *Mol. Biol. Cell*, 8:265a(1997); Mikule et al., Soc. Neurosci Abstracts, 23(part 1), p. 600 (1997)).

While the exemplary preferred embodiments of the present invention are described herein with particularity, those having ordinary skill in the art will recognize various changes, modificatins, additions, and applications other than those specifically described herein, and may adapt the preferred embodiments and methods without departing from the spirit of the invention.

What is claimed is:

1. A method of identifying an agent that reduces the ability of a neurite repellent to inhibit neurite growth, comprising:
   a. attaching neuronal growth cones to a substratum;
   b. exposing the attached neuronal growth cones to a putative agent in the presence of a known repellent; and
   c. determining the amount of attached or detached neuronal growth cones, wherein the putative agent reduces the ability of a neurite repellent to inhibit neurite growth if more of the neuronal growth cones remain attached to the substratum in the presence of said putative agent and said known repellent as compared to in the absence of said putative agent and in the presence of said known repellent.

2. The method of claim 1, wherein the neuronal growth cones are attached on a substratum in a modified Kreb's buffer.

3. The method of claim 1, wherein the step (a) of attaching said neuronal growth cones to a substratum comprises centrifuging said neuronal growth cones on said substratum for up to sixty minutes at a speed of at least about 2,000×g.

4. The method of claim 1, wherein the step (a) of attaching said neuronal growth cones to a substratum comprises centrifuging said neuronal growth cones on said substratum for about 15 minutes at about 5,000×g at room temperature.

5. The method of claim 1, wherein step (c) is determined by the amount of neuronal growth cones that remain attached to the substratum, wherein the putative agent is effective to reduce the ability of a repellent to inhibit neurite growth if at least 75% of the neuronal growth cones remain attached to the substratum.

6. The method of claim 1, wherein step (c) is determined by the amount of neuronal growth cones that remain attached to the substratum, wherein the putative agent is effective to reduce the ability of a repellent to inhibit neurite growth if at least 85% of the neuronal growth cones remain attached to the substratum.

7. The method of claim 1, wherein step (c) is determined by the amount of neuronal growth cones that remain attached to the substratum, wherein the putative agent is effective to reduce the ability of a repellent to inhibit neurite growth if at least 95% of the neuronal growth cones remain attached to the substratum.

8. The method of claim 1, wherein the substratum comprises extracellular matrix molecules or cellular adhesion molecules.

9. The method of claim 8, wherein the extracellular matrix molecules are laminin, fibronectin, collagen or a combination thereof.

10. The method of claim 8, wherein the cellular adhesion molecules are L1, N-CAM, cadherin, glycolipids, synthetic polypeptides, oligosaccharides or a combination thereof.

11. The method of claim 1, wherein the substratum is coated with nitrocellulose.

12. The method of claim 1, wherein the known repellant is selected from the group consisting of thrombin and a semaphorin.

13. The method of claim 1, wherein said method further comprises a step of measuring a parameter selected from the group consisting of neuronal growth cone elongation, neuronal growth cone retraction, cell extension, adhesion site formation, adhesion site detachment, and activation of a parameter within the signaling pathway.

14. The method of claim 1, wherein said method further comprises a step of measuring whether the putative agent inhibits the activation of a parameter in the repellent signaling pathway.

15. The method of claim 14, wherein said parameter in the repellent signaling pathway is selected from the group consisting of cytosolic phospholipase A$_2$ (cPLA$_2$), 12-lipoxygenase (12-LOX) and protein kinase C.

16. The method of claim 1, wherein said known repellent agent is identified by a method comprising:
   a. attaching neuronal growth cones on a substratum;
   b. exposing the attached neuronal growth cones to a putative repellent agent; and
   c. determining the effect of the putative repellent agent on the neuronal growth cones, wherein detachment of at least about 35% of the neuronal growth cones from the substratum in the presence of the putative repellent agent indicates the putative repellent agent is an effective repellent agent.

17. The method of claim 1, wherein said known repellent is identified by a method comprising:
   a. obtaining whole neural cells or neuronal growth cones;
   b. exposing the whole neural cells or neuronal growth cones to a putative repellent agent; and
   c. measuring a parameter on the repellent signaling pathway, wherein the putative repellent agent inhibits cell motility if the parameter is activated.

* * * * *